(12) United States Patent
Paldi et al.

(10) Patent No.: US 10,888,579 B2
(45) Date of Patent: *Jan. 12, 2021

(54) COMPOSITIONS FOR CONFERRING TOLERANCE TO VIRAL DISEASE IN SOCIAL INSECTS, AND THE USE THEREOF

(71) Applicant: Beeologics Inc., St. Louis, MO (US)

(72) Inventors: Nitzan Paldi, Moshav Bar Giora (IL); Gal Yarden, St. Louis, MO (US)

(73) Assignee: BEEOLOGICS INC., St. Louis, MO (US)

(*) Notice: Subject to any disclaimer, the term of this patent is extended or adjusted under 35 U.S.C. 154(b) by 480 days.

This patent is subject to a terminal disclaimer.

(21) Appl. No.: 13/932,051

(22) Filed: Jul. 1, 2013

(65) Prior Publication Data

US 2013/0289097 A1 Oct. 31, 2013

Related U.S. Application Data

(63) Continuation of application No. 13/332,430, filed on Dec. 21, 2011, now Pat. No. 8,507,457, which is a continuation of application No. 12/222,949, filed on Aug. 20, 2008, now Pat. No. 8,097,712.

(60) Provisional application No. 60/996,244, filed on Nov. 7, 2007.

(51) Int. Cl.
  *C12N 15/11* (2006.01)
  *A61K 31/713* (2006.01)
  *C12N 15/113* (2010.01)

(52) U.S. Cl.
  CPC .......... *A61K 31/713* (2013.01); *C12N 15/113* (2013.01); *C12N 15/1131* (2013.01); *C12N 2310/14* (2013.01); *C12N 2770/22022* (2013.01)

(58) Field of Classification Search
  CPC .... A61K 31/713; C12N 15/11; C12N 15/113; C12N 15/1131; C12N 2310/14
  See application file for complete search history.

(56) References Cited

U.S. PATENT DOCUMENTS

| | | | |
|---|---|---|---|
| 3,687,808 A | 8/1972 | Merigan et al. |
| 3,984,533 A | 10/1976 | Uzgiris |
| 3,996,345 A | 12/1976 | Ullman et al. |
| 4,469,863 A | 9/1984 | Ts'o et al. |
| 4,476,301 A | 10/1984 | Imbach et al. |
| 4,535,060 A | 8/1985 | Comai |

(Continued)

FOREIGN PATENT DOCUMENTS

| AU | 2008325989 | 5/2009 |
|---|---|---|
| AU | 2008258254 | 7/2014 |

(Continued)

OTHER PUBLICATIONS

Amdam et al, J. Theoretical Biol. 223:451-464, 2003.*

(Continued)

*Primary Examiner* — Kevin K Hill
(74) *Attorney, Agent, or Firm* — Arnold & Porter Kaye Scholer LLP; Amanda Carmany-Rampey; David R. Marsh

(57) ABSTRACT

Compositions and methods for reducing susceptibility to infectious disease in bees using RNA interference technology, and more particularly, prevention and treatment of viral infections in honeybees such as Israel acute paralysis virus (IAPV) by feeding of pathogen-specific dsRNA. Further, multiple-pathogen specific dsRNA is disclosed.

19 Claims, 14 Drawing Sheets

Specification includes a Sequence Listing.

(56) References Cited

U.S. PATENT DOCUMENTS

| | | |
|---|---|---|
| 4,581,847 A | 4/1986 | Hibberd et al. |
| 4,732,250 A | 3/1988 | Maucher et al. |
| 4,761,373 A | 8/1988 | Anderson et al. |
| 4,769,061 A | 9/1988 | Comai |
| 4,810,648 A | 3/1989 | Stalker |
| 4,940,835 A | 7/1990 | Shah et al. |
| 4,971,908 A | 11/1990 | Kishore et al. |
| 5,004,863 A | 4/1991 | Umbeck |
| 5,013,659 A | 5/1991 | Bedbrook et al. |
| 5,015,580 A | 5/1991 | Christou et al. |
| 5,023,243 A | 6/1991 | Tullis |
| 5,034,506 A | 7/1991 | Summerton et al. |
| 5,094,945 A | 3/1992 | Comai |
| 5,141,870 A | 8/1992 | Bedbrook et al. |
| 5,145,783 A | 9/1992 | Kishore et al. |
| 5,159,135 A | 10/1992 | Umbeck |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,642 A | 2/1993 | Shah et al. |
| 5,188,897 A | 2/1993 | Suhadolnik et al. |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,634 A | 2/1994 | Stadler et al. |
| 5,286,717 A | 2/1994 | Cohen et al. |
| 5,304,732 A | 4/1994 | Anderson et al. |
| 5,310,667 A | 5/1994 | Eichholtz et al. |
| 5,312,910 A | 5/1994 | Kishore et al. |
| 5,321,131 A | 6/1994 | Agrawal et al. |
| 5,331,107 A | 7/1994 | Anderson et al. |
| 5,339,107 A | 8/1994 | Henry et al. |
| 5,346,107 A | 9/1994 | Bouix et al. |
| 5,378,824 A | 1/1995 | Bedbrook et al. |
| 5,390,667 A | 2/1995 | Kumakura et al. |
| 5,392,910 A | 2/1995 | Bell et al. |
| 5,393,175 A | 2/1995 | Courville |
| 5,399,676 A | 3/1995 | Froehler |
| 5,405,938 A | 4/1995 | Summerton et al. |
| 5,405,939 A | 4/1995 | Suhadolnik et al. |
| 5,416,011 A | 5/1995 | Hinchee et al. |
| 5,453,496 A | 9/1995 | Caruthers et al. |
| 5,455,233 A | 10/1995 | Spielvogel et al. |
| 5,459,127 A | 10/1995 | Felgner et al. |
| 5,460,667 A | 10/1995 | Moriyuki et al. |
| 5,462,910 A | 10/1995 | Ito et al. |
| 5,463,174 A | 10/1995 | Moloney et al. |
| 5,463,175 A | 10/1995 | Barry et al. |
| 5,466,677 A | 11/1995 | Baxter et al. |
| 5,470,967 A | 11/1995 | Huie et al. |
| 5,476,925 A | 12/1995 | Letsinger et al. |
| 5,489,520 A | 2/1996 | Adams et al. |
| 5,489,677 A | 2/1996 | Sanghvi et al. |
| 5,491,288 A | 2/1996 | Chaubet et al. |
| 5,510,471 A | 4/1996 | Lebrun et al. |
| 5,518,908 A | 5/1996 | Corbin et al. |
| 5,519,126 A | 5/1996 | Hecht |
| 5,536,821 A | 7/1996 | Agrawal et al. |
| 5,538,880 A | 7/1996 | Lundquist et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,550,318 A | 8/1996 | Adams et al. |
| 5,550,398 A | 8/1996 | Kocian et al. |
| 5,550,468 A | 8/1996 | Häberlein et al. |
| 5,558,071 A | 9/1996 | Ward et al. |
| 5,561,225 A | 10/1996 | Maddry et al. |
| 5,561,236 A | 10/1996 | Leemans et al. |
| 5,563,253 A | 10/1996 | Agrawal et al. |
| 5,569,834 A | 10/1996 | Hinchee et al. |
| 5,571,799 A | 11/1996 | Tkachuk et al. |
| 5,587,361 A | 12/1996 | Cook et al. |
| 5,591,616 A | 1/1997 | Hiei et al. |
| 5,593,874 A | 1/1997 | Brown et al. |
| 5,596,086 A | 1/1997 | Matteucci et al. |
| 5,597,717 A | 1/1997 | Guerineau et al. |
| 5,602,240 A | 2/1997 | De Mesmaeker et al. |
| 5,605,011 A | 2/1997 | Bedbrook et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,061 A | 5/1997 | Barry et al. |
| 5,633,360 A | 5/1997 | Bischofberger et al. |
| 5,633,435 A | 5/1997 | Barry et al. |
| 5,633,448 A | 5/1997 | Lebrun et al. |
| 5,639,024 A | 6/1997 | Mueller et al. |
| 5,646,024 A | 7/1997 | Leemans et al. |
| 5,648,477 A | 7/1997 | Leemans et al. |
| 5,663,312 A | 9/1997 | Chaturvedula |
| 5,677,437 A | 10/1997 | Teng et al. |
| 5,677,439 A | 10/1997 | Weis et al. |
| 5,714,331 A | 2/1998 | Buchardt et al. |
| 5,719,046 A | 2/1998 | Guerineau et al. |
| 5,719,262 A | 2/1998 | Buchardt et al. |
| 5,731,180 A | 3/1998 | Dietrich |
| 5,739,180 A | 4/1998 | Taylor-Smith |
| 5,746,180 A | 5/1998 | Jefferson et al. |
| 5,767,361 A | 6/1998 | Dietrich |
| 5,767,373 A | 6/1998 | Ward et al. |
| 5,780,708 A | 7/1998 | Lundquist et al. |
| 5,804,425 A | 9/1998 | Barry et al. |
| 5,824,877 A | 10/1998 | Hinchee et al. |
| 5,837,848 A | 11/1998 | Ely et al. |
| 5,859,347 A | 1/1999 | Brown et al. |
| 5,866,775 A | 2/1999 | Eichholtz et al. |
| 5,874,265 A | 2/1999 | Adams et al. |
| 5,879,903 A | 3/1999 | Strauch et al. |
| 5,898,031 A | 4/1999 | Crooke |
| 5,914,451 A | 6/1999 | Martinell et al. |
| 5,919,675 A | 7/1999 | Adams et al. |
| 5,928,937 A | 7/1999 | Kakefuda et al. |
| 5,939,602 A | 8/1999 | Volrath et al. |
| 5,969,213 A | 10/1999 | Adams et al. |
| 5,981,840 A | 11/1999 | Zhao et al. |
| 5,985,793 A | 11/1999 | Sandbrink et al. |
| RE36,449 E | 12/1999 | Lebrun et al. |
| 6,040,497 A | 3/2000 | Spencer et al. |
| 6,056,938 A | 5/2000 | Unger et al. |
| 6,069,115 A | 5/2000 | Pallett et al. |
| 6,084,089 A | 7/2000 | Mine et al. |
| 6,084,155 A | 7/2000 | Volrath et al. |
| 6,107,094 A | 8/2000 | Crooke |
| 6,118,047 A | 9/2000 | Anderson et al. |
| 6,121,513 A | 9/2000 | Zhang et al. |
| 6,130,366 A | 10/2000 | Herrera-Estrella et al. |
| 6,140,078 A | 10/2000 | Sanders et al. |
| 6,153,812 A | 11/2000 | Fry et al. |
| 6,160,208 A | 12/2000 | Lundquist et al. |
| 6,177,616 B1 | 1/2001 | Bartsch et al. |
| 6,194,636 B1 | 2/2001 | McElroy et al. |
| 6,225,105 B1 | 5/2001 | Sathasivan et al. |
| 6,225,114 B1 | 5/2001 | Eichholtz et al. |
| 6,232,526 B1 | 5/2001 | McElroy et al. |
| 6,232,536 B1 | 5/2001 | McElroy et al. |
| 6,245,968 B1 | 6/2001 | Boudec et al. |
| 6,248,876 B1 | 6/2001 | Barry et al. |
| 6,252,138 B1 | 6/2001 | Karimi et al. |
| RE37,287 E | 7/2001 | Lebrun et al. |
| 6,268,549 B1 | 7/2001 | Sailland et al. |
| 6,271,359 B1 | 8/2001 | Norris et al. |
| 6,282,837 B1 | 9/2001 | Ward et al. |
| 6,288,306 B1 | 9/2001 | Ward et al. |
| 6,288,312 B1 | 9/2001 | Christou et al. |
| 6,294,714 B1 | 9/2001 | Matsunaga et al. |
| 6,303,374 B1 | 10/2001 | Zhang et al. |
| 6,326,193 B1 | 12/2001 | Liu et al. |

(56) References Cited

U.S. PATENT DOCUMENTS

| | | |
|---|---|---|
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,421,956 B1 | 7/2002 | Boukens et al. |
| 6,426,446 B1 | 7/2002 | McElroy et al. |
| 6,433,252 B1 | 8/2002 | Kriz et al. |
| 6,437,217 B1 | 8/2002 | McElroy et al. |
| 6,453,609 B1 | 9/2002 | Soll et al. |
| 6,479,291 B2 | 11/2002 | Kumagai et al. |
| 6,506,559 B1 | 1/2003 | Fire et al. |
| 6,642,435 B1 | 11/2003 | Rafalski et al. |
| 6,644,341 B1 | 11/2003 | Chemo et al. |
| 6,645,914 B1 | 11/2003 | Woznica et al. |
| 6,768,044 B1 | 7/2004 | Boudec et al. |
| 6,843,985 B2 | 1/2005 | Erickson, Jr. et al. |
| 6,992,237 B1 | 1/2006 | Habben et al. |
| 7,022,896 B1 | 4/2006 | Weeks et al. |
| 7,026,528 B2 | 4/2006 | Cheng et al. |
| 7,056,704 B2 | 6/2006 | Tuschl et al. |
| 7,078,196 B2 | 7/2006 | Tuschl et al. |
| RE39,247 E | 8/2006 | Barry et al. |
| 7,105,724 B2 | 9/2006 | Weeks et al. |
| 7,297,541 B2 | 11/2007 | Moshiri et al. |
| 7,304,209 B2 | 12/2007 | Zink et al. |
| 7,312,379 B2 | 12/2007 | Andrews et al. |
| 7,323,310 B2 | 1/2008 | Peters et al. |
| 7,371,927 B2 | 5/2008 | Yao et al. |
| 7,392,379 B2 | 6/2008 | Le Pennec et al. |
| 7,405,347 B2 | 7/2008 | Hammer et al. |
| 7,406,981 B2 | 8/2008 | Hemo et al. |
| 7,462,379 B2 | 12/2008 | Fukuda et al. |
| 7,485,777 B2 | 2/2009 | Nakaj Ima et al. |
| 7,525,013 B2 | 4/2009 | Hildebrand et al. |
| 7,550,578 B2 | 6/2009 | Budworth et al. |
| 7,622,301 B2 | 11/2009 | Ren et al. |
| 7,657,299 B2 | 2/2010 | Huizenga et al. |
| 7,671,254 B2 | 3/2010 | Tranel et al. |
| 7,714,188 B2 | 5/2010 | Castle et al. |
| 7,738,626 B2 | 6/2010 | Weese et al. |
| 7,807,791 B2 | 10/2010 | Sekar et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,855,323 B2 | 12/2010 | Huang et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,090,164 B2 | 1/2012 | Bullitt et al. |
| 8,097,712 B2* | 1/2012 | Paldi et al. .................. 536/23.1 |
| 8,143,480 B2 | 3/2012 | Axtell et al. |
| 8,158,414 B2 | 4/2012 | Rommens et al. |
| 8,507,457 B2 | 8/2013 | Paldi et al. |
| 8,548,778 B1 | 10/2013 | Hart et al. |
| 8,554,490 B2 | 10/2013 | Tang et al. |
| 8,598,332 B1 | 12/2013 | Waterhouse et al. |
| 9,006,414 B2 | 4/2015 | Huang et al. |
| 9,121,022 B2 | 9/2015 | Sammons et al. |
| 9,422,557 B2 | 8/2016 | Ader |
| 9,445,603 B2 | 9/2016 | Baum et al. |
| 10,100,306 B2 | 10/2018 | Inberg et al. |
| 2001/0006797 A1 | 7/2001 | Kumagai et al. |
| 2001/0042257 A1 | 11/2001 | Connor-Ward et al. |
| 2002/0069430 A1 | 6/2002 | Kiaska et al. |
| 2002/0086356 A1 | 7/2002 | Tuschl et al. |
| 2002/0114784 A1 | 8/2002 | Li et al. |
| 2003/0017068 A1 | 1/2003 | Larrain et al. |
| 2003/0044443 A1 | 3/2003 | Erickson, Jr. et al. |
| 2003/0092651 A1 | 5/2003 | Norris et al. |
| 2003/0140371 A1* | 7/2003 | Stevens ................. A01N 37/44 800/279 |
| 2003/0154508 A1 | 8/2003 | Stevens et al. |
| 2003/0167537 A1 | 9/2003 | Jiang |
| 2003/0180945 A1 | 9/2003 | Wang et al. |
| 2004/0029275 A1 | 2/2004 | Brown et al. |
| 2004/0053289 A1 | 3/2004 | Allen et al. |
| 2004/0055041 A1 | 3/2004 | Labate et al. |
| 2004/0072692 A1 | 4/2004 | Hoffman et al. |
| 2004/0082475 A1 | 4/2004 | Hoffman et al. |
| 2004/0123347 A1 | 6/2004 | Hinchey et al. |
| 2004/0126845 A1 | 7/2004 | Eenennaam et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0216189 A1 | 10/2004 | Houmard et al. |
| 2004/0244075 A1 | 12/2004 | Cai et al. |
| 2004/0250310 A1 | 12/2004 | Shukla et al. |
| 2004/0259247 A1 | 12/2004 | Tuschl et al. |
| 2005/0005319 A1 | 1/2005 | Della-Cioppa et al. |
| 2005/0044591 A1 | 2/2005 | Yao et al. |
| 2005/0080032 A1* | 4/2005 | Gross et al. .................... 514/44 |
| 2005/0095199 A1* | 5/2005 | Whyard et al. ................. 424/9.2 |
| 2005/0215435 A1 | 9/2005 | Menges et al. |
| 2005/0250647 A1 | 11/2005 | Hills et al. |
| 2006/0009358 A1 | 1/2006 | Kibler et al. |
| 2006/0021087 A1 | 1/2006 | Baum et al. |
| 2006/0040826 A1 | 2/2006 | Eaton et al. |
| 2006/0111241 A1 | 5/2006 | Gerwick, III et al. |
| 2006/0130172 A1 | 6/2006 | Whaley et al. |
| 2006/0135758 A1 | 6/2006 | Wu |
| 2006/0200878 A1 | 9/2006 | Lutfiyya et al. |
| 2006/0223708 A1 | 10/2006 | Hoffman et al. |
| 2006/0223709 A1 | 10/2006 | Helmke et al. |
| 2006/0247197 A1 | 11/2006 | Van De Craen et al. |
| 2006/0272049 A1 | 11/2006 | Waterhouse et al. |
| 2006/0276339 A1 | 12/2006 | Windsor et al. |
| 2007/0011448 A1 | 1/2007 | Chhabra et al. |
| 2007/0011775 A1 | 1/2007 | Allen et al. |
| 2007/0021360 A1 | 1/2007 | Nyce et al. |
| 2007/0026765 A1 | 2/2007 | Renn |
| 2007/0050860 A1 | 3/2007 | Andersen et al. |
| 2007/0050863 A1 | 3/2007 | Tranel et al. |
| 2007/0124836 A1 | 5/2007 | Baum et al. |
| 2007/0199095 A1 | 8/2007 | Allen et al. |
| 2007/0219151 A1 | 9/2007 | Satishchandran et al. |
| 2007/0232188 A1* | 10/2007 | Probasco .......................... 449/1 |
| 2007/0259785 A1 | 11/2007 | Heck et al. |
| 2007/0269815 A1 | 11/2007 | Rivory et al. |
| 2007/0281900 A1 | 12/2007 | Cui et al. |
| 2007/0300329 A1 | 12/2007 | Allen et al. |
| 2008/0022423 A1 | 1/2008 | Roberts et al. |
| 2008/0050342 A1 | 2/2008 | Fire et al. |
| 2008/0092256 A1 | 4/2008 | Kohn |
| 2008/0113351 A1 | 5/2008 | Naito et al. |
| 2008/0155716 A1 | 6/2008 | Sonnewald et al. |
| 2008/0194512 A1 | 8/2008 | John et al. |
| 2008/0214443 A1 | 9/2008 | Baum et al. |
| 2008/0261303 A1 | 10/2008 | Kreutzer et al. |
| 2009/0011934 A1 | 1/2009 | Zawierucha et al. |
| 2009/0018016 A1 | 1/2009 | Duck et al. |
| 2009/0036311 A1 | 2/2009 | Witschel et al. |
| 2009/0054240 A1 | 2/2009 | Witschel et al. |
| 2009/0075921 A1 | 3/2009 | Ikegawa et al. |
| 2009/0098614 A1 | 4/2009 | Zamore et al. |
| 2009/0118214 A1 | 5/2009 | Paldi et al. |
| 2009/0137395 A1 | 5/2009 | Chicoine et al. |
| 2009/0165153 A1 | 6/2009 | Wang et al. |
| 2009/0165166 A1 | 6/2009 | Feng et al. |
| 2009/0172838 A1 | 7/2009 | Axtell et al. |
| 2009/0188005 A1 | 7/2009 | Boukharov et al. |
| 2009/0205079 A1 | 8/2009 | Kumar et al. |
| 2009/0215628 A1 | 8/2009 | Witschel et al. |
| 2009/0285784 A1 | 11/2009 | Raemaekers et al. |
| 2009/0293148 A1 | 11/2009 | Ren et al. |
| 2009/0298787 A1 | 12/2009 | Raemaekers et al. |
| 2009/0306189 A1 | 12/2009 | Raemaekers et al. |
| 2010/0005551 A1 | 1/2010 | Roberts et al. |
| 2010/0048670 A1 | 2/2010 | Biard et al. |

(56) References Cited

U.S. PATENT DOCUMENTS

| | | |
|---|---|---|
| 2010/0068172 A1 | 3/2010 | Van De Craen |
| 2010/0071088 A1 | 3/2010 | Sela et al. |
| 2010/0099561 A1 | 4/2010 | Selby et al. |
| 2010/0100988 A1 | 4/2010 | Tranel et al. |
| 2010/0152443 A1 | 6/2010 | Hirai et al. |
| 2010/0154083 A1 | 6/2010 | Ross et al. |
| 2010/0192237 A1 | 7/2010 | Ren et al. |
| 2010/0247578 A1 | 9/2010 | Salama |
| 2011/0015084 A1 | 1/2011 | Christian et al. |
| 2011/0015284 A1 | 1/2011 | Dees et al. |
| 2011/0028412 A1 | 2/2011 | Cappello et al. |
| 2011/0035836 A1 | 2/2011 | Eudes et al. |
| 2011/0041400 A1 | 2/2011 | Trias Vila et al. |
| 2011/0053226 A1 | 3/2011 | Rohayem |
| 2011/0098180 A1 | 4/2011 | Michel et al. |
| 2011/0105327 A1 | 5/2011 | Nelson |
| 2011/0105329 A1 | 5/2011 | Song et al. |
| 2011/0112570 A1 | 5/2011 | Mannava et al. |
| 2011/0126310 A1 | 5/2011 | Feng et al. |
| 2011/0126311 A1 | 5/2011 | Velcheva et al. |
| 2011/0152339 A1 | 6/2011 | Brown et al. |
| 2011/0152346 A1 | 6/2011 | Karleson et al. |
| 2011/0152353 A1 | 6/2011 | Koizumi et al. |
| 2011/0160082 A1 | 6/2011 | Woo et al. |
| 2011/0166022 A1 | 7/2011 | Israels et al. |
| 2011/0166023 A1 | 7/2011 | Nettleton-Hammond et al. |
| 2011/0171176 A1 | 7/2011 | Baas et al. |
| 2011/0171287 A1 | 7/2011 | Saarma et al. |
| 2011/0177949 A1 | 7/2011 | Krapp et al. |
| 2011/0185444 A1 | 7/2011 | Li et al. |
| 2011/0185445 A1 | 7/2011 | Bogner et al. |
| 2011/0191897 A1 | 8/2011 | Force et al. |
| 2011/0201501 A1 | 8/2011 | Song et al. |
| 2011/0296555 A1 | 12/2011 | Ivashuta et al. |
| 2011/0296556 A1 | 12/2011 | Sammons et al. |
| 2012/0036594 A1 | 2/2012 | Cardoza et al. |
| 2012/0053231 A1 | 3/2012 | Paldi et al. |
| 2012/0107355 A1 | 5/2012 | Harris et al. |
| 2012/0108497 A1 | 5/2012 | Paldi et al. |
| 2012/0128218 A1 | 5/2012 | Amyot et al. |
| 2012/0137387 A1 | 5/2012 | Baum et al. |
| 2012/0150048 A1 | 6/2012 | Kang et al. |
| 2012/0156784 A1 | 6/2012 | Adams, Jr. et al. |
| 2012/0157512 A1 | 6/2012 | Ben-Chanoch et al. |
| 2012/0164205 A1 | 6/2012 | Baum et al. |
| 2012/0185967 A1 | 7/2012 | Sela et al. |
| 2012/0198586 A1 | 8/2012 | Narva et al. |
| 2012/0230565 A1 | 9/2012 | Steinberg et al. |
| 2012/0258646 A1 | 10/2012 | Sela et al. |
| 2012/0297501 A1 | 11/2012 | Beghyn et al. |
| 2012/0316220 A1 | 12/2012 | Ward et al. |
| 2013/0003213 A1 | 1/2013 | Kabelac et al. |
| 2013/0041004 A1 | 2/2013 | Drager et al. |
| 2013/0047297 A1 | 2/2013 | Sammons et al. |
| 2013/0047298 A1 | 2/2013 | Tang |
| 2013/0058890 A1 | 3/2013 | Raemaekers et al. |
| 2013/0060133 A1 | 3/2013 | Kassab et al. |
| 2013/0067618 A1 | 3/2013 | Ader et al. |
| 2013/0084243 A1 | 4/2013 | Goetsch et al. |
| 2013/0096073 A1 | 4/2013 | Sidelman |
| 2013/0097726 A1 | 4/2013 | Ader et al. |
| 2013/0212739 A1 | 8/2013 | Giritch et al. |
| 2013/0226003 A1 | 8/2013 | Edic et al. |
| 2013/0232646 A1 | 9/2013 | Baum et al. |
| 2013/0247247 A1 | 9/2013 | Ader et al. |
| 2013/0254940 A1 | 9/2013 | Ader et al. |
| 2013/0254941 A1 | 9/2013 | Ader et al. |
| 2013/0288895 A1 | 10/2013 | Ader et al. |
| 2013/0289097 A1 | 10/2013 | Paldi et al. |
| 2013/0318657 A1 | 11/2013 | Avniel et al. |
| 2013/0318658 A1 | 11/2013 | Ader et al. |
| 2013/0324842 A1 | 12/2013 | Mittal et al. |
| 2013/0326731 A1 | 12/2013 | Ader et al. |
| 2014/0018241 A1 | 1/2014 | Sammons et al. |
| 2014/0057789 A1 | 2/2014 | Sammons et al. |
| 2014/0109258 A1 | 4/2014 | Van De Craen et al. |
| 2014/0230090 A1 | 8/2014 | Avniel et al. |
| 2014/0274712 A1 | 9/2014 | Finnessy et al. |
| 2014/0275208 A1 | 9/2014 | Hu et al. |
| 2014/0296503 A1 | 10/2014 | Avniel et al. |
| 2014/0371298 A1 | 12/2014 | Paldi et al. |
| 2015/0096079 A1 | 4/2015 | Avniel et al. |
| 2015/0143580 A1 | 5/2015 | Beattie et al. |
| 2015/0159156 A1 | 6/2015 | Inberg et al. |
| 2015/0203867 A1 | 7/2015 | Beattie et al. |
| 2015/0240258 A1 | 8/2015 | Beattie et al. |
| 2016/0015035 A1 | 1/2016 | Tao |
| 2016/0029644 A1 | 2/2016 | Tao |
| 2017/0037407 A1 | 2/2017 | Gleit-Kielmanowicz et al. |
| 2017/0088838 A1 | 3/2017 | Inberg et al. |
| 2017/0183683 A1 | 6/2017 | Zheng et al. |
| 2017/0260522 A1 | 9/2017 | Zheng et al. |

FOREIGN PATENT DOCUMENTS

| | | |
|---|---|---|
| CA | 2806295 | 2/2011 |
| CN | 1505504 | 6/2004 |
| CN | 101139607 | 3/2008 |
| CN | 101279950 | 10/2008 |
| CN | 101279951 | 10/2008 |
| CN | 101914540 | 12/2010 |
| CN | 102822350 | 12/2012 |
| CN | 105849266 | 8/2016 |
| DE | 288618 | 4/1991 |
| DE | 10000600 | 7/2001 |
| DE | 10116399 | 10/2002 |
| DE | 10256353 | 6/2003 |
| DE | 10256354 | 6/2003 |
| DE | 10256367 | 6/2003 |
| DE | 10204951 | 8/2003 |
| DE | 10234875 | 2/2004 |
| DE | 10234876 | 2/2004 |
| DE | 102004054666 | 5/2006 |
| DE | 102005014638 | 10/2006 |
| DE | 102005014906 | 10/2006 |
| DE | 102007012168 | 9/2008 |
| DE | 102010042866 | 5/2011 |
| EP | 0 375 408 | 6/1990 |
| EP | 0 804 600 | 11/1997 |
| EP | 1 157 991 | 11/2001 |
| EP | 1 238 586 | 9/2002 |
| EP | 1416049 | 5/2004 |
| EP | 2 147 919 | 1/2010 |
| EP | 2 160 098 | 11/2010 |
| EP | 2 530 159 | 3/2011 |
| EP | 2 305 813 | 4/2011 |
| EP | 2 545 182 | 1/2013 |
| EP | 2703489 | 3/2014 |
| EP | 2703490 | 3/2014 |
| EP | 2706114 | 3/2014 |
| EP | 3 066 200 | 9/2016 |
| JP | 2001253874 | 9/2001 |
| JP | 2002080454 | 3/2002 |
| JP | 2002138075 | 5/2002 |
| JP | 2002145707 | 5/2002 |
| JP | 2002220389 | 8/2002 |
| JP | 2003064059 | 3/2003 |
| JP | 2003096059 | 4/2003 |
| JP | 2004051628 | 2/2004 |
| JP | 2004107228 | 4/2004 |
| JP | 2005008583 | 1/2005 |
| JP | 2005239675 | 9/2005 |
| JP | 2005314407 | 11/2005 |
| JP | 2006232824 | 9/2006 |
| JP | 2006282552 | 10/2006 |
| JP | 2007153847 | 6/2007 |
| JP | 2007161701 | 6/2007 |
| JP | 2007182404 | 7/2007 |
| JP | 2008074840 | 4/2008 |
| JP | 2008074841 | 4/2008 |
| JP | 2008133207 | 6/2008 |
| JP | 2008133218 | 6/2008 |
| JP | 2008169121 | 7/2008 |
| JP | 2009-508481 | 3/2009 |

(56) References Cited

FOREIGN PATENT DOCUMENTS

| | | |
|---|---|---|
| JP | 2009067739 | 4/2009 |
| JP | 2009114128 | 5/2009 |
| JP | 2009126792 | 6/2009 |
| JP | 2009137851 | 6/2009 |
| WO | WO 89/11789 | 12/1989 |
| WO | WO 95/34659 | 12/1995 |
| WO | WO 95/34668 | 12/1995 |
| WO | WO 96/005721 | 2/1996 |
| WO | WO 96/033270 | 10/1996 |
| WO | WO 96/038567 | 12/1996 |
| WO | WO 96/040964 | 12/1996 |
| WO | WO 97/47193 | 12/1997 |
| WO | WO 97/49816 | 12/1997 |
| WO | WO 99/024585 | 5/1999 |
| WO | WO 99/26467 | 6/1999 |
| WO | WO 99/27116 | 6/1999 |
| WO | WO 99/32619 | 7/1999 |
| WO | WO 99/61631 | 12/1999 |
| WO | WO 99/67367 | 12/1999 |
| WO | WO 00/04176 | 1/2000 |
| WO | WO 00/32757 | 6/2000 |
| WO | WO 00/034035 | 6/2000 |
| WO | WO 00/044914 | 8/2000 |
| WO | WO 01/07601 | 2/2001 |
| WO | WO 01/34815 | 5/2001 |
| WO | WO 2001/085970 | 11/2001 |
| WO | WO 02/14472 | 2/2002 |
| WO | WO 02/066660 | 8/2002 |
| WO | WO 03/000679 | 1/2003 |
| WO | WO 03/004649 | 1/2003 |
| WO | WO 03/006422 | 1/2003 |
| WO | WO 03/012052 | 2/2003 |
| WO | WO 03/013247 | 2/2003 |
| WO | WO 03/016308 | 2/2003 |
| WO | WO 2003/014357 | 2/2003 |
| WO | WO 03/020704 | 3/2003 |
| WO | WO 03/022051 | 3/2003 |
| WO | WO 03/022831 | 3/2003 |
| WO | WO 03/022843 | 3/2003 |
| WO | WO 03/029243 | 4/2003 |
| WO | WO 03/037085 | 5/2003 |
| WO | WO 03/037878 | 5/2003 |
| WO | WO 03/045878 | 6/2003 |
| WO | WO 03/050087 | 6/2003 |
| WO | WO 03/051823 | 6/2003 |
| WO | WO 03/051824 | 6/2003 |
| WO | WO 03/051846 | 6/2003 |
| WO | WO 03/064625 | 8/2003 |
| WO | WO 03/076409 | 9/2003 |
| WO | WO 03/077648 | 9/2003 |
| WO | WO 03/087067 | 10/2003 |
| WO | WO 03/090539 | 11/2003 |
| WO | WO 03/091217 | 11/2003 |
| WO | WO 03/093269 | 11/2003 |
| WO | WO 03/104206 | 12/2003 |
| WO | WO 2004/002947 | 1/2004 |
| WO | WO 2004/002981 | 1/2004 |
| WO | WO 2004/005485 | 1/2004 |
| WO | WO 2004/009761 | 1/2004 |
| WO | WO 2004/011429 | 2/2004 |
| WO | WO 2004/022771 | 3/2004 |
| WO | WO 2004/029060 | 4/2004 |
| WO | WO 2004/035545 | 4/2004 |
| WO | WO 2004/035563 | 4/2004 |
| WO | WO 2004/035564 | 4/2004 |
| WO | WO 2004/037787 | 5/2004 |
| WO | WO 2004/049806 | 6/2004 |
| WO | WO 2004/062351 | 7/2004 |
| WO | WO 2004/067518 | 8/2004 |
| WO | WO 2004/067527 | 8/2004 |
| WO | WO 2004/074443 | 9/2004 |
| WO | WO 2004/077950 | 9/2004 |
| WO | WO 2005/000824 | 1/2005 |
| WO | WO 2005/003362 | 1/2005 |
| WO | WO 2005/007627 | 1/2005 |
| WO | WO 2005/007860 | 1/2005 |
| WO | WO 2005/040152 | 5/2005 |
| WO | WO 2005/047233 | 5/2005 |
| WO | WO 2005/047281 | 5/2005 |
| WO | WO 2005/061443 | 7/2005 |
| WO | WO 2005/061464 | 7/2005 |
| WO | WO 2005/068434 | 7/2005 |
| WO | WO 2005/070889 | 8/2005 |
| WO | WO 2005/089551 | 9/2005 |
| WO | WO 2005/095335 | 10/2005 |
| WO | WO 2005/107437 | 11/2005 |
| WO | WO 2005/110068 | 11/2005 |
| WO | WO 2006/006569 | 1/2006 |
| WO | WO 2006/024820 | 3/2006 |
| WO | WO 2006/029828 | 3/2006 |
| WO | WO 2006/029829 | 3/2006 |
| WO | WO 2006/037945 | 4/2006 |
| WO | WO 2006/050803 | 5/2006 |
| WO | WO 2006/074400 | 7/2006 |
| WO | WO 2006/090792 | 8/2006 |
| WO | WO 2006/123088 | 11/2006 |
| WO | WO 2006/125687 | 11/2006 |
| WO | WO 2006/125688 | 11/2006 |
| WO | WO 2006/138638 | 12/2006 |
| WO | WO 2007/003294 | 1/2007 |
| WO | WO 2007/007316 | 1/2007 |
| WO | WO 2007/024783 | 3/2007 |
| WO | WO 2007/026834 | 3/2007 |
| WO | WO 2007/035650 | 3/2007 |
| WO | WO 2007/038788 | 4/2007 |
| WO | WO 2007/039454 | 4/2007 |
| WO | WO 2007/050715 | 5/2007 |
| WO | WO 2007/070389 | 6/2007 |
| WO | WO 2007/071900 | 6/2007 |
| WO | WO 2007/074405 | 7/2007 |
| WO | WO 2007/074976 | 7/2007 |
| WO | WO 2007/077201 | 7/2007 |
| WO | WO 2007/077247 | 7/2007 |
| WO | WO 2007/083193 | 7/2007 |
| WO | WO 2007/096576 | 8/2007 |
| WO | WO 2007/119434 | 10/2007 |
| WO | WO 2007/134984 | 11/2007 |
| WO | WO 2008/007100 | 1/2008 |
| WO | WO 2008/009908 | 1/2008 |
| WO | WO 2008/029084 | 3/2008 |
| WO | WO 2008/042231 | 4/2008 |
| WO | WO 2008/059948 | 5/2008 |
| WO | WO 2008/063203 | 5/2008 |
| WO | WO 2008/071918 | 6/2008 |
| WO | WO 2008/074991 | 6/2008 |
| WO | WO 2008/084073 | 7/2008 |
| WO | WO 2008/100426 | 8/2008 |
| WO | WO 2008/102908 | 8/2008 |
| WO | WO 2008/148223 | 12/2008 |
| WO | WO 2008/152072 | 12/2008 |
| WO | WO 2008/152073 | 12/2008 |
| WO | WO 2009/000757 | 12/2008 |
| WO | WO 2009/005297 | 1/2009 |
| WO | WO 2009/029690 | 3/2009 |
| WO | WO 2009/035150 | 3/2009 |
| WO | WO 2009/037329 | 3/2009 |
| WO | WO 2009/046384 | 4/2009 |
| WO | WO 2009/060429 | 5/2009 |
| WO | WO 2009/063180 | 5/2009 |
| WO | WO 2009/068170 | 6/2009 |
| WO | WO 2009/068171 | 6/2009 |
| WO | WO 2009/086041 | 7/2009 |
| WO | WO 2009/090402 | 7/2009 |
| WO | WO 2009/091862 | 7/2009 |
| WO | WO 2009/091863 | 7/2009 |
| WO | WO 2009/115788 | 9/2009 |
| WO | WO 2009/116558 | 9/2009 |
| WO | WO 2009/125401 | 10/2009 |
| WO | WO 2009/152995 | 12/2009 |
| WO | WO 2009/158258 | 12/2009 |
| WO | WO 2010/012649 | 2/2010 |
| WO | WO 2010/026989 | 3/2010 |
| WO | WO 2010/034153 | 4/2010 |
| WO | WO 2010/049270 | 5/2010 |

(56) References Cited

FOREIGN PATENT DOCUMENTS

| WO | WO 2010/049369 | 5/2010 |
|---|---|---|
| WO | WO 2010/049405 | 5/2010 |
| WO | WO 2010/049414 | 5/2010 |
| WO | WO 2010/056519 | 5/2010 |
| WO | WO 2010/063422 | 6/2010 |
| WO | WO 2010/069802 | 6/2010 |
| WO | WO 2010/078906 | 7/2010 |
| WO | WO 2010/078912 | 7/2010 |
| WO | WO 2010/093788 | 8/2010 |
| WO | WO 2010/104217 | 9/2010 |
| WO | WO 2010/108611 | 9/2010 |
| WO | WO 2010/112826 | 10/2010 |
| WO | WO 2010/116122 | 10/2010 |
| WO | WO 2010/119906 | 10/2010 |
| WO | WO 2010/128465 | 11/2010 |
| WO | WO 2010/130970 | 11/2010 |
| WO | WO 2011/001434 | 1/2011 |
| WO | WO 2011/003776 | 1/2011 |
| WO | WO 2011/021171 | 2/2011 |
| WO | WO 2011/035874 | 3/2011 |
| WO | WO 2011/045796 | 4/2011 |
| WO | WO 2011/065451 | 6/2011 |
| WO | WO 2011/067745 | 6/2011 |
| WO | WO 2011/075188 | 6/2011 |
| WO | WO 2011/080674 | 7/2011 |
| WO | WO 2011/112570 | 9/2011 |
| WO | WO 2011/132127 | 10/2011 |
| WO | WO 2012/001626 | 1/2012 |
| WO | WO 2012/056401 | 5/2012 |
| WO | WO 2012/092580 | 7/2012 |
| WO | WO 2012/164100 | 12/2012 |
| WO | WO 2013/010691 | 1/2013 |
| WO | WO 2013/025670 | 2/2013 |
| WO | WO 2013/039990 | 3/2013 |
| WO | WO 2013/040005 | 3/2013 |
| WO | WO 2013/040021 | 3/2013 |
| WO | WO 2013/040033 | 3/2013 |
| WO | WO 2013/040049 | 3/2013 |
| WO | WO 2013/040057 | 3/2013 |
| WO | WO 2013/040116 | 3/2013 |
| WO | WO 2013/040117 | 3/2013 |
| WO | WO 2013/153553 | 10/2013 |
| WO | WO 2013/175480 | 11/2013 |
| WO | WO 2014/022739 | 2/2014 |
| WO | WO 2014/106837 | 7/2014 |
| WO | WO 2014/106838 | 7/2014 |
| WO | WO 2014/151255 | 9/2014 |
| WO | WO 2014/164761 | 10/2014 |
| WO | WO 2014/164797 | 10/2014 |
| WO | WO 2015/001336 | 1/2015 |
| WO | WO 2015/010026 | 1/2015 |
| WO | WO 2016/018887 | 2/2016 |

OTHER PUBLICATIONS

Shen et al, Virology 342:141-149, 2005.*
Maori et al, Virology 362:342-349, 2007.*
Cox-Foster et al, Science 318:283-287, 2007.*
Soares et al, Insect Mol. Biol. 14(4):443-452, 2005.*
Turner et al, Insect Mol. Biol. 15(3):383-391, 2006.*
Araujo et al, Insect Biochem. Mol. Biol. 36:683-693, 2006.*
GenBank BankIt, https://www.ncbi.nlm.nih.gov/WebSub/?tool=genbank[Sep. 27, 2016 6:27:51 AM].*
Aronstein et al, J. Apicultural Res. 45(1):20-24, 2006.*
Aronstein et al, Apidologie 36:3-14, 2005.*
Amdam et al, BMC Biotechnol. 3(1):pp. 1-8, 2003.*
Patel et al, PLOS One 2(6):e509, pp. 1-7, available online Jun. 6, 2007.*
O'Riordan et al. "Inhibitor of Apoptosis (IAP) Proteins in Eukaryotic Evolution and Development: A Model of Thematic Conservation", Developmental Cell, 15(4): 497-508, Oct. 2008.
Advisory Action Before the Filing of an Appeal Brief dated Feb. 22, 2013 From the Re. U.S. Appl. No. 13/332,430.
Applicant-Initiated Interview Summary dated Mar. 5, 2013 From the Re. U.S. Appl. No. 13/332,430.
Communication Pursuant to Article 94(3) EPC dated Feb. 17, 2011 From the European Patent Office Re. Application No. 08847971.2.
Communication Pursuant to Article 94(3) EPC dated Jun. 29, 2012 From the European Patent Office Re. Application No. 08847971.2.
Communication Relating to the Results of the Partial International Search dated May 13, 2009 From the International Searching Authority Re.: Application No. PCT/IL2008/001440.
International Preliminary Report on Patentability dated Feb. 1, 2010 From the International Preliminary Examining Authority Re.: Application No. PCT/IL2008/001440.
International Preliminary Report on Patentability dated Mar. 1, 2010 From the International Bureau of WIPO Re. Application No. PCT/IB2010/053776.
International Preliminary Report on Patentability dated Nov. 17, 2011 From the International Bureau of WIPO Re. Application No. PCT/IB2010/051980.
International Preliminary Report on Patentability dated Apr. 26, 2012 From the International Bureau of WiIPO Re. Application No. PCT/IL2010/000844.
International Search Report and the Written Opinion dated Jul. 19, 2010 From the International Searching Authority Re.: Application No. PCT/IB2010/051980.
International Search Report and the Written Opinion dated Feb. 24, 2011 From the International Searching Authority Re. Application No. PCT/IL2010/000844.
International Search Report and the Written Opinion dated Nov. 30, 2010 From the International Searching Authority Re. Application No. PCT/IB2010/053776.
International Search Report dated Aug. 13, 2009 From the International Searching Authority Re.: Application No. PCT/IL2008/001440.
Notice of Allowance dated Sep. 9, 2011 From the Re. U.S. Appl. No. 12/222,949.
Notice of Allowance dated Apr. 11, 2013 From the Re. U.S. Appl. No. 13/332,430.
Office Action dated Mar. 19, 2012 From the Israel Patent Office Re. Application No. 205594 and Its Translation Into English.
Official Action dated Jan. 7, 2013 From the Re. U.S. Appl. No. 13/318,636.
Official Action dated Oct. 15, 2012 From the Re. U.S. Appl. No. 13/332,430.
Official Action dated Mar. 18, 2011 From the Re. U.S. Appl. No. 12/222,949.
Official Action dated Sep. 23, 2010 From the Re. U.S. Appl. No. 12/222,949.
Official Action dated Jun. 28, 2010 From the Re. U.S. Appl. No. 12/222,949.
Official Action dated May 30, 2012 From the Re. U.S. Appl. No. 13/332,430.
Response dated Jun. 15, 2011 to Communication Pursuant to Article 94(3) EPC of Feb. 17, 2011 From the European Patent Office Re. Application No. 08847971.2.
Response dated Jul. 18, 2011 to Official Action dated Mar. 18, 2011 From the Re. U.S. Appl. No. 12/222,949.
Response dated Jan. 20, 2011 to Official Action dated Sep. 23, 2010 From the Re. U.S. Appl. No. 12/222,949.
Response dated Jul. 27, 2010 to Official Action dated Jun. 28, 2010 From the Re. U.S. Appl. No. 12/222,949.
Restriction Official Action dated Nov. 21, 2012 From the Re. U.S. Appl. No. 13/318,636.
Written Opinion dated Aug. 13, 2009 From the International Searching Authority Re.: Application No. PCT/IL2008/001440.
Akiyoshi et al. "Genomic Survey of the Non-Cultivatable Opportunistic Human Pathogen, Enterocytozoon Bieneusi", PLoS Pathogens, 5(1): e1000261: 1-10, Jan. 2009.
Amdam et al. "The Hive Bee to Forager Transition in Honeybee Colonies: The Double Repressor Hypothesis", Journal of Theoretical Biology, 223: 451-464, 2003.
Ananthaswamy "Can the ISPs Bear the Peer-to-Peer Explosion?", NewScientist, 2 P., Oct. 13, 2007.

(56) References Cited

OTHER PUBLICATIONS

Aronstein et al. "SID-I is Implicated in Systemic Gene Silencing in the Honey Bee", Journal of Agricultural Research and Bee World, XP009115329, 45(1): 20-24, Jan. 2006.
Baum et al. "Control of Coleopteran Insect Pests Through RNA Interference", Nature Biotechnology, 25(11): 1322-1326, Nov. 2007, Advance Online Publication, Nov. 4, 2007.
Burri et al. "Microsporidian Mitosomes Retain Elements of the General Mitochondrial Targeting System", Proc. Natl. Acad. Sci. USA, 103(43): 15916-15920, Oct. 24, 2006.
Campbell et al. "Gene-Knockdown in the Honey Bee Mite Varroa Destructor by a Non-Invasive Approach: Studies on A Glutathione S-Transferase", Parasites & Vectors, XP002621493, 3(73): 1-10, Aug. 16, 2010. Abstract.
Carthew "Gene Silencing by Double-Stranded RNA", Current Opinion in Cell Biology, XP002263320, 13: 244-248, 2001.
Chen et al. "High Throughput Genome-Wide Survey of Small RNAs From the Parasitic Protists Giardia Intestinalis and Trichomonas Vaginalis", Genome, Biology and Evolution, p.165-175, Jul. 6, 2009.
Chen et al. "Nosema Ceranae is a Long-Present and Wide-Spread Microsporidian Infection of the European Honey Bee (*Apis mellifera*) in the United States", Journal of Invertebrate Pathology, XP022438643, 97(2): 186-188, Jan. 29, 2008.
Computer Associates International "eTrust™ Content Inspection™. Malicious Code Protection", Computer Associates International Inc., 2 P., 2000.
Common et al. "Genomic Analyses of the Microsporidian Nosema Ceranae, An Emergent Pathogen of Honey Bees", PLoS Pathogens, 5(6): e1000466: 1-14, Jun. 2009.
Cox-Foster et al. "A Metagenomic Survey of Microbes in Honey Bee Colony Collapse Disorder", Science, XP002533680, 318(5848): 283-287, Oct. 2007. Database EMBL [Online], Retrieved From EBI, Database Accession No. EU122366, Nov. 15, 2007.
Cox-Foster et al. "Saving the Honeybee. The Mysterious Ailment Called Colony Collapse Disorder Has Wiped Out Large Numbers of the Bees That Pollinate a Third of Our Crops", Scientific American, p. 40-47, Apr. 2009.
De La Fuente et al. "RNA Interference for the Study and Genetic Manipulation of Ticks", Trends in Parasitology, 23(9): 427-433, Sep. 2007. Abstract.
Di Prisco et al. "Varroa Destructor is an Effective Vector of Israeli Acute Paralysis Virus in the Honeybee, *Apis mellifera*", Journal of General Virology, 92: 151-155, 2011.
Fairbairn et al. "Host-Delivered RNAi: An Effective Strategy to Silence Genes in Plant Parasitic Nematodes", Planta, 226(6): 1525-1533, Nov. 2007. Abstract.
Franco Nunes et al. "A Non-Invasive Method for Silencing Gene Transcription in Honeybees Maintained Under Natural Conditions", Insect Biochemistry and Molecular Biology, XP002523702, 39(2): 157-160, Feb. 2009.
Gill et al. "Stripped-Down DNA Repair in a High Reduced Parasite", BMC Molecular Biology, 8(24): 1-14, Mar. 20, 2007.
Henderson et al. "U.S. National Bee Colony Loss Survey, www.beesurvey.com, Preliminary Findings With Respect to Colony Collapse Disorder (CCD)", Bee Alert Technology, Inc., Mar. 26, 2007.
Hunter et al. "Large-Scale Field Application of RNAi Technology Reducing Israeli Acute Paralysis Virus Disease in Honey Bees (*Apis mellifera*, Hymenoptera: Apidae)", PLoS Pathogens, 6(12): e1001160-1-e1001160-10, Dec. 2010.
Katinka et al. "Genome Sequence and Gene Compaction of the Eukaryote Parasite Encephalitozoon Cuniculi", Nature, 414(6862): 450-453, Nov. 22, 2001. Abstract.
Liu et al. "Effect of a Fluvalinate-Resistance-Associated Sodium Chennel Mutation From Varroa Mites on Cockroach Sodium Channel Sensitivity to Fluvalinate, A Pyrethroid Insecticide", Insect Biochemistry and Molecular Biology, XP025014535, 36(11): 885-889, Nov. 1, 2006. Abstract.
Liu et al. "Prevention of Chinese Saebrood Virus Infection in Apis Cerana Using RNA Interference", Current Microbiology, 61(5): 422-428, Nov. 2010. Abstract.
Maggi et al. "Resistance Phenomena to Amitraz From Population of the Ectoparasitic Mite Varroa Destructor of Argentina", Parasitology Research, 107(5): 1189-1192, Oct. 2010. Abstract.
Malhotra et al. "Double-Stranded RNA-Mediated Gene Silencing of Cysteine Proteases (Falcipain-1 and -2) of Plasmodium Falciparum", Molecular Mcirobiology, 45(5): 1245-1254, 2002.
Malone et al. "Effects of Transgene Products on Honey Bees (*Apis mellifera*) and Bumblebees (*Bombus* Sp.)", Apidologie, XP009141014, 32(4): 287-304, Jul. 2001. p. 288, 1-h Col., § 3—p. 289, 1-h Col., § 2.
Maori et al. "IAPV, A Bee-Affecting Virus Associated With Colony Collapse Disorder Can Be Silenced by DsRNA Ingestion", Insect Molecular Biology, XP002523701, 18(1): 55-60, Feb. 2009. Abstract.
Maori et al. "Isolation and Characterization of Israeli Acute Paralysis Virus, A Dicistrovirus Affecting Honeybees in Israel: Evidence for Diversity Due to Intra-and Inter-Species Recombination", Journal of General Virology, XP002533679, 88(Part 12): 3428-3438, Dec. 2007. Database EMBL [Online], Retrieved From EBI, Database Accession No. EF219380, Nov. 21, 2007.
Maori et al. "Israel Acute Paralysis Virus of Bees, Complete Genome", GenBank EMBL, EBI Dbfetch, XP002533679, Accession No. EF219380, Nov. 21, 2007.
Maori et al. "Reciprocal Sequence Exchange Between Non-Retro Viruses and Hosts Leading to the Appearance of New Host Phenotypes", Virology, XP022065066, 362(2): 342-349, 2007.
Mayack et al. "Energetic Stress in the Honeybee *Apis mellifera* From Nosema Ceranae Infection", Journal of Invertebrate Pathology, 100(3): 185-188, Mar. 2009.
Mutti et al. "IRS and TOR Nutrient-Signaling Pathways Act Via Juvenile Hormone to Influence Honey Bee Caste Fate", Journal of Experimental Biology, 214(Pt.23): 3977-3984, Dec. 1, 2011. Abstract.
Nakayashiki et al. "Evolution and Diversification of RNA Silencing Proteins in Fungi", Journal of Molecular Evolution, 63(1): 127-135, Jul. 2006.
Nunes et al. "A Non-Invasive Method for Silencing Gene Transcription in Honeybees Maintained Under Natural Conditions", Insect Biochemistry and Molecular Biology, XP002523702, 39(2): 157-160, Feb. 1, 2009.
Palacios et al. "Genetic analysis of Israel Acute Paralysis Virus: Distinct Clusters Are Circulating in the United States", Journal of Virology, XP002533681, 82(13): 6209-6217, Jul. 2008. Database EMBL [Online], Retrieved From EBI, Database Accession No. EU436456, Jun. 19, 2008.
Paldi et al. "Effective Gene Silencing in a Microsporidian Parasite Associated With Honeybee (*Apis mellifera*) Colony Declines", Applied and Environmental Microbiology, 7607): 5960-5964, Sep. 2010.
Patel et al. "The Making of a Queen: TOR Pathway is a Key Player in Diphenic Caste Development.", PLoS ONE, 2(6): e509-1-e509-7, Jun. 2007.
Peyretaillade et al. "Microsporidian Encephalitozoon Cuniculi, A Unicellular Eukaryote With an Unusual Chromosomal Dispersion of Ribosomal Genes and a LSU rRNA Reduced to the Universal Core", Nucleic Acids Research, 26(15): 3513-3520, 1998.
Price et al. "RNAi-Mediated Crop Protection Against Insects", Trends in Biotechnology, XP022757296, 26(7): 393-400, Jul. 2008.
Radware "Content Inspection Director. Complete Content Security", Radware Ltd., www.radware.com, 2 P., 2004.
Radware "Content Inspection Director. High Speed Content Inspection", Radware Inc., p. 1-8, Sep. 18, 2002.
Radware "Radware Content Inspection Director (CID)—Symantec AntiVirus™ Gateway Solution", Radware Inc., www.radware.com, p. 1-4, Dec. 6, 2002.
Robalino et al. "Double-Stranded RNA and Antiviral Immunity in Marine Shrimp: Inducible Host Mechanisms and Evidence for the Evolution of Viral Counter-Responses", Developmental & Comparative Immunology, 31: 539-547, 2007.
Siomi et al. "On the Road to Reading the RNA-Interference Code", Nature, 457(7228): 396-404, Jan. 22, 2009. Abstract.

(56) References Cited

OTHER PUBLICATIONS

Slamovits et al. "Genome Compaction and Stability in Microsporidian Intracellular Parasites", Current Biology, 14(10): 891-896, May 25, 2004.
Standifer "Honey Bee Nutrition and Supplemental Feeding", Beekeeping in the United States Agriculture Handbook, 335: 39-45, Oct. 1980.
Steeves et al. "Transgenic Soybeans Expressing SiRNAs Specific to a Major Sperm Protein Gene Suppress Heterodera Glycines Reproduction", Functional Plant Biology, 33(11): 991-999, Nov. 1, 2006. Abstract.
Taylor et al. "Validation of Spermidine Synthase as a Drug Target in African Trypanosomes", Biochemical Journal, 409(2): 563-569, Jan. 15, 2008.
Tsaousis et al. "A Novel Route for ATP Acquisition by the Remnant Mitochondria of Encephalitozoon Cuniculi", Nature, 453(7194): May 22, 2008. Abstract.
Van Engelsdorp "Colony Collapse Disorder: A Descriptive Study", PLoS ONE, 4(8): e6481: 1-17, 2009.
Wang et al. "Molecular Characterization of an Arachnid Sodium Channel Gene From the Varroa Mite (*Varroa destructor*)", Insect Biochemistry and Molecular Biology, XP002621492, 33(7): 733-739, Jul. 2003. Abstract.
Wang et al. "Tracking Anonymous Peer-to-Peer VoIP Calls on the Internet", ACM, CCS'05, Alexandria, VA, USA, Nov. 7-11, 2005, 11 P., 2005.
Williams "Unique Physiology of Host-Parasite Interactions in Microsporidia Infections", Cellular Microbiology, XP002589428, 11(11): 1551-1560, Nov. 2009.
Williams et al. "Genome Sequence Surveys of Brachiola Algerae and Edhazardia Aedis Reveal Micriosporidia With Low Gene Densities", BMC Genomics, 9(200): 1-9, Apr. 29, 2008.
Yazdani et al. "Two Level State Machine Architecture for Content Inspection Engines", IEEE Communications Society, Proceedings IEEE Infocom, 12 P., 2006.
Office Action dated Dec. 31, 2014 From the Israel Patent Office Re. Application No. 205594.
Translation Dated Jan. 15, 2015 of Office Action dated Dec. 18, 2014 From the Israel Patent Office Re. Application No. 216154.
Translation Dated Jan. 20, 2015 of Office Action dated Dec. 31, 2014 From the Israel Patent Office Re. Application No. 205594.
Office Action dated Jan. 26, 2015 From the Israel Patent Office Re. Application No. 205594.
Translation Dated Feb. 9, 2015 of Office Action dated Jan. 26, 2015 From the Israel Patent Office Re. Application No. 205594.
Communication Pursuant to Rules 70(2) and 70a(2) EPC and Reference to Rule 39(1) EPC dated Mar. 10, 2014 From the European Patent Office Re. Application No. 13156180.4.
Communication Pursuant to Rules 70(2) and 70a(2) EPC and Reference to Rule 39(1) EPC dated Mar. 10, 2014 From the European Patent Office Re. Application No. 13156180.5.
Translation of Office Action dated Jul. 2, 2013 From the State Intellectual Property Office of the People's Republic of China Re. Application No. 201080056585.9.
Translation of Search Report dated Jul. 2, 2013 From the State Intellectual Property Office of the People's Republic of China Re. Application No. 201080056585.9.
Zhou et al. "The Effects of Brood Comb Cell Size on the Reproductive Behavior of the Ectoparasitic Mite *Varroa destructor* on Honey Bees", Chinese Jurnal of Entomology, 43(1): 89-93, Dec. 31, 2006.
International Search Report and the Written Opinion dated Oct. 28, 2013 From the International Searching Authority Re. Application No. PCT/IL2013/050321.
Patent Examination Report dated Oct. 23, 2013 From the Australian Government, IP Australia Re. Application No. 2008325989.
Notice of Allowance dated Oct. 9, 2014 From the Re. U.S. Appl. No. 13/446,557.
Communication Pursuant to Article 94(3) EPC dated Oct. 8, 2013 From the European Patent Office Re. Application No. 10719620.6.
Communication Pursuant to Article 94(3) EPC dated Sep. 29, 2014 From the European Patent Office Re. Application No. 13156180.4.
Communication Pursuant to Article 94(3) EPC dated Sep. 29, 2014 From the European Patent Office Re. Application No. 13156180.5.
International Preliminary Report on Patentability dated Oct. 23, 2014 From the International Bureau of WIPO Re. Application No. PCT/IL2013/050321.
Office Action dated Dec. 18, 2014 From the Israel Patent Office Re. Application No. 216154.
Restriction Official Action dated Feb. 5, 2014 From the Re. U.S. Appl. No. 13/446,557.
Chawla-Sarkar et al. "Downregulation of Bcl-2, FLIP or IAPs (XIAP and Survivin) by SiRNAs Sensitizes Resistant Melanoma Cells to APO2L/TRAIL-Induced Apoptosis", Cell Death and Differentiation, 11: 915-923, Apr. 30, 2004.
Communication Pursuant to Article 94(3) EPC dated Feb. 5, 2015 From the European Patent Office Re. Application No. 13156183.9.
Communication Pursuant to Article 94(3) EPC dated Feb. 6, 2015 From the European Patent Office Re. Application No. 10719620.6.
Examination Report dated Jan. 30, 2015 From the Instituto Mexicano de la Propiedad Industrial Re. Application No. MX/a/2012/004378 and Its Translation to English.
Requisition by the Examiner and Examination Search Report dated Mar. 19, 2015 From the Canadian Intellectual Property Office Re. Application No. 2,704,858.
Corrected Notice of Allowability dated Jun. 10, 2014 From the Re. U.S. Appl. No. 13/318,636.
Examination Report dated May 12, 2014 From the Instituto Mexicano de la Propiedad Industrial Re. Application No. MX/a/2012/004378 and Its Translation Into English.
Office Action dated May 12, 2014 From the State Intellectual Property Office of the People's Republic of China Re. Application No. 201080056585.9 and Its Translation Into English.
Communication Pursuant to Rules 70(2) and 70a(2) EPC and Reference to Rule 39(1) EPC dated Mar. 17, 2014 From the European Patent Office Re. Application No. 13156183.9.
Communication Pursuant to Article 94(3) EPC dated Jul. 12, 2013 From the European Patent Office Re. Application No. 08847971.2.
Communication Pursuant to Article 94(3) EPC dated Nov. 10, 2014 From the European Patent Office Re. Application No. 10779855.5.
Notice of Allowance dated Apr. 22, 2014 From the Re. U.S. Appl. No. 13/318,636.
Official Action dated Apr. 15, 2014 From the Re. U.S. Appl. No. 13/446,557.
Amdam et al. "Altered Physiology in Worker Honey Bees (*Hymenoptera: Apidae*) Infested With the Mite *Varroa destructor* (*Acari: Varroidae*): A Factor in Colony Loss During Overwintering?", Journal of Economic Entomology, 97(3): 741-747, 2004.
Examination Report dated Oct. 31, 2013 From the Instituto Mexicano de la Propiedad Industrial Re. Application No. MX/a/2012/004378 and Its Summary in English.
Patent Examination Report dated Nov. 6, 2014 From the Australian Government, IP Australia Re. Application No. 2010244122.
Communication Relating to the Results of the Partial International Search dated Jul. 24, 2013 From the International Searching Authority Re. Application No. PCT/2013/050321.
Official Action dated Aug. 1, 2013 From the Re. U.S. Appl. No. 13/318,636.
Dietemann et al. "Varroa Destructor: Research Avenues Towards Sustainable Control", Journal of Apicultural Research, XP055069108, 51(1): 125-132, Feb. 2012.
Garbian et al. "Bidirectional Transfer of RNAi Between Honey Bee and Varroa Destructor: Varroa Gene Silencing Reduces Varroa Population", PLOS Pathogens, XP055069058, 8(12): e1003035-1-e1003035-9, Dec. 20, 2012.
Communication Pursuant to Article 94(3) EPC dated Feb. 17, 2014 From the European Patent Office Re. Application No. 08847971.2.
Office Action dated Jan. 19, 2014 From the Israel Patent Office Re. Application No. 205594 and Its Translation Into English.
European Search Report and the European Search Opinion dated Feb. 3, 2014 From the European Patent Office Re. Application No. 13156180.4.

(56) References Cited

OTHER PUBLICATIONS

European Search Report and the European Search Opinion dated Feb. 3, 2014 From the European Patent Office Re. Application No. 13156180.5.
European Search Report and the European Search Opinion dated Feb. 6, 2014 From the European Patent Office Re. Application No. 13156183.9.
Cox-Foster et al. "A Metagenomic Survey of Microbes in Honey Bee Colony Collapse Disorder", Science, 318(5848): 283-287, Oct. 2007.
Nielsen et al. "Sacbrood Virus Isolate T73/05A Polyprotein Gene, Partial CDs", Database EMBL [Online], XP002719130, Retrieved From IBIS, Database Accession No. EF570887, May 12, 2007.
Palacios et al. "Genetic Analysis of Israel Acute Paralysis Virus: Distinct Clusters Are Circulating in the United States", Journal of Virology, 82(13): 6209-6217, Jul. 2008.
Whitfield et al. "BB170006B20C05.5 Bee Brain Normalized/Subtracted Library, BB17 Apis Mellifera cDNA Clone BB170006B20C05 5', mRNA Sequence", Database EMBL [Online], XP002719131, Retrieved IBIS, Database Accession No. BI503250, Aug. 30, 2001.
Communication Pursuant to Article 94(3) EPC dated Sep. 1, 2015 From the European Patent Office Re. Application No. 10779855.5.
Communication Pursuant to Article 94(3) EPC dated Sep. 4, 2015 From the European Patent Office Re. Application No. 13156183.9.
Examination Report dated Aug. 25, 2015 From the Intellectual Property Office of New Zealand Re. Application No. 700791.
Decision on Rejection dated Aug. 3, 2015 From the State Intellectual Property Office of the People's Republic of China Re. Application No. 201080056585.9 and Its Translation Into English.
Communication Pursuant to Article 94(3) EPC dated Jun. 8, 2015 From the European Patent Office Re. Application No. 13156185.4.
Communication Pursuant to Article 94(3) EPC dated May 29, 2015 From the European Patent Office Re. Application No. 13156180.5.
Aoki et al., "In Vivo Transfer Efficiency of Antisense Oligonucleotides into the Myocardium Using HVJ-Liposome Method," *Biochem. Biophys. Res. Commun.*, 231:540-545 (1997).
Fiala et al., "Reversible Downregulation of Protein Kinase A during Olfactory Learning Using Antisense Technique Impairs Long-Term Memory Formation in the Honeybee, *Apis mellifera,*" *J. Neuroscience*, 19:10125-10134 (1999) Herewith.
Kronenwett et al., "Oligodeoxyribonucleotide Uptake in Primary Human Hematopoietic Cells is Enhanced by Cationic Lipids and Depends on the Hematopoietic Cell Subset," *Blood*, 91:852-862 (1998).
Lavigne et al., "Enhanced Antisense Inhibition of Human Immunodeficiency Virus Type 1 in Cell Cultures by DLS Delivery System," *Biochem. Biophys. Res. Commun.*, 237:566-571 (1997).
Luft, "Making Sense Out of Antisense Oligodeoxynucleotide Delivery: Getting There is Half the Fun," *J. Mol. Med.*, 76:75-76 (1998).
Paddison et al., "Stable Suppression of Gene Expression by RNAi in Mammalian Cells," *Proc. Natl. Acad. Sci. USA*, 99(3):1443-1448 (2002).
Rajur et al., "Covalent Protein —Oligonucleotide Conjugates for Efficient Delivery of Antisense Molecules," *Bioconjug. Chem.*, 8:935-940 (1997).
Strat et al., "Specific and Nontoxic Silencing in Mammalian Cells with Expressed Long dsRNAs," *Nucl. Acids Res.*, 34(13):3803-3810 (2006).
Araujo et al. "RNA Interference of the Salivary Gland Nitrophorin 2 in the Triatomine Bug Rhodnius Prolixus (Hemiptera: Reduviidae) by dsRNA Ingestion or Injection", Insect Biochemistry and Molecular Biology, 36: 683-693(2006).
Baum et al., "Progress Towards RNAi-Mediated Insect Pest Management" Advances in Insect Physiology, 47:249-295 (2014).
Chawla-Sarkar et al., "Downi-egulation of Bc1-2, FLIP or IAPs (XIAP and Survivin) by SiRNAs Sensitizes Resistant Melanoma Cells to APO2L/TRAIL-Induced Apoptosis," *Cell Death and Differentiation*, 11:915-923 (2004).

Communication Pursuant to Article 94(3) EPC dated Jul. 12, 2013 From the European Patent Office in Application No. 08847971.2.
Common et al., "Genomic Analyses of the Microsporidian Nosema Ceranae, An Emergent Pathogen of Honey Bees," *PLoS Pathogens*, 5(6):e1000466: 1-14 (2009).
Dietemann et al., "Varroa Destructor: Research Avenues Towards Sustainable Control," *Journal of Apicultural Research*, 51 (1): 125-132, (2012).
Garbian et al., "Bidirectional Transfer of RNAi Between Honey Bee and Varroa Destructor: Varroa Gene Silencing Reduces Varroa Population," *PLOS Pathogens*, 8(12):1-9 (2012).
International Preliminary Report on Patentability dated Nov. 17, 2011 From the International Bureau of WIPO in Application No. PCTAB2010/051980.
International Preliminary Report on Patentability dated Apr. 26, 2012 From the International Bureau of WIPO in Application No. PCT/IL2010/000844.
International Search Report and the Written Opinion dated Jul. 19, 2010 From the International Searching Authority in Application No. PCT/IB2010/051980.
International Search Report and the Written Opinion dated Feb. 24, 2011 From the International Searching Authority in Application No. PCT/IL2010/000844.
Lanzi et al., "Deforming Wing Virus Gene for Polyprotein, Genomic RNA," NCBI Database [Online], GenBank Accession No. AJ489744. 2, Database Accession No. AJ489744 (2006).
Leat et al., "Black Queen Cell Virus Nonstructural Polyprotein (ORF1) and Structural Polyprotein (ORF2) Genes, Complete Cds," Database NCBI [Online], GenBank Accession No. AF183905.1, Database Accession No. AF183905 (2000).
O'Riordan et al., "Inhibitor of Apoptosis (IAP) Proteins in Eukaryotic Evolution and Development: A Model of Thematic Conservation," *Developmental Cell*, 15(4):497-508 (2008).
Palacios et al., "Genetic Analysis of Israel Acute Paralysis Virus: Distinct Clusters Are Circulating in the United States," *Journal of Virology*, 82(13):6209-6217 (2008).
Patel et al., "The Making of a Queen: TOR Pathway is a Key Player in Diphenic Caste Development," *PLoS ONE*, 2(6):e509-1-e509-7 (2007).
Shen et al., "The Role of Varroa Mites in Infections and Deformed Wing Virus (DWV) in Honey," Available Online Aug. 18, 2005.
Ullu et al., "RNA Interference in Protozoan Parasites," *Cellular Microbiology*, 6(6):509-519 (2004).
Williams "Unique Physiology of Host-Parasite Interactions in Microsporidia Infections," *Cellular Microbiology*, 11(11):1551-1560 (2009).
Williams et al., "Genome Sequence Surveys of Brachiola Algerae and Edhazardia Aedis Reveal Micriosporidia With Low Gene Densities," *BMC Genomics*, 9(200):1-9 (2008).
Yadav et al., "Host-Generated Double Stranded RNA Induces RNAi in Plant-Parasitic Nematodes and Protects the Host From Infection," *Molecular & Biochemical Parasitology*, 148:219-222 (2006).
Office Action dated Nov. 25, 2014 From the State Intellectual Property Office of the People's Republic of China Re. Application No. 201080056585.9 and Its Translation Into English.
Examination Report dated Mar. 20, 2015 From the Government of India, Patent Office, Intellectual Property Building Re. Application No. 1150/MUMNP/2010.
Agricultural Chemical Usage 2006 Vegetables Summary, Agricultural Statistics Board, NASS, USDA, pp. 1-372 (2007).
Agrios, Plant Pathology (Second Edition), 2:466-470 (1978).
Al-Kaff et al., "Plants rendered herbicide-susceptible by cauliflower mosaic virus-elicited suppression of a 35S promoter-regulated transgene," Nature Biotechnology, 18:995-999 (2000).
Amarzguioui et al., "An algorithm for selection of functional siRNA sequences," Biochemical and Biophysical Research Communications, 316:1050-1058 (2004).
Ambrus et al., "The diverse roles of RNA helicases in RNAi," Cell Cycle, 8(21):3500-3505 (2009).
An et al., "Transient RNAi Induction against Endogenous Genes in Arabidopsis Protoplasts Using in Vitro-Prepared Double-Stranded RNA," Biosci Biotechnol Biochem, 69(2):415-418 (2005).

(56) References Cited

OTHER PUBLICATIONS

Andersson et al., "A novel selection system for potato transformation using a mutated AHAS gene," Plant Cell Rep, 22:261-267 (2003).
Anonymous, "Agronomy Facts 37: Adjuvants for enhancing herbicide performance," pp. 1-8, (Jan. 26, 2000), Web, (Jan. 21, 2014).
Arpaia et al., "Production of transgenic eggplant (*Solanum melongena* L.) resistant to Colorado Potato Beetle (*Leptinotarsa decemlineata* Say)," (1997) Theor. Appl. Genet., 95:329-334 (1997).
Artymovich, "Using RNA interference to increase crop yield and decrease pest damage," MMG 445 Basic Biotech., 5(1):7-12 (2009).
Axtell et al., "A Two-Hit Trigger for siRNA Biogenesis in Plants," Cell, 127:565-577 (2006).
Bachman et al., "Characterization of the spectrum of insecticidal activity activity of a double-stranded RNA with targeted Rootworm against Western Corn LeConte (*Diabrotica virgifera virgifera*)," Transgenic Res. pp. 1-16 (2013).
Bart et al., "A novel system for gene silencing using siRNAs in rice leaf and stem-derived protoplasts," Plant Methods, 2(13):1-9 (2006).
Baulcombe, "Rna silencing and heritable epigenetic effects in tomato and Arabidopsis," Abstract 13th Annual Fall Symposium, Plant Genomes to Phenomes, Donald Danforth Plant Science Center, 28-30 (2011).
Bayer et al., "Programmable ligand-controlled riboregulators of eukaryotic gene expression," Nature Biotechnol., 23(3):337-343 (2005).
Beal, et al., "Second Structural Motif for Recognition of DNA by Oligonucleotide-Directed Triple-Helix Formation," Science, 251:1360-1363 (1992).
Becker et al., "Fertile transgenic wheat from microprojectile bombardment of scutellar tissue," The Plant Journal, 5(2):299-307 (1994).
Bhatia et al., "Aphid resistance in *Brassica* crops: Challenges, biotechnological progress and emerging possibilities," *Biotechnology Advances* 29:879-955 (2011).
Boletta et al., "High Efficient Non-Viral Gene Delivery to the Rat Kidney by Novel Polycationic Vectors," J. Am Soc. Nephrol., 7:1728 (1996).
Bolognesi et al., "Characterizing the Mechanism of Action of Double-Stranded RNA Activity against Western Corn Rootworm(*Diabrotica virgifera virgifera* LeConte)," PLoS One 7(10):e47534 (2012).
Brodersen et al., "The diversity of RNA silencing pathways in plants," Trends in Genetics, 22(5):268-280 (2006).
Busch et al., "RNAi for discovery of novel crop protection products," Pflanzenschutz-Nachrichten Bayer, 58(1):34-50 (2005).
Chabannes et al., "In situ analysis of lignins in transgenic tobacco reveals a differential impact of individual transformations on the spatial patterns of lignin deposition at the cellular and subcellular levels," the Plant Journal, 28(3):271-282 (2001) Herewith.
Chabbouh et al., "Cucumber mosaic virus in artichoke," FAO Plant Protection Bulletin, 38:52-53 (1990).
Chang et al., "Dual-target gene silencing by using long, sythetic siRNA duplexes without triggering antiviral responses," Molecules and Cells, 27(6) 689-695 (2009).
Chang et al., "Cellular Internalization of Fluorescent Proteins via Arginine-rich Intracellular Delivery Peptide in Plant Cells," Plant Cell Physiol., 46(3):482-488 (2005).
Chen et al., "Exploring MicroRNA-Like Small RNAs in the Filamentous Fungus Fusarium oxysporum," PLOS One, 9(8):e104956:1-10 (2014).
Christiaens et al., "The challenge of RNAi-mediated control of hemipterans," Current Opinion in Insect Science, 6:15-21 (2014).
CN101914540 Patent Diclosure, "Introduction of RNA into plant by interference," (2010).
Communication pursuant to Article 94(3) EPC dated Jan. 14, 2016, in European Patent Application No. 12 832 415.9.
Communication pursuant to Article 94(3) EPC dated Jun. 26, 2015, in European Patent Application No. 11 753 916.3 .
Communication pursuant to Article 94(3) EPC dated Mar. 18, 2016, in European Patent Application No. 12 832 160.1.
Communication pursuant to Article 94(3) EPC dated Mar. 24, 2016, in European Patent Application No. 12 831 684.1.
Communication pursuant to Article 94(3) EPC dated Mar. 4, 2016, in European Patent Application No. 12 830 932.5.
Communication pursuant to Article 94(3) EPC dated Mar. 9, 2016, in European Patent Application No. 12 831 166.9.
Communication pursuant to Article 94(3) EPC dated Oct. 23, 2015, in European Patent Application No. 12 831 945.6.
Concise Descriptions of Relevance filed by a third party dated Nov. 29, 2012, in U.S. Appl. No. 13/042,856.
Constan et al., "An outer envelope membrane component of the plastid protein import apparatus plays an essential role in *Arabidopsis*," The Plant Journal, 38:93-106 (2004).
Cost Action FA0806 progress report "Plant virus control employing RNA-based vaccines: A novel non-transgenic strategy" (2010).
Dalakouras et al., "Induction of Silencing in Plants by High-Pressure Spraying of in vitro-Synthesized Small RNAs," Frontiers in Plant Science, 7(1327):1-5 (2016).
Dalmay et al., "An RNA-Depenedent Rna Polymerase Gene in *Arabidopsis* Is Required for Posttranscriptional Gene Silencing Mediated by a Transgene but Not by a Virus," Cell, 101:543-553 (2000).
Database Accession No. BT006855, "*Homo sapiens* calmodulin 3(phosphorylase kinase, delta) mRNA" pp. 1-2 (2003).
Davidson et al., "Engineering regulatory RNAs," TRENDS in Biotechnology, 23(3):109-112 (2005).
Dawson et al., "cDNA cloning of the complete genome of tobacco mosaic virus and production of infectious transcripts," Proc. Natl. Acad. Sci. USA, 83:1832- 1836 (1986).
De Frammond, "MINI-Ti: A New Vector Strategy for Plant Genetic Engineering," Nature Biotechnology, 1:262-269 (1983).
Desai et al., "Reduction in deformed wing virus infection in larval and adult honey bees (*Apis mellifera* L.) by double-stranded RNA ingestion," Insect Molecular Biology, 21(4):446-455 (2012).
Di Stilio et al., "Virus-Induced Gene Silencing as a Tool for Comparative Functional Studies in Thalictrum," PLoS One, 5(8):e12064 (2010).
Du et al., "A systematic analysis of the silencing effects of an active siRNA at all single-nucleotide mismatched target sites," Nucleic Acids Research, 33(5):1671-1677 (2005).
Dunoyer et al., "Small RNA Duplexes Function as Mobile Silencing Signals Between Plant Cells," Science, 328:912-916 (2010).
Eamens et al., "RNA Silencing in Plants: Yesterday, Today, and Tomorrow," Plant Physiology, 147(2):456-468 (2008).
Ellington et al., "In vitro selection of RNA molecules that bind specific ligands," Nature, 346:818-822 (1990).
European Search Report dated Jun. 29, 2018, in European Patent Application No. 18157745.3.
European Search Report dated Sep. 7, 2017, in European Patent Application No. 17152830.0.
Examination Report dated Mar. 1, 2018, in Australian Patent Application No. 2013264742.
Extended European Search Report dated Feb. 2, 2015, in European Patent Application No. 12 830 932.5.
Extended European Search Report dated Feb. 27, 2015, in European Patent Application No. 12 832 160.1.
Extended European Search Report dated Jan. 14, 2019, in European Patent Application No. 16789940.0.
Extended European Search Report dated Feb. 3, 2015, in European Patent Application No. 12 831 945.6.
Extended European Search Report dated Jan. 20, 2016, in European Patent Application No. 13 794 339.5.
Extended European Search Report dated Jan. 21, 2015, in European Patent Application No. 12 832 415.9.
Extended European Search Report dated Jan. 29, 2015, in European Patent Application No. 12 831 567.8.
Extended European Search Report dated Jun. 29, 2015, in European Patent Application No. 12 831 494.5.
Extended European Search Report dated Mar. 17, 2015, in European Patent Application No. 12 831 684.1.

(56) References Cited

OTHER PUBLICATIONS

Extended European Search Report dated Mar. 3, 2015, in European Patent Application No. 12 831 166.9.
Extended European Search Report dated May 23, 2018, in European Patent Application No. 15826865.6.
Extended European Search Report dated Nov. 7, 2017, in European Patent Application No. 15811092.4.
Extended European Search Report dated Nov. 8, 2017, in European Patent Application No. 15737282.2.
Extended European Search Report dated Oct. 8, 2013, in European Patent Application No. 11753916.3.
Extended European Search Report dated Sep. 29, 2016, in European Patent Application No. 14778840.0.
Extended European Search Report dated Apr. 13, 2018, in European Patent Application No. 15812530.0.
Extended European Search Report dated Mar. 15, 2018, in European Patent Application No. 17181861.0.
Extended European Search Report dated Mar. 4, 2019, in European Patent Application No. 18 20 7017.7.
Fernandez et al., "Uptake of Hydrophilic Solutes Through Plant Leaves: Current State of Knowledge and Perspectives of Foliar Fertilization," Critical Reviews in Plant Sciences, 28:36-38 (2009).
Final Office Action dated Apr. 7, 2016, in U.S. Appl. No. 13/619,980.
Final Office Action dated Dec. 17, 2015, in U.S. Appl. No. 14/335,135.
Final Office Action dated Feb. 17, 2016, in U.S. Appl. No. 13/612,929.
Final Office Action dated Feb. 4, 2016, in U.S. Appl. No. 13/612,936.
Final Office Action dated Jun. 30, 2016, in U.S. Appl. No. 13/901,326.
Final Office Action dated Mar. 2, 2016, in U.S. Appl. No. 13/612,995.
Final Office Action dated Mar. 21, 2016, in U.S. Appl. No. 13/612,925.
Final Office Action dated May 26, 2016, in U.S. Appl. No. 14/532,596.
Final Office Action dated Nov. 10, 2015, in U.S. Appl. No. 13/612,985.
Final Office Action dated Nov. 10, 2016, in U.S. Appl. No. 13/583,302.
Final Office Action dated Nov. 19, 2015, in U.S. Appl. No. 13/612,941.
Final Office Action dated Nov. 30, 2015, in U.S. Appl. No. 13/612,948.
Final Office Action dated Nov. 7, 2013, in U.S. Appl. No. 13/042,856.
Final Office Action dated Oct. 20, 2016, in U.S. Appl. No. 14/480,199.
Final Office Action dated Oct. 22, 2015, in U.S. Appl. No. 14/608,951.
Final Office Action dated Sep. 28, 2015, in U.S. Appl. No. 13/932,051.
Final Office Action dated Sep. 9, 2016, in U.S. Appl. No. 13/612,954.
Final Office Action dated Sep. 9, 2016, in U.S. Appl. No. 14/603,347.
Final Office Action dated Sep. 9, 2016, in U.S. Appl. No. 14/608,951.
Fire et al., "Potent and specific genetic interference by double-stranded RNA in Caenorhabditis elegans," Nature, 391:806-811 (1998).
First Examination Report dated Apr. 23, 2013, in New Zealand Patent Application No. 601784.
First Examination Report dated Jul. 28, 2014, in New Zealand Patent Application No. 627060.
First Office Action dated Aug. 31, 2015, in Chinese Patent Application No. 201280053985.3.
First Office Action dated Feb. 2, 2016, in Chinese Patent Application No. 201380039346.6.
First Office Action dated Jul. 7, 2015, in Chinese Patent Application No. 201280054820.8.
First Office Action dated Mar. 12, 2015, in Chinese Patent Application No. 201280053984.9.
First Office Action dated Mar. 2, 2015, in Chinese Patent Application No. 201280054819.5.
First Office Action dated May 27, 2015, in Chinese Patent Application No. 201280054179.8.
First Office Action dated Sep. 9, 2015, in Chinese Patent Application No. 201280055409.2.
First Office Action dated Nov. 27, 2019, in Chinese Patent Application No. 2016800377700 (with English language translation).
Foley et al., "The distribution of *Aspergillus* spp. Opportunistic parasites in hives and their pathogenicity to honey bees," Veterinary Microbiology, 169:203-210 (2014).

Fraley et al., "Liposome-mediated delivery of tobacco mosaic virus RNA into tobacco protoplasts: A sensitive assay for monitoring liposome-protoplast interactions," Proc Natl Acad Sci U S A., 79(6):1859-1863 (1982).
Friedberg, "Automated protein function prediction—the genomic challenge," Briefings in Bioinformatics, 7(3):225-242 (2006).
Fukuhara et al., "Enigmatic Double-Stranded RNA in Japonica Rice," Plant Molecular Biology, 21:1121-1130 (1993).
Fukuhara et al., "The Unusual Structure of a Novel RNA Replicon in Rice," The Journal of Biological Chemistry, 270(30):18147-18149 (1995).
Fukuhara et al., "The wide distribution of endornaviruses, large double-stranded RNA replicons with plasmid-like properties," Archives of Virology, 151:995-1002 (2006).
Fukunaga et al., "dsRNA with 5' overhangs v contributes to endogenous and antiviral Rna silencing pathways in plants," The EMBO Journal, 28(5):545-555 (2009).
Further Examination Report dated May 16, 2014, in New Zealand Patent Application No. 601784.
Gallic et al., "Identification of the motifs within the tobacco mosaic virus 5'leader responsible for enhancing translation," Nucleic Acids Res., 20(17):4631-4638 (1992).
Gan et al.' "Bacterially expressed dsRNA protects maize against SCMV infection," Plant Cell Rep, 29(11):1261-1268.
Gao et al., "Down-regulation of acetolactate synthase compromises 01-1-mediated resistance to powdery mildew in tomato," BMC Plant Biology, 14 (2014).
Gaskin et al., "Novel organosillicone adjuvants to reduce agrochemical spray volumes on row crops," New Zealand Plant Protection, 53:350-354 (2000).
Gong et al., "Silencing of Rieske iron—sulfur protein using chemically synthesised siRNA as a potential biopesticide against Plutella xylostella," Pest Manag Sci, 67:514-520 (2011).
Gossamer Threads, Compendium of Herbicide Adjuvants: Organo-Silicone Surfactant, pp. 1-4 (1998).
Hagio, "Chapter 25: Direct Gene Transfer into Plant Mature Seeds via Electroporation After Vacuum Treatment," Electroporation and Sonoporation in Developmental Biology, pP. 285-293 (2009).
Hamilton et al., "Two classes of short interfering RNA in RNA silencing," EMBO J., 21(17):4671-4679 (2002).
Han et al., "Molecular Basis for the Recognition of Primary microRNAs by the Drosha-DGCR8 Complex," Cell, 125(5):887-901 (2006).
Hannon, "RNA interference," Nature, 481:244-251 (2002).
Heath et al., "RNA Interference Technology to Control Pest Sea Lampreys—A Proof-of-Concept," PLOS One, 9(2):e88387:1-9 (2014).
Heneberg et al., "Assemblage of filamentous fungi associated with aculeate hymenopteran brood in reed galls," *Journal of Invertebrate Pathology*, 133:95-106 (2016).
Herman et al., "A three-component dicamba O-demethylase from Pseudomonas maltophilia, strain DI-6: gene isolation, characterization, and heterologous expression," J. Biol. Chem., 280: 24759-24767 (2005).
Hess, "Surfactants and Additives," 1999 Proceedings of the California Weed Science Society, 51:156-172 (1999).
Hewezi et al., "Local infiltration of high- and low-molecular-weight RNA from silenced sunflower (*Helianthus annuus* L.) plants triggers post-transcriptional gene silencing in non-silenced plants," Plant Biotechnology Journal, 3:81-89 (2005).
Himber et al., "Transitivity-dependant and -independent cell-to-cell movement of RNA silencing," The Embo Journal, 22(17):4523-4533 (2003).
Hsieh et al., "A library of siRNA duplexes targeting the phosphoinositide 3-kinase pathway: determinants of gene silencing for use in cell-based screens," Nucleic Acids Res., 32(3):893-901 (2004).
Hu et al., "High efficiency transport of quantum dots into plant roots with the aid of silwet L-77," Plant Physiology and Biochemistry, 48:703-709 (2010).
Huang et al., "Engineering broad root-know resistance in transgenic plants by RNAi silencing of a conserved and essential root-knot nematode parasitism gene," *Proc. Natl. Acad. Sci. USA*, 103(39):14302-14306 (2006).

(56) References Cited

OTHER PUBLICATIONS

Huesken et al., "Design of a genome-wide siRNA library using an artificial neural network," Nature Biotechnology, 23(8): 995-1001 (2005).
Hunter et al., "RNA Interference Strategy to suppress Psyllids & Leafhoppers," International Plant and Animal Genome XIX, 15-19 (2011).
Huvenne et al., "Mechanisms of dsRNA uptake in insects and potential of RNAi for pest control: a review," *Journal of Insect Physiology*, 56:227-235 (2010).
Ichihara et al., "Thermodynamic instability of siRNA duplex is a prerequisite for dependable prediction of siRNA activities," Nucleic Acids Res., 35(18):e123 (2007).
International Preliminary Report on Patentability (Chapter II) dated Jul. 24, 2015, in International Application No. PCT/US2014/047204.
International Preliminary Report on Patentability dated Sep. 11, 2012, in International Application No. PCT/US2011/027528.
International Preliminary Report on Patentability dated Sep. 11, 2014, in International Application No. PCT/IL2013/050447.
International Rice Genome Sequencing Project, the map-based sequence of the rice genome, Nature, 436(11):793-800 (2005).
International Search Report and the Written Opinion dated Feb. 25, 2013, in International Application No. PCT/US2012/054883.
International Search Report and the Written Opinion dated Feb. 27, 2013, in International Application No. PCT/US2012/054814.
International Search Report and the Written Opinion dated Feb. 27, 2013, in International Application No. PCT/US2012/054842.
International Search Report and the Written Opinion dated Feb. 27, 2013, in International Application No. PCT/US2012/054894.
International Search Report and the Written Opinion dated Feb. 27, 2013, in International Application No. PCT/US2012/054974.
International Search Report and the Written Opinion dated Feb. 27, 2013, in International Application No. PCT/US2012/054980.
International Search Report and the Written Opinion dated Jul. 15, 2014, in International Application No. PCT/US2014/025305.
International Search Report and the Written Opinion dated Jul. 22, 2014, in International Application No. PCT/IL2013/051083.
International Search Report and the Written Opinion dated Jul. 22, 2014, in International Application No. PCT/IL2013/051085.
International Search Report and the Written Opinion dated Jul. 24, 2014, in International Application No. PCT/US2014/026036.
International Search Report and the Written Opinion dated May 10, 2011, in International Application No. PCT/US2011/027528.
International Search Report and the Written Opinion dated Oct. 1, 2013, in International Application No. PCT/IL2013/050447.
International Search Report and Written Opinion dated Mar. 26, 2015, in International Application No. PCT/US2014/069353.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion dated Dec. 31, 2015, in International Application No. PCT/US2015/042415.
International Search Report and Written Opinion dated Feb. 23, 2015, in International Application No. PCT/US2014/063832.
International Search Report and Written Opinion dated Jul. 8, 2015, in International Application No. PCT/US2015/011408.
International Search Report and Written Opinion dated Mar. 26, 2015, in International Application No. PCT/US2014/069535.
International Search Report and Written Opinion dated May 23, 2017, in International Application No. PCT/US2017/015061.
International Search Report and Written Opinion dated May 26, 2016, in International Application No. PCT/US2016/014344.
International Search Report and Written Opinion dated Nov. 24, 2015, in International Application No. PCT/US2015/037522.
International Search Report and Written Opinion dated Nov. 27, 2015, in International Application No. PCT/U S2015/037015.
International Search Report and Written Opinion dated Oct. 1, 2015 in International Application No. PCT/US2015/022985.
International Search Report and Written Opinion dated Oct. 17, 2016, in International Application No. PCT/US2016/030579.
International Search Report dated Mar. 12, 2013, in International Application No. PCT/US2012/054789.
Invitation to Pay Additional Fees dated May 13, 2009, in International Application No. PCT/IL2008/001440.
Invitation to Pay Additional Fees dated May 6, 2014, in International Application No. PCT/IL2013/051083.
Invitation to Pay Additional Fees dated May 6, 2014, in International Application No. PCT/IL2013/051085.
Invitation to Pay Additional Fees dated Nov. 25, 2014, in International Application No. PCT/US2014/047204.
Invitation to Pay Additional Fees dated Sep. 8, 2015, in International Application No. PCT/US2015/037015.
Invitation to Pay Additional Fees dated Sep. 9, 2015, in International Application No. PCT/US2015/037522.
Isaacs et al., "Engineered riboregulators enable post-transcriptional control of gene expression," Nature Biotechnology, 22(7):841-847 (2004).
Jarvis et al., "An arabidopsis mutant defective in the plastid general protein import apparatus," Science, 282:100-103 (1998).
Ji et al., "Regulation of small RNA stability: methylation and beyond," Cell Research, 22:624-636 (2012).
Jin et al., "Posttranslational Elevation of Cell Wall Invertase Activity by Silencing its Inhibitor in Tomato Delays Leaf Senescence and Increases Seed Weight and Fruit Hexose Level," The Plant Cell, 21:2072-2089 (2009).
Jones-Rhoades et al., "MicroRNAs and Their Regulatory Roles in Plants," Annu. Rev. Plant Biol., 57:19-53 (2006) Herewith.
Kam et al., "Nanotube Molecular Transporters: Internalization of Carbon Nanotube—Protein Conjugates into Mammalian Cells," J. Am. Chem. Soc., 126(22):6850-6851 (2004).
Khodakovskaya et al., "Carbon Nanotubes Are Able to Penetrate Plant Seed Coat and Dramatically Affect Seed Germination and Plant Growth," ACS Nano, 3(10):3221-3227 (2009).
Khovorova et al., "Rational siRNA design for RNA interference," *Nature Biotechnol.*, 22 :326-330 (2004).
Kikkert et al., "Stable Transformation of Plant Cells by Particle Bombardment/Biolistics," Methods in Molecular Biology, 286:61-78 (2005).
Kim et al., "Optimization of Conditions for Transient Agrobacterium-Mediated Gene Expression Assays in Arabidopsis," Plant Cell Reports, 28:1159-1167 (2009).
Kim et al., "Synthetic dsRNA Dicer substrates enhance RNAi potency and efficacy," Nature Biotechnology, 23(2):222-226 (2005).
Klahre et al., "High molecular weight RNAs and small interfering RNAs induce systemic posttranscriptional gene silencing in plants," Proc. Natl. Acad. Sci. USA, PNAS, 99(18):11981-11986 (2002).
Kondylis et al., "The Golgi apparatus: Lessons from *Drosophila*," *FEBS Letters* 583:3827-3838 (2009).
Kumar et al., "Sequencing, De Novo Assembly and Annotation of the Colorado Potato Beetle, Leptinotarsa decemlineata, Transcriptome," PLOS One, 9(1):e86012:1-17 (2014).
Kusaba, "RNA interference in crop plants," Curr Opin Biotechnol, 15(2):139-143 (2004).
Lee et al., "A systematic RNAi screen identifies a critical role for mitochondria in C. elegans longevity." *Nature Genetics*, 33:40-48 (2003).
Lee et al., "Aptamer Database," Nucleic Acids Research, 32:D95-D100 (2004).
Li et al., "Rna interference in *Nilaparvata lugens* (Homoptera:Delphacidae) based on dsRNA ingestion," *Pest Manag. Sci.*, 67:852-859 (2011).
Li et at., "Long dsRNA but not siRNA initiates RNAi in western corn rootworm larvae and adults," Journal of Applied Entomology, 139(6):432-445 (2015).
Liu et al., "Carbon Nanotubes as Molecular Transporters for Walled Plant Cells," Nano Letters, 9(3):1007-1010 (2009).
Liu et al., "DNAzyme-mediated recovery of small recombinant RNAs from a 5S rRNA-derived chimera expressed in *Escherichia coli*," BMC Biotechnology, 10:85 (2010).
Liu, "Influence of Sugars on the Foliar Uptake of Bentazone and Glyphosate," New Zealand Plant Protection, 55:159-162 (2002).

(56) References Cited

OTHER PUBLICATIONS

Liu, "The Transformation of Nucleic Acid Degradants in Plants," China Organic Fertilizers, Agriculture Press, ISBN: 7-1091634 (with English translation).
Llave et al., "Endogenous and Silencing-Associated Small RNAs in Plants," The Plant Cell, 14:1605-1619 (2002).
Lu et al., "Rna silencing in plants by the expression of siRNA duplexes," Nucleic Acids Res., 32(21):e171 (2004).
Luque et al., "Water Permeability of Isolated Cuticular Membranes: A Structural Analysis," Archives of Biochemistry and Biophysics, 317(2):417-422 (1995).
Maas et al., "Mechanism and optimized conditions for PEG mediated DNA transfection into plant protoplasts," Plant Cell Reports, 8:148-149 (1989).
MacKenzie et al., "Transgenic Nicotiana debneyii expressing viral coat protein are resistant to potato virus S infection," Journal of General Virology, 71:2167- 2170 (1990).
Makkouk et al., "Virus Diseases of Peas, Beans, and Faba Bean in the Mediterranean region," Adv Virus Res, 84:367-402 (2012).
Manoharan, "Oligonucleotide Conjugates as Potential Antisense Drugs with Improved Uptake, Biodistribution, Targeted Delivery, and Mechanism of Action," Antisense & Nucleic Acid Drug Development, 12:103-128 (2002).
McGinnis, "RNAi for functional genomics in plants," Brief Funct Genomics, 9(2):111-7 (2010).
Meins et al., "Rna Silencing Systems and Their Relevance to Plant Development," Annu. Rev. Cell Dev. Biol., 21:297-318 (2005).
Melnyk et al., "Intercellular and systemic movement of RNA silencing signals," The Embo Journal, 30:3553-3563 (2011).
Migge et al., "Greenhouse-grown conditionally by expression of plastidic glutamine synthetase lethal tobacco plants obtained antisense RNA may contribute to biological safety," Plant Science 153:107-112 (2000).
Molnar et al., "Plant Virus-Derived Small redominantly from Highly Structured Single Interfering RNAs Originate -Stranded Viral RNAs," Journal of Virology, 79(12):7812-7818 (2005).
Molnar et al., "Small Silencing RNAs in Plants Are Mobile and Direct Epigenetic Modification in Recipient Cells," Science, 328:872-875 (2010).
Moriyama et al., "Double-stranded RNA in rice: a novel RNA replicon in plants," Molecular & General Genetics, 248(3):364-369 (1995).
Moriyama et al., "Stringently and developmentally regulated levels of a cytoplasmic double-stranded RNA and its high-efficiency transmission via egg and pollen in rice," Plant Molecular Biology, 31:713-719 (1996).
Morrissey et al., "Potent and persistent in vivo anti-HBV activity of chemically modified siRNAs," Nat Biotechnol. 23(8):1002-1007 (2005).
Mount et al., "Gene and Metabolite Regulatory Network Analysis of Early Developing Fruit Tissues Highlights New Candidate Genes for the Control of Tomato Fruit Composition and Development," Plant Physiology, 149:1505- 1528 (2009).
Non-Final Office Action dated Apr. 11, 2013, in U.S. Appl. No. 13/042,856.
Non-Final Office Action dated Apr. 29, 2016, in U.S. Appl. No. 13/583,302.
Non-Final Office Action dated Aug. 10, 2016, in U.S. Appl. No. 13/612,995.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Aug. 19, 2016, in U.S. Appl. No. 13/612,925.
Non-Final Office Action dated Aug. 19, 2016, in U.S. Appl. No. 13/612,929.
Non-Final Office Action dated Aug. 3, 2016, in U.S. Appl. No. 14/015,715.
Non-Final Office Action dated Aug. 5, 2016, in U.S. Appl. No. 14/015,785.
Non-Final Office Action dated Aug. 8, 2016, in U.S. Appl. No. 13/612,936.
Non-Final Office Action dated Dec. 17, 2015, in U.S. Appl. No. 14/532,596.
Non-Final Office Action dated Feb. 10, 2016, in U.S. Appl. No. 13/901,326.
Non-Final Office Action dated Feb. 23, 2016, in U.S. Appl. No. 14/603,347.
Non-Final Office Action dated Feb. 23, 2016, in U.S. Appl. No. 14/608,951.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated Mar. 1, 2016, in U.S. Appl. No. 13/612,954.
Non-Final Office Action dated Mar. 21, 2018, in U.S. Appl. No. 13/619,980.
Non-Final Office Action dated Mar. 30, 2015, in U.S. Appl. No. 13/583,302.
Non-Final Office Action dated May 15, 2015, in U.S. Appl. No. 14/608,951.
Non-Final Office Action dated May 22, 2015, in U.S. Appl. No. 13/612,985.
Non-Final Office Action dated May 4, 2015, in U.S. Appl. No. 13/932,05.
Non-Final Office Action dated Nov. 9, 2016, in U.S. Appl. No. 14/901,003.
Non-Final Office Action dated Oct. 3, 2016, in U.S. Appl. No. 14/403,491.
Non-Final Office Action dated Sep. 1, 2015, in U.S. Appl. No. 13/612,954.
Non-Final Office Action dated Sep. 11, 2015, in U.S. Appl. No. 13/612,925.
Non-Final Office Action dated Sep. 4, 2015, in U.S. Appl. No. 13/612,995.
Non-Final Office Action dated Sep. 6, 2016, in U.S. Appl. No. 14/335,135.
Nookaraju et al., "Molecular approaches for enhancing sweetness in fruits and vegetables," Scientia Horticulture, 127:1-15 (2010).
Nord-Larsen et al., "Cloning, characterization and expression analysis of tonoplast intrinsic proteins and glutamine synthetase in ryegrass (*Lolium perenne*L.)," Plant Cell Reports, 28(10):1549-1562 (2009).
Nowak et al., "A new and efficient method for inhibition of RNA viruses by DNA interference," The FEBS Journal, 276:4372-4380 (2009).
Ongvarrasopone et al., "A Simple and Cost Effective Method to Generate dsRNA for RNAi Studies in Invertebrates," Science Asia, 33:35-39 (2007).
Orbovie et al., "Foliar-Applied Surfactants and Urea Temporarily Reduce Carbon Assimilation of Grapefruit Leaves," J. Amer. Hort. Sci., 126(4):486-490 (2001).
Ouellet et al., "Members of the Acetohydroxyacid Synthase Muligene Family of *Brassica napus* Have Divergent Patterns of Expression," The Plant Journal, Blackwell Scientific Publications, Oxford, GB, 2(3):321-330 (1992).
Palauqui et al., "Activation of systemic acquired silencing by localised introduction of DNA," Current Biology, 9:59-66 (1999.
Parera et al., "Dehydration Rate after Solid Matrix Priming Alters Seed Performance of Shrunken-2 Corn," J. Amer. Soc. Hort. Sci., 119(3):629-635 (1994).
Partial European Search Report dated Dec. 6, 2017, in European Patent Application No. 17181861.0.
Partial Supplementary European Search Report dated Mar. 2, 2015, in European Patent Application No. 12 831 494.5.

(56) References Cited

OTHER PUBLICATIONS

Partial Supplementary European Search Report dated Jan. 11, 2018, in European Patent Application No. 15812530.0.
Patent Examination Report No. 1 dated Feb. 8, 2016, in Australian Patent Application No. 2014262189.
Patent Examination Report No. 1 dated Jun. 17, 2016, in Australian Patent Application No. 2012308659.
Patent Examination Report No. 1 dated Jun. 17, 2016, in Australian Patent Application No. 2012308660.
Patent Examination Report No. 1 dated Jun. 8, 2017, in Australian Patent Application No. 2012308686.
Patent Examination Report No. 1 dated Nov. 11, 2013, in Australian Patent Application No. 2011224570.
Paungfoo-Lonhienne et al., "DNA is Taken up by Root Hairs and Pollen, and Stimulates Root and Pollen Tube Growth," Plant Physiology, 153:799-805 (2010).
Paungfoo-Lonhienne et al., "DNA uptake the expression of CLE peptides which control root morphology," Plant Signaling & Behavior, 5(9):1112-1114 (2010).
Pei et al., "On the art of identifying effective and specific siRNAs," Nature Methods, 3(9):670-676 (2006).
Pitino et al., "Silencing of Aphid Genes by dsRNA Feeding from Plants," *PLos ONE*, 6:e25709 (2011).
Pornprom et al., "Glutamine synthetase mutation conferring target-site-based resistance to glufosinate in soybean cell selections," Pest Manag Sci, 2009; 65(2):216-222 (2009).
Powles et al., "Evolution in Action: Plants Resistant to Herbicides," Annual Review of Plant Biology, 61(1):317-347 (2010).
Pratt et al., "Amaranthus rudis and *A. tuberculatus*, One Species or Two?," Journal of the Torrey Botanical Society, 128(3):282-296 (2001) Herewith.
Preston et al., "Multiple effects of a naturally occurring proline to threonine substitution within acetolactate synthase in two herbicide-resistant populations of Lactuca serriola," Physiol., 84(3):227-235 (2006).
Rakoczy-Trojanowska, "Alternative Methods of Plant Transformation—a short review," Cellular & Molecular Biology Letters, 7:849-858 (2002).
Reddy et a/."Organosilicone Adjuvants Increased the Efficacy of Glyphosate for Control of Weeds in Citrus (*Citrus* spp.)" HortScience 27(9):1003-1005 (1992).
Rey et al., "Diversity of Dicotyledenous-Infecting Geminiviruses and Their Associated DNA Molecules in Southern Africa, Including the South-West Indian Ocean Islands," Viruses, 4:1753-1791 (2012).
Reynolds et al., "Rational siRNA design for RNA interference," Nature Biotechnology, 22:326-330 (2004).
Richardson et al., "Targeting and assembly of components of the TOC protein import complex at the chloroplast outer envelope membrane," Frontiers in Plant Science, 5:1-14 (2014).
Riggins et al., "Characterization of de novo transcriptome for waterhemp (*Amaranthus tuberculatus*) using GS-FLX 454 pyrosequencing and its application for studies of herbicide target-site genes," Pest Manag. Sci., 66:1042-1052(2010).
Roberts, "Fast-track applications: The potential for direct delivery of proteins and nucleic acids to plant cells for the discovery of gene function," Plant Methods, 1(12):1-3 (2005).
Rothnie et al., Pararetroviruses and Retroviruses: A Comparative Review of Viral Structure and Gene Expression Strategies, Advances in Virus Research, 44:1-67 (1994).
Ryabov et al., "Cell-to-Cell, but Not Long-Distance, Spread of RNA Silencing That Is Induced in Individual Epidermal Cells," Journal of Virology, 78(6):3149-3154 (2004).
Salanenka et al.,"Seedcoat Permeability: Uptake and Post-germination Transport of Applied Model Tracer Compounds," HortScience, 46(4):622-626 (2011).
Sammataro et al., 'Some Volatile Plant Oils as Potential Control Agents for Varroa Mites (Acari: Varroidae) in Honey Bee Colonies (Hymenoptera: Apidae), *American Bee Journal*, 138(9):681-685 (1998).

Santosh et al., "RNA interference for the control of whiteflies (*Bemisia tabaci*) by oral route," Journal of Biosciences, 36(1):153-161 (2011).
Sathasivan et al., "Nucleotide sequence of a mutant acetolactate synthase gene from an imidazolinone-resistant *Arabidopsis thaliana* var. Columbia," Nucleic Acids Research, 18(8):2188-2193 (1990).
Schonherr, "Water Permeability of Isolated Cuticular Membranes: The Effect pH and Cations on Diffusion, Hydrodynamic Permeability and Size of Polar Pores in the Cutin Matrix," Planta, 128:113-126 (1976).
Schwab et al., "RNA silencing amplification in plants: Size matters," PNAS, 107(34):14945-14946 (2010).
Schweizer et al., "Double-stranded RNA interferes with gene function at the single-cell level in cereals," The Plant Journal, 24(6):895-903 (2000).
Scott et al., "Towards the elements of successful insect RNAi," Journal of Insect Physiology, 59(12):1212-1221 (2013).
Scott et al., Botanical Insecticides for Controlling Agricultural Pests: Piperamides and the Colorado Potato Beetle Leptinotarsa decemlineata Say (Coleoptera: Chiysomelidae), Archives of Insect Biochemistry and Physiology, 54:212-225 (2003).
Search Report dated Jul. 24, 2017, in Chinese Patent Application No. 201480014392.5 (with English translation).
Search Report dated Oct. 20, 2017, in Chinese Patent Application No. 201380039346.6.
Second Chinese Office Action dated Jun. 10, 2014, in Chinese Patent Application No. 201180012795.2.
Second Office Action dated Feb. 25, 2016, in Chinese Patent Application No. 201280054179.8.
Second Office Action dated Mar. 4, 2016, in Chinese Patent Application No. 201280054820.8.
Selvarani et al., "Evaluation of seed priming methods to improve seed vigour of onion (*Allium cepa* cv. Aggregatum) and carrot (*Daucus carota*)," Journal of Agricultural Technology, 7(3):857-867 (2011).
Senthil-Kumar et al., "A systematic study silencing in Nicotiana benthamiana and other Solanaceae species when heterologous gene sequences are used for virus-induced gene silencing," New Phytologist, 176:782-791 (2007).
Sharma et al., "A simple and efficient Agrobacterium-mediated procedure for transformation of tomato," J. Biosci., 34(3):423 433 (2009).
Shintani et al., "Antisense Expression and Overexpression of Biotin Carboxylase in Tobacco Leaves," Plant Physiol., 114:881-886 (1997).
Showalter, "Structure and Function of Plant Cell Wall Proteins," The Plant Cell, 5:9-23 (1993).
Sijen et al. "On the Role of RNA Amplification in dsRNA-Triggered Gene Silencing," Cell, 107:465-476 (2001).
Silwet L-77 Spray Adjuvant for agricultural applications, product description from Momentive Performance Materials, Inc. (2003).
Snead et al., "Molecular basis for improved gene silencing by Dicer substrate interfering RNA compared with other siRNA variants," Nucleic Acids Research, 41(12):6209-6221 (2013).
Song et al., "Herbicide," New Heterocyclic Pesticide, Chemical Industry Press, 354-356 (2011).
Statement of Grounds and Particulars dated Sep. 1, 2017, in Australian Patent No. 2014262189.
Stevens et al., "New Formulation Technology—Silwet® Organosilicone Surfactants Have Physical and Physiological Properties Which Enhance Performance of Sprays," Proceedings of the 9th Australian Weeds Conference, pp. 327-331 (1990).
Stevens, "Formulation of Sprays to Improve the Efficacy of Foliar Fertilisers," New Zealand Journal of Forestry Science, 24(1):27-34 (1994).
Stevens, "Organosilicone Surfactants as Adjuvants for Agrochemicals," Journal of Pesticide Science, 38:103-122 (1993).
Stock et al., "Possible Mechanisms for Surfactant-Induced Foliar Uptake of Agrochemicals," Pestic. Sci., 38:165-177 (1993).
Sudarsan et al., "Metabolite-binding RNA domains are present in the genes of eukaryotes," RNA, 9:644-647 (2003).
Summons to Attend Oral Proceedings Pursuant to Rule 115(1) EPC, dated Aug. 7, 2017, in European Patent Application No. 12832160.1.

(56) References Cited

OTHER PUBLICATIONS

Sun, "Characterization of Organosilicone Surfactants and Their Effects on Sulfonylurea Herbicide Activity," Thesis Submitted to the Faculty of the Virginia Polytechnic Institute and State University dated Apr. 5, 1996.
Supplementary European Search Report dated Jan. 17, 2018, in European Patent Application No. 15773480.7.
Supplementary Partial European Search Report dated Jan. 11, 2018 in European Appln. 15826865.
Supplementary Partial European Search Report dated Oct. 16, 2017, in European Patent Application No. 15773480.7.
Takasaki et al., "An Effective Method for Selecting siRNA Target Sequences in Mammalian Cells," Cell Cycle, 3:790-795 (2004).
Tang et al., "Efficient delivery of small interfering RNA to plant cells by a nanosecond pulsed laser-induced stress wave for post-transcriptional gene silencing," Plant Science, 171:375-381 (2006).
Tank Mixing Chemicals Applied to Peanut Crops: Are the Chemicals Compatible?, College of Agriculture & Life Sciences, NC State University, AGW-653, pp. 1-11 (2004).
Templeton et al., "Improved DNA: liposome complexes for increased systemic delivery and gene expression," Nature Biotechnology, 15:647-652 (1997).
Tenllado et al., "Crude extracts of bacterially expressed dsRNA can be used to protect plants against virus infection," BMC Biotechnology, 3(3):1-11 (2003).
Tenllado et al., "Double-Stranded RNA-Mediated Interference with Plant Virus Infection," Journal of Virology, 75(24):12288-12297 (2001).
Tenllado et al., "RNA interference as a new biotechnological tool for the control of virus diseases in plants," Virus Research, 102:85-96 (2004).
Tepfer, "Risk assessment of virus resistant transgenic plants," Annual Review of Phytopathology, 40:467-491 (2002).
Terenius et al., RNA interference in Lepidoptera: an overview of successful and unsuccessful studies and implications for experimental design, Journal of Insect Physiology, 57(2):231-245 (2011).
Third Party Submission filed Nov. 29, 2012 in U.S. Appl. No. 13/042,856.
Thomas et al., "Size constraints for targeting post-transcriptional gene silencing and for RNA-directed methylation in Nicotiana benthamiana using a potato virus X vector," The Plant Journal, 25(4):417-425 (2001).
Tian et al., "Developmental Control of a Lepidopteran Pest *Spodoptera exigua* by Ingestion of Bacteria Expressing dsRNA of a Non-Midgut Gene," PLoS One, 4:e6225, pp. 1-14 (2009).
Timmons et al., "Specific interference by ingested dsRNA," Nature, 395:854 (1998).
Tomari et al., "Perspective: machines for RNAi," Genes & Dev., 19:517-529 (2005).
Töpfer et al., "Uptake and Transient Expression of Chimeric Genes in Seed-Derived Embryos," Plant Cell, 1:133-139 (1989).
Toriyama et al., "Transgenic Rice Plants After Direct Gene Transfer Into Protoplasts," Bio/Technology, 6:1072-1074 (1988).
Tranel et al., "Resistance of weeds to ALS-inhibiting herbicides: what have we learned?," Weed Science, 50:700-712 (2002).
Tsugawa et al., "Efficient transformation of rice protoplasts mediated by a synthetic polycationic amino polymer," Theor Appl Genet, 97:1019-1026 (1998).
Turina et al., "Tospoviruses in the Mediterranean Area," Advances in Virus Research, 84:403-437 (2012).
Tuschl, "Expanding small RNA interference," Nature Biotechnol., 20: 446-448 (2002).
Ui-Tei et al., "Guidelines for the selection of highly effective siRNA sequences for mammalian and chick RNA interference," Nucleic Acids Res., 32(3): 936-948 (2004).
Ulrich et al., "Large scale RNAi screen in Tribolium reveals novel target genes for pest control and the proteasome as prime target," BMC genomics, 16(1):671 (2015).

Unnamalai et al., "Cationic oligopeptide-mediated delivery of dsRNA for post-transcriptional gene silencing in plant cells,". FEBS Letters, 566:307-310 (2004).
Unniraman et al., "Alternate Paradigm for Intrinsic Transcription Termination in Eubacteria," The Journal of Biological Chemistry, 276(45)(9):41850-41855 (2001).
Unniraman et al., "Conserved Economics of Transcription Termination in Eubacteria," Nucleic Acids Research, 30(3):675-684 (2002).
Upadhyay et al., RNA interference for the control of whiteflies (*Bemisia tabaci*) by oral route, J Biosci., 36(1):153-161 (2011).
Urayama et al., "Knock-down of OsDCL2 in Rice Negatively Affects Maintenance of the Endogenous dsRNA Virus, Oryza sativa Endornavirus," Plant and Cell Physiology, 51(1):58-67 (2010).
van de Wetering et al., "Specific inhibition of gene expression using a stably integrated, inducible small-interfering-RNA vector," EMBO Rep., 4(6):609-615 (2003).
Vasil et al., "Herbicide Resistant Fertile Transgenic Wheat Plants Obtained by Microprojectile Bombardment of Regenerable Embryogenic Callus," Bio/Technology,10:667-674 (1992).
Vaucheret, "Post-transcriptional small RNA pathways in plants: mechanisms and regulations," Genes Dev., 20:759-771 (2006).
Vencill et al., "Resistance of Weeds to Herbicides," Herbicides and Environment, 29:585-594 (2011).
Verma et al., "Modified oligonucleotides: synthesis and strategy for users," Annu. Rev. Biochem., 67:99-134 (1998).
Vermeulen et al., "The contributions of dsRNA structure to Dicer specificity and efficiency," RNA, 11(5):674-682 (2005).
Vert et al., "An accurate and interpretable model for siRNA efficacy prediction," BMC Bioinformatics, 7:520 (2006).
Voinnet et al., "Systemic Spread of Sequence-Specific Transgene RNA Degradation in Plants Is Initiated by Localized Introduction of Ectopic Promoterless DNA," Cell, 95:177-187 (1998).
Voinnet, "Origin, Biogenesis, and Activity of Plant MicroRNAs," Cell, 136:669-687 (2009).
Wakelin et al., "A target-site mutation is present in a glyphosate-resistant Lolium rigidum population," Weed Res. (Oxford), 46(5):432-440 (2006).
Walton et al., "Thermodynamic and Kinetic Characterization of Antisense Oligodeoxynucleotide Binding to a Structured mRNA," *Biophysical Journal*, 82:366-377 (2002).
Wan et al., "Generation of Large Numbers of Independently Transformed Fertile Barley Plants," Plant Physiol., 104:37-48 (1994).
Wang et al., "Principle and technology of genetic engineering in plants," in Plant genetic engineering principles and techniques, Beijing:Science Press, pp. 313-315 (1998).
Wang et al., "Silkworm Coatomers and Their Role in Tube Expansion of Posterior Silkgland," PLoS One5(10): E133252 (2010).
Wardell, "Floral Induction of Vegetative Plants Supplied a Purified Fraction of Deoxyribonucleic Acid from Stems of Flowering Plants," Plant Physiol, 60:885- 891 (1977) Herewith.
Wardell,"Floral Activity in Solutions of Deoxyribonucleic Acid Extracted from Tobacco Stems," Plant Physiol, 57:855-861 (1976).
Waterhouse et al., "Virus resistance and gene silencing in plants can be induced by simultaneous expression of sense and antisense RNA," Proc Natl Acad Sci Usa, 95 13959-13964 (1998).
Whyard et al., "Ingested double-stranded RNAs can act as species-specific insecticides," Insect Biochem. Mol. Biol., 39(11):824-832 (2009) Herewith.
Widholm et al., "Glyphosate selection of cultures of 3 plant species," Phyisologia gene amplification in suspension Plantarum, 112:540-545 (2001).
Wild Carrot Noxious Weed Control Board (NWCB) of Washington State (2010) <www.nwcb.wa.gov/detail.asp?weed=46>.
Wilson, et al., "Transcription termination at intrinsic terminators: The role of the RNA hairpin," Proc. Natl. Acad. Sci. USA, 92:8793-8797 (1995).
Winkler et al., "Thiamine derivatives bind messenger RNAs directly to regulate bacterial gene expression," Nature, 419:952-956 (2002).
Written Opinion dated Apr. 7, 2016, in Singapore Patent Application No. 201206152-9.
Written Opinion dated Mar. 6, 2017, in Singaporean Patent Application No. 2012061529.

(56) References Cited

OTHER PUBLICATIONS

Written Opinion dated Sep. 1, 2014, in Singapore Patent Application No. 201206152-9.
Yao et al., "Development of RNAi Methods for Peregrinus maidis, the Corn Planthopper," PLOS One, 8(8):1-11 (2013).
Yibrah et al., "Antisense Rna inhibition of uidA gene expression in transgenic plants: Evidence for interaction between first and second transformation events," Hereditas, 118:273-280 (1993).
Yin et al., "Production of double-stranded infection utilizing a bacterial prokaryotic RNA for interference with TMV expression system," Appl. Microbiol. Biotechnol., 84(2):323-333 (2009).
YouTube video by General Electric Company "Silwet Surfactants," screen shot taken on Jan. 11, 2012 of video of www.youtube.com/watch?v=WBw7nXMqHk8 (uploaded Jul. 13, 2009).
Zhang et al., "Agrobacterium-mediated transformation of *Arabidopsis thaliana* using the floral dip method," Nature Protocols, 1(2):1-6 (2006).
Zhang et al., "Transgenic rice plants produced by electroporation-mediated plasmid uptake into protoplasts," The Plant Cell Rep., 7:379-384 (1988).
Zhang, "Artificial trans-acting small interfering RNA: a tool for plant biology study and crop improvements," Planta, 239:1139-1146 (2014).
Zhang, Chapter 10: New Characteristics of Pesticide Research & Development, p. 209 (2010).
Zhao et al., "PsOr1, a potential target for RNA interference-based pest management," Insect Molecular Biology 20(1):97-104 (2011).
Zhu et al., "Ingested RNA interference for managing the populations of the Colorado potato beetle, Leptinotarsa decemlineata," Pest Manag Sci, 67:175-182 (2010).
Zotti et al., "RNAi technology for insect management and protection of beneficial insects from diseases: lessons, challenges and risk assessments," Neotropical Entomology, 44(3):197-213 (2015).
Alarcòn-Reverte et al., "Resistance to ACCase-Inhibiting Herbicides in the Weed Lolium Multiflorum," Comm. Appl. Biol. Sci, 73(4):899:902 (Sep. 2008).
Andersen et al., "Delivery of siRNA from lyophilized polymeric surfaces," Biomaterials, 29:506-512 (Oct. 2007).
Ascencio-Ibanez et al., "DNA abrasion onto plants is an effective method for geminivirus infection and virus-induced gene silencing," Journal of Virological Methods, 142:198-203 (Jul. 2007).
Database Accession No. EF219380, "SV 1; linear; mRNA; STD; VRL; 9499 BP.," pp. 1-5 (Feb. 2007).
Dietzl et al., "A genome-wide transgenic RNAi library for conditional gene inactivation in *Drosophila*," Nature, 448:151-157 (Jul. 2007).
Eudes et al., "Cell-penetrating peptides," Plant Signaling & Behavior, 3(8):549-5550 (Aug. 2008).

European Cooperation in the field of Scientific Cost and Technical Research—Memorandum of Understanding for COST Action FA0806 (Dec. 2008).
Gao et al., "Nonviral Methods for siRNA Delivery," Molecular Pharmaceutics, 6(3):651-658 (Dec. 2008).
Gomez-Zurita et al., "Recalibrated Tree of Leaf Beetles (*Chiysomelidae*) Indicates Independent Diversification of Angiosperms and Their Insect Herbivores," PLoS One, 4(e360):1-8 (Apr. 2007).
Katoh et al., "Specific residues at every third position of siRNA shape its efficient RNAi activity," Nucleic Acids Res., 35(4): e27 (Jan. 2007).
Liu et al., "Comparative study on the interaction of DNA with three kinds of surfactants and the formation of multilayer films," Bioelectrochemistry, 70:301-307 (May 2007).
Lu et al., "OligoWalk: an online siRNA thermodynamics," Nucleic Acids Research, design tool utilizing hybridization Previously Provided on Jul. 20, 2020.36:W104-W108 (May 2008).
Mao et al., "Silencing a cotton bollworm P450 monooxygenase gene by plant-mediated RNAi impairs larval tolerance of gossypol.," Nat Biotechnol., 25(11):1307-13 (Nov. 2007).
Masoud et al., "Constitutive expression an inducible β-1,3-glucanese in alfalfa reduces disease seveirty caused by the oomycete pathogen *Phytophthora megasperma*f. sp. medicanginis, but does not reduce disease severity of chitincontaining fungi," *Transgenic Research*, 5:313-323 (Sep. 1996).
Peretz et al., "A Universal Expression/Silencing Vector in Plants," Plant Physiology, 145:1251-1263 (Dec. 2007).
Pridgeon et al., "Topically Applied *AaeIAP1* Double-Stranded RNA Kills Female Adults of Aedes aegypti," *J Med. Entomol.*, 45(3):414-420 (May 2008).
Reddy et al., "Aminomethylphosphonic Acid Accumulation in Plant Species Treated with Glyphosate," J. Agric. Food Chem., 56(6):2125-2130 (Feb. 2008.
Sindhu et al., "Effective and specific in planta RNAi in cyst nematodes: expression interference of four parasitism genes reduces parasitic success," J. Exp. Botany, 60:315-324 (Nov. 2008).
Small, "RNAi for revealing and engineering plant gene functions," Current Opinion in Biotechnology, 18:148-153 (Feb. 2007).
Street, "Why is DNA (and not RNA) a stable storage form for genetic information?," Biochemistry Revisited, pp. 1-4 (Jan. 2008).
Wang et al., "Foliar uptake of pesticides-Present status and future challenge," ScienceDirect, 87:1-8 (Jan. 2007).
Wiesman et al., "Novel cationic vesicle platform derived from vernonia oil for efficient delivery of DNA through plant cuticle membranes," Journal of Biotechnology, 130:85-94 (Jan. 2007).
Zhao et al., "Phyllotreta striolata (Coleoptera: Chrysomelidae):Arginine kinase): cloning and RNAi-based pest control," European Journal of Entomology, 105(5):815-822 (Dec. 2008).
Zrachya et al., "Production of siRNA targeted against TYLCV coat protein transcripts leads to silencing of its expression and resistance to the virus," Transgenic Res., 16:385-398 (Jun. 2007).

* cited by examiner

CB  Q

Q

COMPOSITIONS FOR CONFERRING TOLERANCE TO VIRAL DISEASE IN SOCIAL INSECTS, AND THE USE THEREOF

RELATED APPLICATION

This application is a continuation of U.S. patent application Ser. No. 13/332,430, filed on Dec. 21, 2011, which is a continuation of U.S. patent application Ser. No. 12/222,949, filed on Aug. 20, 2008, now U.S. Pat. No. 8,097,712, which claims the benefit of priority from U.S. Provisional Patent Application No. 60/996,244, filed on Nov. 7, 2007. The contents of the above applications are all incorporated herein by reference.

SEQUENCE LISTING STATEMENT

The ASCII file, entitled 55167SequenceListing.txt, created on Jun. 30, 2013, comprising 11,657,409 bytes, submitted concurrently with the filing of this application is incorporated herein by reference.

FIELD AND BACKGROUND OF THE INVENTION

The invention relates to compositions and methods for reducing susceptibility to infectious disease in bees using RNA interference technology, and more particularly, to the use of dsRNA for prevention and treatment of viral infections in honeybees.

Colony Collapse Disorder

The importance of honeybees and other pollinating insects to the global world economy far surpasses their contribution in terms of honey production. The United States Department of Agriculture (USDA) estimates that every third bite we consume in our diet is dependent on a honeybee to pollinate that food. The total contribution of pollination in terms of added value to fruit crops exceeds $15 billion per annum, with indirect potential consequence of $75 billion dollars.

Viral Diseases in Honeybees

The health and vigor of honeybee colonies are threatened by numerous parasites and pathogens, including viruses, bacteria, protozoa, and mites, each with characteristic modes of transmission.

In general, transmission of viruses can occur via two pathways: horizontal and vertical transmission. In horizontal transmission, viruses are transmitted among individuals of the same generation, while vertical transmission occurs from adults to their offspring. Transmission can occur through multiple routes in social organisms (for a detailed review see Chen Y P, et al (2006) Appl Environ Microbiol. 72(1):606-11). Recently, horizontal transmission of honeybee viruses has been documented in bee colonies, for example, transmission of deformed wing virus (DWV) and Kashmir Bee Virus (KBV) by the parasitic mite Varroa destructor, as well as some evidence of virus in honeybee eggs and young larvae, life stages not parasitized by Varroa mites. Vertical transmission of multiple viruses from mother queens to their offspring in honeybees has also been recently demonstrated, as well as viruses in feces of queens, suggesting a role for feeding in virus transmission. Moreover, honeybee viruses have been detected in tissues of the gut, suggesting that viruses could be ingested by queens from contaminated foods and passed into the digestive tract, which then acts as a major reservoir for viral replication. Indeed, viruses might penetrate the gut wall and move into the insect hemocoel, spreading infections to other tissues.

In honeybees viruses often persist as latent infections. Thus, group living activities such as trophylaxis and nurse bee brood feeding, can potentially drive high levels of horizontal transmission or amplification of existing infections.

Colony Collapse Disorder

Colony Collapse Disorder (CCD) of honeybees is threatening to annihilate U.S. and world agriculture. Indeed, in the recent outbreak of CCD in the U.S in the winter of 2006-2007, an estimated 25% or more of the 2.4 million honeybee hives were lost because of CCD. An estimated 23% of beekeeping operations in the United States suffered from CCD over the winter of 2006-2007, affecting an average of 45% of the beekeepers operations. In the winter of 2007-2008, the CCD action group of the USDA-ARS estimated that a total of 36% of all hives from commercial operations were destroyed by CCD.

CCD is characterized by the rapid loss from a colony of its adult bee population, with dead adult bees usually found at a distance from the colony. At the final stages of collapse, a queen is attended only by a few newly emerged adult bees. Collapsed colonies often have considerable capped brood and food reserves. The phenomenon of CCD was first reported in 2006; however, beekeepers noted unique colony declines consistent with CCD as early as 2004. Various factors such as mites and infectious agents, weather patterns, electromagnetic (cellular antennas) radiation, pesticides, poor nutrition and stress have been postulated as causes. To date, control of CCD has focused on varroa mite control, sanitation and removal of affected hives, treating for opportunistic infections (such as Nosema) and improved nutrition. No effective preventative measures have been developed to date.

That CCD is due to the introduction of a previously unrecognized infectious agent is supported by preliminary evidence that CCD is transmissible through the reuse of equipment from CCD colonies and that such transmission can be broken by irradiation of the equipment before use.

Recently, Israeli acute paralysis virus of bees (IAPV, SEQ ID NO: 6), was strongly correlated with CCD. Indeed, Table 1 below shows that although other etiological agents of diseases in honeybees were found in CCD colonies, many were also found in apparently healthy, asymptomatic operations. In contrast, IAPV was not only found in 83% of CCD colonies, but was almost completely absent from apparently healthy colonies.

TABLE I

Analysis of bees tested for pathological candidates in CCD and non-CCD operations

| Agent | CCD (n = 30) | Non-CCD (n = 21) | Total (n = 51) | Positve predictive value (%) |
|---|---|---|---|---|
| IAPV | 25 (83.3%) | 1 (4.8%) | 26 (51.0%) | 96.1 |
| KBV | 30 (100%) | 16 (76.2%) | 46 (90.2%) | 65.2 |
| N. apis | 27 (90%) | 10 (47.6%) | 37 (72.5%) | 73.0 |
| N. ceranae | 30 (100%) | 17 (80.9%) | 47 (92.1%) | 63.8 |
| All four agents | 23 (76.7%) | 0 (0%) | 23 (45.0%) | 100 |

IAPV—Israel Acute Paralysis Virus;
KBV—Kashmir Bee Virus;
N. apis—Nosema apis;
N. ceranae—Nosema ceranae.
From: Diana L. Cox-Foster et al. (2007) A Metagenomic Survey of Microbes in Honey Bee Colony Collapse Disorder; Science 318: 283-286.

Moreover, it was recently shown that when injected or fed to the bees, IAPV causes paralysis and death in 98% of bees within days, further confirming IAPV as the infective agent in CCD.

Israeli acute paralysis virus (IAPV) has been characterized as a bee-affecting dicistrovirus. Recently, DNA versions of genomic segments of non-retro RNA viruses have been found in their respective host genomes, and the reciprocal exchange of genome sequences between host and virus has been demonstrated (Maori et al. Virology 2007; 362:342). These authors showed that the bees who harbored integrated viral sequences were found to be resistant to subsequent viral infection, and a RNAi mechanism of resistance was postulated. Most recently, as shown in Table 1 above, a metagenomic survey has indicated a close association between CCD and IAPV (Cox-Foster et al., Science, 2007; 318:283).

It thus follows that prevention of IAPV infection may prevent development of CCD, significantly improving the state of the beekeeping industry and world agriculture. The United States Department of Agriculture has developed an urgent action plan intended to cover all aspects of bee management to combat CCD and avoid future threats to honeybee management. They seek to maintain bees with resistance to parasites and pathogens and develop new methods of managing parasites and pathogens (see "CCD_actionplan" at the USDA website). However, no specific measures have been recommended, other than improving general sanitation, nutrition and combating opportunistic infections.

Methods for Silencing Using siRNAs/dsRNA

RNA interference (dsRNA and siRNA) has been shown effective in silencing gene expression in a broad variety of species, including plants, with wide ranging implications for cancer, inherited disease, infectious disease in plants and animals. It was also shown in a variety of organisms that dsRNA or their siRNA derivatives can be used to arrest, retard or even prevent a variety of pathogens, most notably viral diseases (see, for example, WO/2003/004649 to Tenllado et al).

It has been shown in some species that RNAi mediated interference spreads from the initial site of dsRNA delivery, producing interference phenotypes throughout the injected animal. Recently the same spreading effect of dsRNA has been demonstrated in bee larva, as well as detection of SID transmembrane channels considered responsible for endocytic uptake and spreading effect of dsRNA in humans, mouse and *C. elegans* (Aronstein et al, J. Apic Res and Bee World, 2006; 45:20-24).

Application of interference RNA technology for insects that are plant pests and other plant pests has been suggested. Moderate RNAi-type silencing of insect genes by feeding has been demonstrated (Turner et al., Insect Mol Biol 2006; 15:383; and Araujo et al., Insect Mol. Biol 2006; 36:683). dsRNA absorbance via honey has also been demonstrated (Aronstein et al., J Apiculture Res Bee World 2006; 45:20-24).

U.S. Pat. No. 6,326,193 refers to the use of recombinant insect viruses such as baculoviruses expressing dsRNA to silence selected insect genes for pest control. PCT application WO 99/32619 describes generally that dsRNA may be used to reduce crop destruction by other plant pathogens or pests such as arachnids, insects, nematodes, protozoans, bacteria, or fungi. PCT patent application WO 2004/005485 describes the use of vectors comprising sequences designed to control plant-parasitic nematodes by RNA interference, and transgenic plants transformed with such vectors. US patent application 20030180945 generally describes chimeric genes capable of producing antisense or sense RNA equipped with a prokaryotic promoter suitable for expression of the antisense or sense RNA in a particular prokaryotic host.

US Patent Application 20030154508 describes a method for pest control comprising exposing said pest to a compound (dsRNA) which disrupts, within said pest, a cation-amino acid transporter/channel protein.

PCT patent application WO 02/14472 describes methods for inhibiting target gene expression in a sucking insect, by expressing in a cell a nucleic acid construct comprising an inverted repeat and a sense or antisense region having substantial sequence identity to a target gene, wherein the inverted repeat is unrelated to the target gene. US patent application 20030150017 describes the use of RNA molecules homologous or complementary to a nucleotide sequence of a plant pest such as nematodes and insects.

Raemakers et al (PCT Applications WO 2007/080127 and WO 2007/080126) have disclosed transgenic plants expressing RNAi for controlling pest infestation by insects, nematodes, fungus and other plant pests. Among the sequences taught are sequences targeting essential genes of insects, including the honeybee. Waterhouse et al (US Patent Application 2006 0272049) also disclosed transgenic plants expressing dsRNA, and dsRNA directed to essential genes of plant insect pests, for use as insecticides, particularly against sap-sucking insects such as aphids. Boukharov et al. (US Patent Application 2007 0250947) disclosed constructs for expressing dsRNA in transgenic plants for targeting plant parasitic nematodes, specifically the soybean cyst nematode. While expression and processing of dsRNA were demonstrated, no actual inhibition of infestation with the dsRNA was shown.

SUMMARY OF THE INVENTION

According to some aspects of some embodiments, the present invention provides methods and compositions for preventing the spread of insect epidemics, such as Colony Collapse Disorder through the application of RNA interference technology directed to bee infectious organisms and agents, such as IAPV, Acute Bee Paralysis Virus and Kashmir Bee Paralysis Virus.

According to an aspect of some embodiments of the present invention there is provided an isolated nucleic acid agent comprising a nucleic acid sequence downregulating expression of a gene product of a bee pathogen.

According to another aspect of some embodiments of the present invention there is provided a nucleic acid agent comprising a nucleic acid sequence complementary to at least 21 nucleotides of a bee pathogen specific RNA and capable of inducing degradation of the bee pathogen specific RNA.

According to another aspect of some embodiments of the invention, there is provided a nucleic acid construct comprising a nucleic acid sequence encoding the isolated nucleic acid downregulating expression of a gene product of a bee pathogen.

According to some embodiments of the invention, the gene product is a mRNA encoding a polypeptide of the bee pathogen.

According to some embodiments of the invention, the agent is selected from the group consisting of a dsRNA, an hnRNA, an antisense RNA and a ribozyme.

According to some embodiments of the invention, the nucleic acid sequence is greater than 15 base pairs in length.

According to some embodiments of the invention, the nucleic acid sequence is greater than 30 base pairs in length.

According to some embodiments of the invention, the nucleic acid sequence is 19 to 25 base pairs in length.

According to some embodiments of the invention, the bee pathogen is selected from the group consisting of a virus, a bacteria, a parasitic protozoan, a fungus and a nematode.

According to some embodiments of the invention, the bee pathogen is a virus.

According to some embodiments of the invention, the virus is Israel Acute Paralysis Virus.

According to some embodiments of the invention, the virus is Kashmir Paralysis Virus.

According to some embodiments of the invention, the virus is Israel Acute Paralysis Virus and said polypeptide of said virus is selected from the group consisting of IAPV polymerase polyprotein (SEQ ID NO: 51) and IAPV structural polyprotein (SEQ ID NO: 52).

According to some embodiments of the invention, the viral pathogen is Israel Acute Paralysis Virus and said nucleic acid sequence is as set forth in SEQ ID NO: 6.

According to some embodiments of the invention, the viral pathogen is Israel Acute Paralysis Virus and said nucleic acid sequence is as set forth in SEQ ID NO: 33 and 34.

According to some embodiments of the invention, the virus is Israel Acute Paralysis Virus, and the nucleic acid sequence is a viral nucleic acid sequence detected in honeybee nucleic acid following Israel Acute Paralysis Virus infection.

According to another aspect of some embodiments of the present invention there is provided a bee-ingestible composition comprising the nucleic acid agent comprising a nucleic acid sequence downregulating expression of a gene product of a bee pathogen or a nucleic acid construct comprising the nucleic acid agent.

According to some embodiments of the invention the bee-ingestible composition is in solid form.

According to some embodiments of the invention, the composition is in liquid form.

According to some embodiments of the invention, the composition comprises protein.

According to some embodiments of the invention, the protein is in the form of pollen and/or soy patties.

According to some embodiments of the invention, the liquid is a sucrose solution.

According to some embodiments of the invention, the liquid is a corn syrup solution.

According to some embodiments of the invention the liquid further comprises a carbohydrate or sugar supplement.

According to an aspect of some embodiments of the present invention there is provided a method for increasing the tolerance of a bee to a disease caused by a pathogen comprising feeding the bee an effective amount of the nucleic acid agent comprising a nucleic acid sequence downregulating expression of a gene product of a bee pathogen or a nucleic acid construct comprising the nucleic acid agent, thereby increasing the tolerance of the bee to the pathogen.

According to a further aspect of some embodiments of the present invention there is provided a method for increasing the tolerance of a bee colony to a disease caused by a pathogen comprising feeding bees of the colony an effective amount of the nucleic acid agent comprising a nucleic acid sequence downregulating expression of a gene product of a bee pathogen or a nucleic acid construct comprising the nucleic acid agent, thereby increasing the tolerance of the colony to the pathogen.

According to some embodiments of the invention the bee is a honeybee.

According to some embodiments of the invention the honeybee is a forager.

According to some embodiments of the invention the honeybee is a hive bee.

According to some embodiments of the invention the disease is Colony Collapse Disorder.

According to some embodiments of the invention the bee pathogen is Israel Acute Paralysis Virus.

According to some embodiments of the invention the feeding comprises providing a liquid bee-ingestible composition.

According to some embodiments of the invention the feeding comprises providing a solid bee-ingestible composition.

According to an aspect of some embodiments of the present invention there is provided a method of increasing the tolerance of bees to Colony Collapse Disorder (CCD), the method comprising feeding to the honeybee hive an effective amount of double stranded ribonucleic nucleic acid (RNA), said double stranded RNA being homologous to a contiguous sequence of at least 21 nucleotides of Israel Acute Paralysis Virus.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A and 2B show bees of hives exposed to dsRNA following feeding with IAPV-specific dsRNA (1 µg/bee/feeding), 3 days prior to (FIG. 2A) and 8 days following (FIG. 2B) IAPV exposure (0.01 µgram/µl in sucrose solution). FIGS. 2C and 2D show bees of hives exposed to dsRNA following feeding with non-specific dsRNA (1 µg/bee/feeding), 3 days prior to (FIG. 2C) and 8 days following (FIG. 2D) IAPV exposure (0.01 µgram/µl in sucrose solution). FIGS. 2E and 2F show bees of hives exposed only to IAPV infection, without feeding with IAPV-specific dsRNA (FIG. 2E) three days before and 8 days following (FIG. 2F) IAPV exposure (0.01 µgram/µl in sucrose solution). FIGS. 2B, 2D and 2F show the effects of exposure to IAPV, eight days following exposure to IAPV. "Q" indicates queens, and "CB" indicates capped brood. Note the superior survival of the bees exposed to the IAPV-specific dsRNA, as compared with the decline of the unprotected colonies:

FIG. 4A represent PCR products with IAPV-specific primers (SEQ ID NOs. 35 and 36). Arrow indicates migration of 180 bp IAPV product. FIG. 4B represents PCR products with actin-specific primers, as an internal positive control (SEQ ID Nos. 37 and 38). Arrow indicates migration of 500 bp actin product. FIG. 4C represents PCR performed without reverse transcriptase. Absence of products indicates the absence of DNA in the template. Total RNA was extracted (8 days following inoculation with IAPV) from bee samples as follows: Lanes 1 and 2—IAPV-dsRNA treatment followed by IAPV inoculation; Lane 3—GFP-dsRNA treatment followed by IAPV inoculation; Lane 4—no dsRNA followed by IAPV inoculation; Lane 5—no dsRNA, no virus inoculated; Lane 6—negative control without template RNA. Lane M is molecular weight markers;

FIG. 11A illustrates the presence of IAPV-specific siRNA at 7 days and the end of the experiment. Lanes 1-6, Day 7: Lane 1—positive control IAPV-specific siRNA; lane 2—blank negative control; lane 3—untreated control bees; lane 4—bees fed with IAPV-specific dsRNA but no virus challenge; lane 5—bees challenged with IAPV, no dsRNA; lane 6—IAPV-specific dsRNA plus IAPV infection. Lanes 7-10, end of Experiment (Day 42): Lane 7—untreated control bees; lane 8—bees fed with IAPV-specific dsRNA but no virus challenge; lane 9—bees challenged with IAPV, no dsRNA; lane 10—IAPV-specific dsRNA plus IAPV infection.

FIG. 11B illustrates the presence of IAPV-specific siRNA at the start (0 days) and the end of the experiment. Lanes 1-4, Day 0: Lane 1—untreated control bees; lane 2—bees fed with IAPV-specific dsRNA but no virus challenge; lane 3—bees challenged with IAPV, no dsRNA; lane 4—IAPV-specific dsRNA plus IAPV infection. Lane 5—blank control. Lanes 6-9, end of Experiment (Day 42): Lane 6—untreated control bees; lane 7—bees fed with IAPV-specific dsRNA but no virus challenge; lane 8—bees challenged with IAPV, no dsRNA; lane 9—IAPV-specific dsRNA plus IAPV infection. Arrow indicates 21 bp RNAi fragment. Note the amplification of IAPV-specific RNAi in treated bees exposed to IAPV infection for a period of time (FIG. 11A, lanes 6 and 10; FIG. 11B, lane 9);

DESCRIPTION OF EMBODIMENTS OF THE INVENTION

Figure 1:
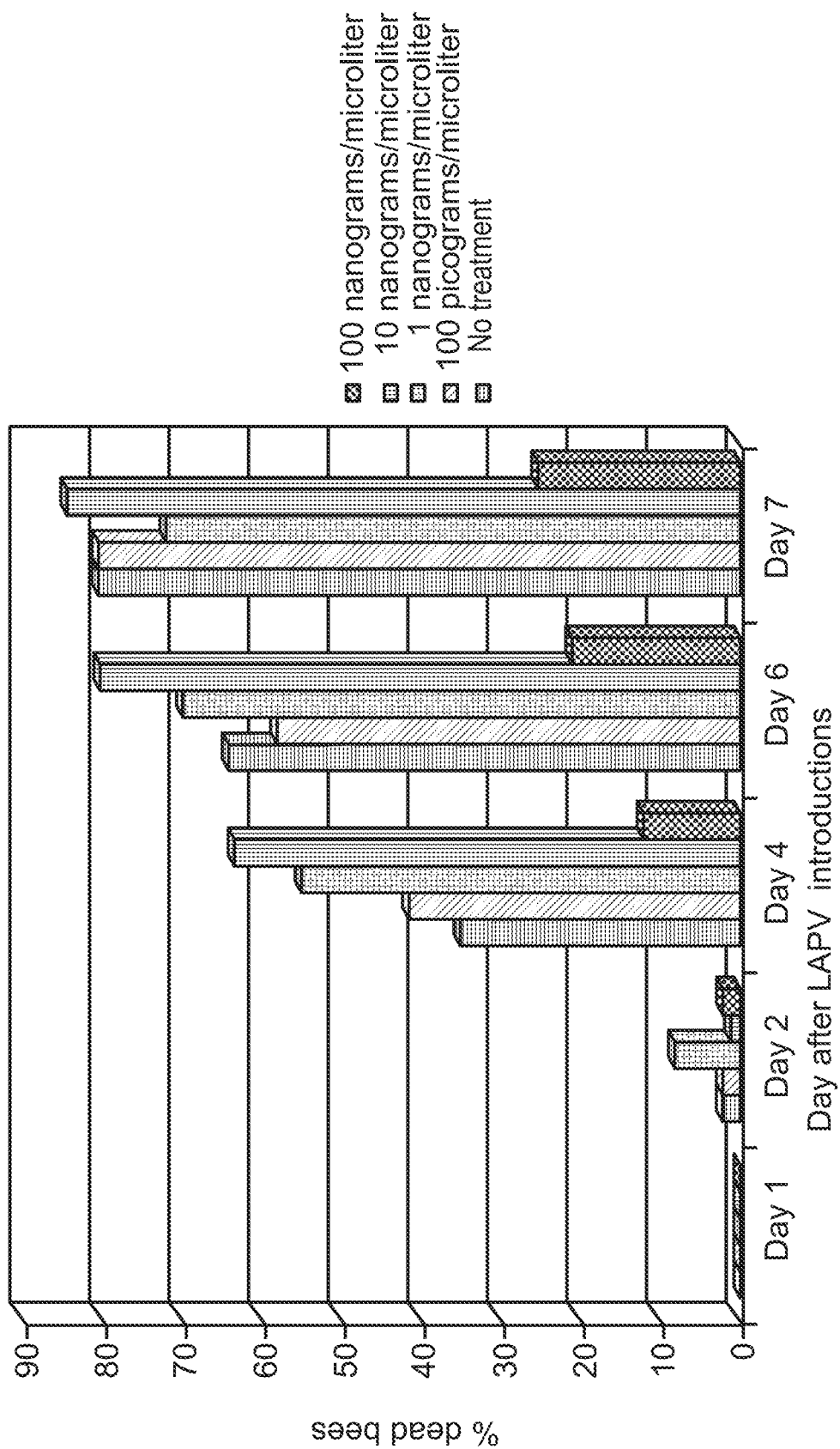
FIG. 1 is a histogram showing the effect of IAPV titer on bee mortality. 30 or 50 bees were exposed to increasing concentrations of IAPV in a 50% sucrose solution, in increasing doses (900 µl of 0.0001 to 0.1 microgram/ microliter virus particles). Vertical striped bars-100 ng/µl; Cross-hatched bars-10 ng/µl; Stippled bars-1.0 ng/µl; Horizontal striped bars-0.1 ng/µl. Controls (checkered bars) received sucrose without added virus. Dead bees in the containers were counted daily, and the total number of dead bees was calculated as a percentage of the initial number of bees introduced into the container at indicated days.
Figure 2A:
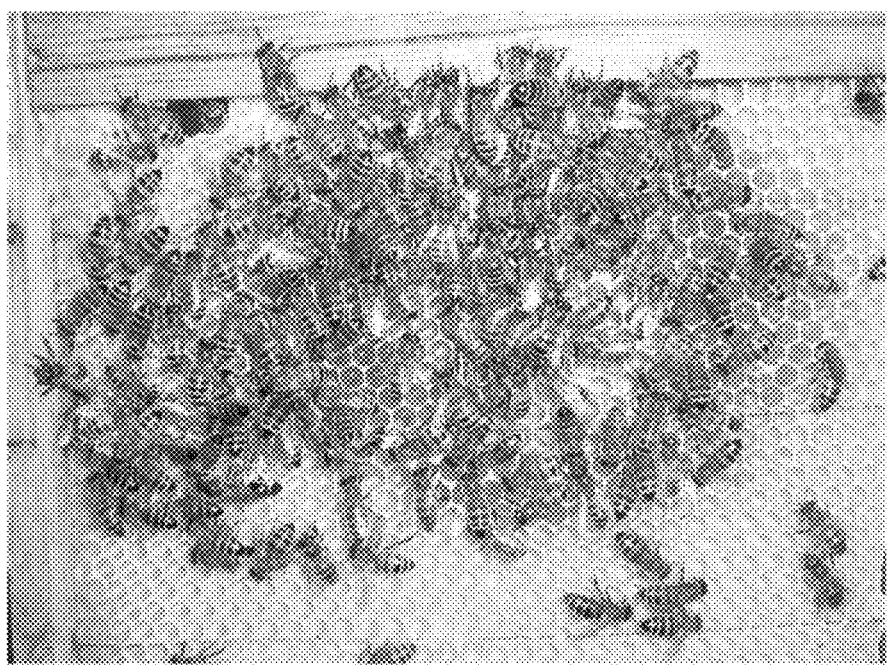
FIGS. 2A-2F are photographs showing the effect feeding IAPV-specific dsRNA on colonies exposed to IAPV infection.
Figure 2B:
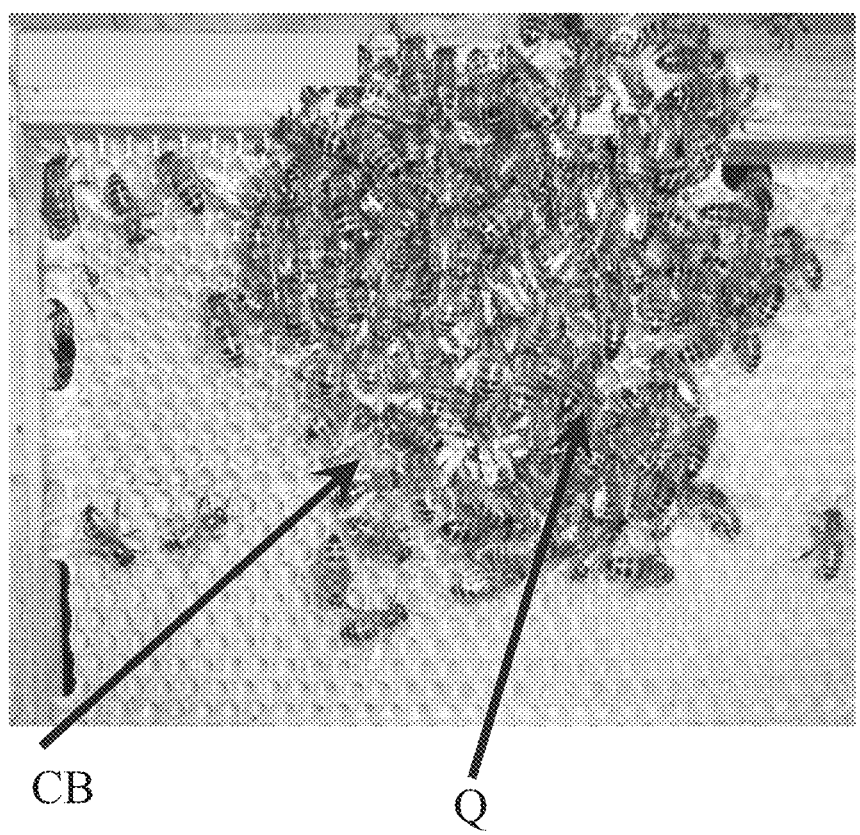
Figure 2C:
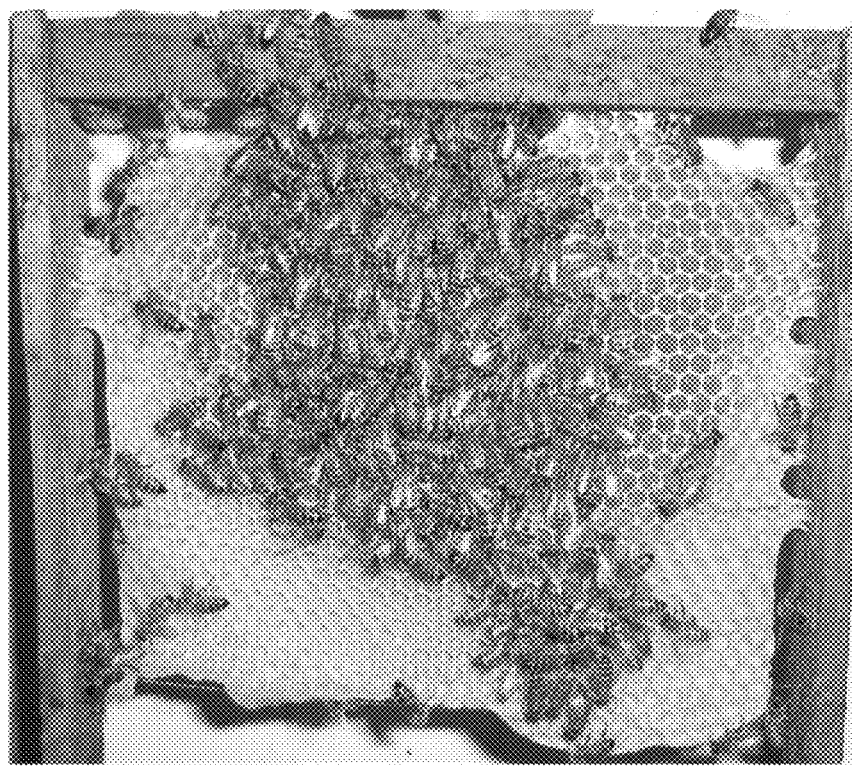
Figure 2D:
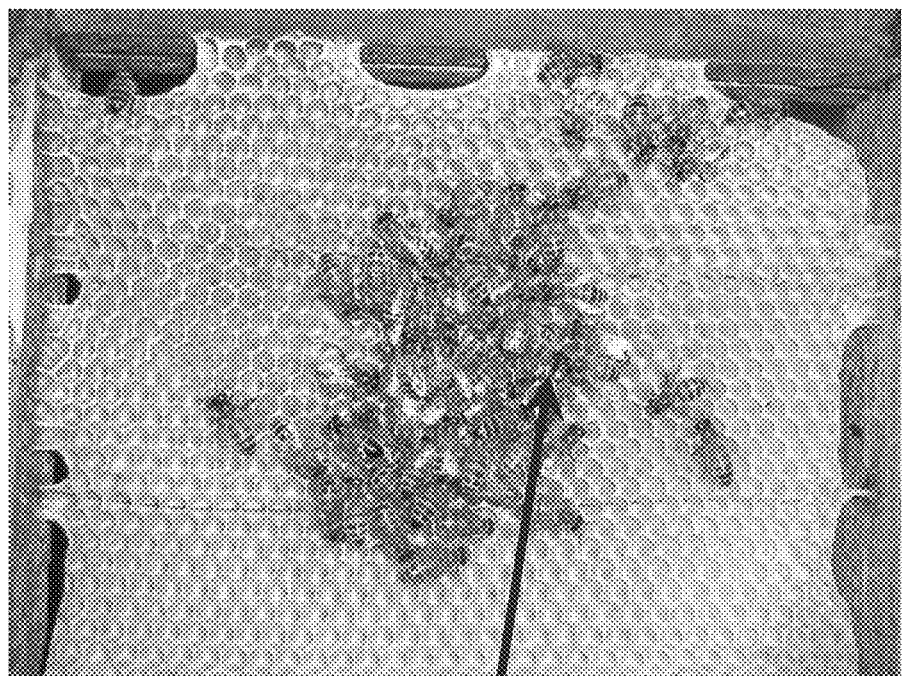
Figure 2E:
Figure 2F:
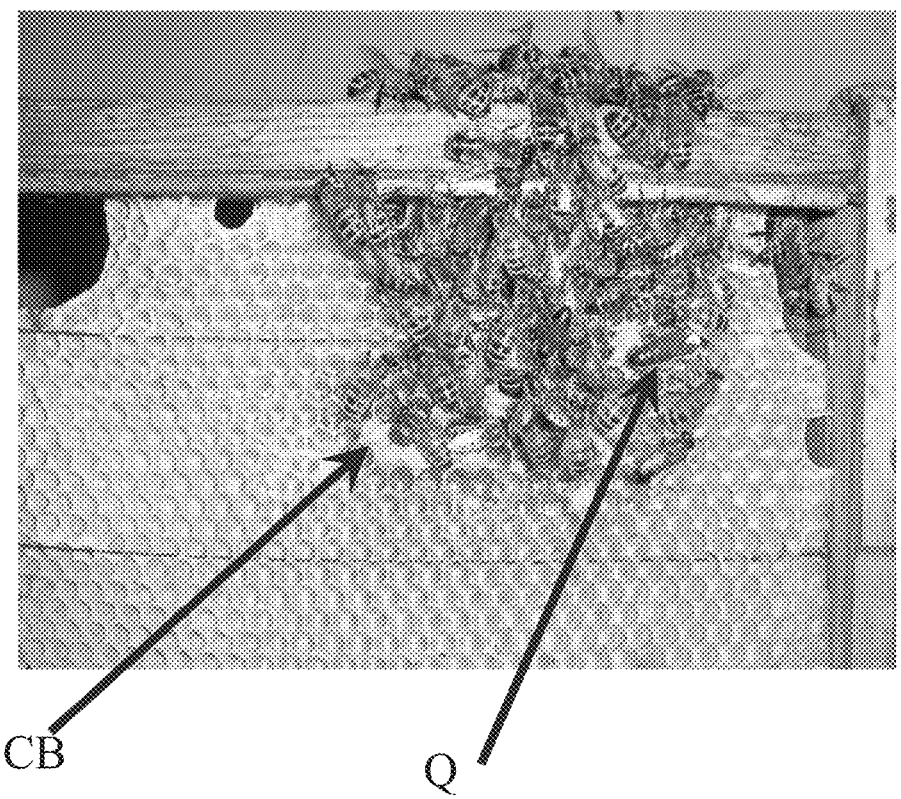

The present invention, in some embodiments thereof, relates to methods and compositions for reducing the susceptibility of bees to pathogenic organisms and, more particularly, but not exclusively, to methods for increasing the tolerance to viral diseases, such as Colony Collapse Disorder, by feeding viral-specific dsRNA.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While reducing the present invention to practice, the inventors have shown that ingestion by a bee of compositions containing one or more dsRNA molecules, wherein at least one segment of the dsRNA molecule corresponds to a substantially identical segment of RNA produced by a bee pathogen, will result in reduced incidence and severity of infection, and greatly enhanced survival of the bees and the colony overall. These results indicate that a polynucleotide molecule, either DNA or RNA, derived from a bee pathogen sequence can be used to design a nucleic acid agent or nucleic acid construct according to the methods of the present invention to produce one or more RNA sequences that can form into a dsRNA molecule available for ingestion by bees when provided by feeding. While reducing to practice, it was shown that bee colonies exposed to IAPV-specific dsRNA in their feed endured IAPV infection with greater survival (see FIG. 3) and lower incidence of infected bees than untreated colonies (see FIGS. 2E, 2F and 3, 4A-4C and 5). In colonies treated with a non-specific dsRNA mortality and incidence of infection was similar to that in untreated colonies (see FIGS. 2C, 2D, 3-5).

Thus, according to one embodiment of the present invention there is provided a method for increasing the tolerance of a bee to a disease caused by a pathogen comprising feeding the bee an effective amount of an isolated nucleic acid agent comprising a nucleic acid sequence downregulating expression of a polypeptide of a bee pathogen, or a nucleic acid construct comprising the nucleic acid sequence, thereby increasing the tolerance of the bee to the pathogen.

As used herein, the term "bee" is defined as any of several winged, hairy-bodied, usually stinging insects of the superfamily Apoidea in the order Hymenoptera, including both solitary and social species and characterized by sucking and chewing mouthparts for gathering nectar and pollen. Exemplary bee species include, but are not limited to *Apis, Bombus, Trigona, Osmia* and the like. In one embodiment, bees include, but are not limited to bumblebees (*Bombus terrestris*) and honeybees (*Apis mellifera*).

As used herein, the term "colony" is defined as a population of dozens to typically several tens of thousand honeybees that cooperate in nest building, food collection, and brood rearing. A colony normally has a single queen, the remainder of the bees being either "workers" (females) or "drones" (males). The social structure of the colony is maintained by the queen and workers and depends on an effective system of communication. Division of labor within the worker caste primarily depends on the age of the bee but varies with the needs of the colony. Reproduction and colony strength depend on the queen, the quantity of food stores, and the size of the worker force. Honeybees can also be subdivided into the categories of "hive bees", usually for the first part of a workers lifetime, during which the "hive bee" performs tasks within the hive, and "forager bee", during the latter part of the bee's lifetime, during which the "forager" locates and collects pollen and nectar from outside the hive, and brings the nectar or pollen into the hive for consumption and storage.

As used herein, the term "tolerance" is defined as the ability of a bee or bee colony to resist infestation by and/or proliferation of a pathogen, including, but not limited to, degree of infection, severity of symptoms, infectivity to other individuals (contagion), and the like. Tolerance can be assessed, for example, by monitoring infectivity, presence of symptoms or time course of a disease in a population following a challenge with the pathogen.

As used herein, the term "pathogen" is defined as a nucleic acid-containing agent capable of proliferation within the bee and/or bee colony, the pathogen causing disease in bees or bee colonies, especially, but not exclusively, a virus, a bacteria and a fungus. A bee or bee colony pathogenic agent can be an intracellular or extra-cellular parasite. According to one embodiment of the invention, the pathogen is a "bee pathogen", causing or facilitating a bee or bee colony disease, such as Colony Collapse Disorder, Sacbrood virus disease, Deformed Wing Disease, Cloudy Wing Disease, Chronic Paralysis, Nosemosis, American Foul Brood and the like.

As used herein, the terms "bee disease" or "bee colony disease" are defined as undesirable changes in the behavior, physiology, morphology, reproductive fitness, economic value, honey production, pollination capability, resistance to infection and/or infestation of a bee, a population of bees and/or a bee colony, directly or indirectly resulting from contact with a bee or bee colony pathogenic agent.

A non-limiting list of exemplary disease-causing pathogens, and diseases of bees and bee colonies associated with the pathogenic agents, suitable for treatment according to some embodiments of the methods and compositions of the present invention is found in Table II below. The complete genomes of several known isolates of IAPV and information on possible phylogenic relationships between strains that can be similarly targeted with the methods and compositions of the present invention are provided in Palacios et al. 2008 (published online ahead of print on 23 Apr. 2008, Journal of Virology)

TABLE II

Bee and Bee Colony Pathogens

| Parasitic Organism | Genes |
| --- | --- |
| Acute bee paralysis virus | Acute bee paralysis virus, complete genome. Accession NC_002548 (seq id no: 8) |
| Israel acute paralysis virus | Accession: NC_009025, israel acute paralysis virus of bees, complete genome (seq id no: 16) |
| Deformed wing virus | Deformed wing virus, complete genome. Accession NC_004830 (seq id no: 10) |
| Kashmir bee virus | Accession: AY275710, kashmir bee virus, complete genome (seq id no: 9) |
| Black queen cell virus | Black queen cell virus strain poland-6 non-structural polyprotein and structural polyprotein genes, complete cds. Accession: EF517521 (seq id no: 20) |
| Chronic paralysis virus | Chronic bee paralysis virus rna 2, complete sequence. Accession: NC_010712 (seq id no: 23) |
| Cloudy wing virus | Cloudy wing virus rna polymerase (pol) gene, partial cds. Accession AF034543 (seq id no: 7) |
| *Paenibacillus larvae* (American Foul Brood) | Accession: NZ_AARF01000646, whole genome (shotgun) sequenced. (seq id no: 11) |
| Melissococcus pluton (European Foul Brood) | Accession: EF666055 Melissococcus plutonius superoxide dismutase (soda) gene (seq id no: 21) |
| *Ascophaera apis* (Chalkbrood) | No genomic data |
| *Nosema apis*, | 1)Accession DQ996230 (seq id no: 15), *Nosema apis* RNA polymerase II largest subunit<br>2)Accesions EU545140 (seq id no: 22), EF584425 (seq id no: 19), EF584423 (seq id no: 18), EF584418 (seq id no: 17) all are 16S ribosomal RNA gene |
| *Nosema cerana* | EF091883 (seq id no: 12), EF091884 (seq id no: 13), and EF091885 (seq id no: 14) are accessions of 5S ribosomal RNA gene, intergenic spacer, and small subunit ribosomal RNA gene. |

While reducing the present invention to practice, the inventors have shown that providing a IAPV-specific dsRNA in the feed of bees exposed to IAPV dramatically reduced the incidence and levels of IAPV sequences detected in the bees, after 4 and 8 days (FIGS. 4A-4C and 5). Thus, in some embodiments of the present invention, the methods and compositions are useful for downregulating expression of a polypeptide of a bee or bee colony pathogenic organism.

As used herein, the term "downregulating expression" is defined as causing, directly or indirectly, reduction in the transcription of a desired gene, reduction in the amount, stability or translatability of transcription products (e.g. RNA) of said gene, reduction in translation of the polypeptide(s) encoded by the desired gene and/or reduction in the amount, stability, or alteration of biochemical function of the polypeptides encoded by the desired gene, so as to reduce the amount or function of the gene products. As used herein, "downregulating expression" also relates to reduction in amount, stability or translatability of bee pathogen RNA molecules in cells of a bee, where the bee pathogen genome is a single stranded RNA molecule, as in case of a single-stranded RNA virus. Downregulating expression of a gene or other bee pathogen RNA can be monitored, for example, by direct detection of gene transcripts (for example, by PCR), by detection of polypeptide(s) encoded by the gene or bee pathogen RNA (for example, by Western blot or immunoprecipitation), by detection of biological activity of polypeptides encode by the gene (for example, catalytic activity, ligand binding, and the like), or by monitoring changes in a cell or organism resulting from reduction in expression of a desired gene or bee pathogen RNA (for example, reduced proliferation of a pathogen, reduced virulence of a pathogen, reduced motility of a cell, reduced response of a cell or organism to stimulus, etc). As used herein, the downregulation can be transient, for example, for the duration of the presence of a downregulating agent, or permanent, resulting in reduction of gene expression or bee pathogen RNA for the lifetime of the organism and/or its future generations.

Downregulation of bee pathogen polypeptides can be effected on the genomic and/or the transcript level using a variety of molecules which interfere with transcription and/or translation (e.g., RNA silencing agents, Ribozyme, DNAzyme and antisense). Treatment and prevention of viral infections with dsRNA has been disclosed by WO/2003/004649 to Tenllado et al. Use of dsRNA in insects is disclosed in US Patent Application 2007 0250947, US Patent Application 2006 0272049, PCT Applications WO 2007/080127 and WO 2007/080126, US patent application 20030150017, PCT patent application WO 02/14472, US Patent Application 20030154508, PCT patent application WO 2004/005485, PCT application WO 99/32619 and U.S. Pat. No. 6,326,193.

Following is a list of agents capable of downregulating expression level and/or activity of bee pathogen polypeptides.

Downregulation of bee pathogen polypeptides can be achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene or bee pathogen RNA sequence. RNA silencing has been observed in many types of organisms, including plants, animals, and fungi.

As used herein, the term "RNA silencing agent" refers to an RNA which is capable of inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, the present invention contemplates use of dsRNA to downregulate protein expression from mRNA.

According to one embodiment, the dsRNA is greater than 30 bp. The use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

In one embodiment of the present invention, the dsRNA is greater than 30 base-pairs, and is as set forth in SEQ ID NOs: 24, 33 and 34.

Another method of downregulating bee pathogen proteins is by introduction of small inhibitory RNAs (siRNAs).

The term "siRNA" refers to small inhibitory RNA duplexes (generally between 18-30 basepairs, between 19 and 25 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of the present invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

According to another embodiment the RNA silencing agent may be a miRNA. miRNAs are small RNAs made from genes encoding primary transcripts of various sizes. They have been identified in both animals and plants. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the two strands being referred to as the miRNA (the strand that will eventually basepair with the target) The pre-miRNA is a substrate for a form of dicer that removes the miRNA duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) Genes & Development 18:2237-2242 and Guo et al. (2005) Plant Cell 17:1376-1386).

Unlike, siRNAs, miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728). A recent report (Hutvagner et al., 2002, Sciencexpress 297:2056-2060) hypothesizes that gene regulation through the miRNA pathway versus the siRNA pathway is determined solely by the degree of complementarity to the target transcript. It is speculated that siRNAs with only partial identity to the mRNA target will function in translational repression, similar to an miRNA, rather than triggering RNA degradation.

According to one embodiment of the present invention, the nucleic acid agent is capable of causing cleavage and/or degradation of a bee pathogen target polynucleotide sequence. As used herein, the phrases "target" or "target polynucleotide sequence" refer to any sequence present in a bee cell or in a bee, whether naturally occurring sequence or a heterologous sequence present due to an intracellular or extracellular pathogenic infection or a disease, which bee pathogen polynucleotide sequence has a function that is desired to be reduced or inhibited. The bee pathogen target sequence may be a coding sequence, that is, it is translated to express a protein or a functional fragment thereof. Alternatively, the target sequence may be non-coding, but may have a regulatory function. One target polynucleotide sequence is a bee pathogenic virus polynucleotide sequence necessary for replication and/or pathogenesis of the virus in an infected bee cell. Another embodiment of a bee pathogen target polynucleotide sequence is a non-expressed regulatory sequence of a virus-induced disease, which sequence is required for the maintenance of the virus in the bee cell, for example, a polynucleotide sequence of an intracellular or extracellular pathogen necessary for replication and/or pathogenesis of that pathogen in an infected bee. Yet another embodiment of a bee pathogenic target sequence is any sequence to which the nucleic acid agent, or sequences derived therefrom, is capable of binding, which binding results in cleavage and/or degradation ("silencing") of a bee pathogen polynucleotide. The term "gene" is intended to include any target sequence intended to be "silenced", whether or not transcribed and/or translated, including regulatory sequences, such as promoters, enhancers and other non-coding sequences.

In one embodiment of the present invention, synthesis of RNA silencing agents suitable for use with the present invention can be effected as follows. First, the bee pathogen polypeptide mRNA or other target sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www.ambion.com/techlib/tn/91/912.html).

Second, potential target sites are compared to an appropriate genomic database (e.g., human, mouse, rat etc.) using any sequence alignment software, such as the BLAST software available from the NCBI server (www.ncbi.nlm-.nih.gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene or sequence for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene or bee pathogen target sequence.

For example, a suitable bee pathogen siRNA can be an IAPV-specific siRNA corresponding to IAPV sequences SEQ ID NOs: 33 and 34. Additional suitable bee pathogen siRNAs can be designed according to sequences from any bee pathogens, for example, the sequences detailed in Table II, including, but not limited to Acute Bee Paralysis Virus (for example, SEQ ID NOs: 32430-41886), Deformed Wing Virus (for example, SEQ ID NOs: 9533-19652), Kashmir Bee Virus (for example, SEQ ID NOs: 42281-51771), Black Queen Cell Virus (for example, SEQ ID NOs: 19653-27934), Chronic Paralysis Virus (for example, SEQ ID NOs: 27935-30219), Cloudy Wing Virus (for example, SEQ ID NOs: 30220-30613), *Paenibacillus larvae* (for example, SEQ ID NOs: 30614-32007), *Melissococcus pluton* (for example, SEQ ID NOs: 32008-32429), *Nosema apis* (for example, SEQ ID NOs: 53774-56822) and *Nosema cerana* (for example, SEQ ID NOs: 51772-53773). Multiple beepathogen sequences can be designed to include sequences suitable for producing siRNAs effective against more than one bee pathogen, such as the multiple bee-virus dsRNA described in detail in Example IV herein (SEQ ID NO: 24). Such multiple bee-pathogen dsRNA can be of the long or short variety, and may include sequences corresponding to homologous sequences within a class of bee pathogens (multiple bee-virus sequences, for example), or sequences corresponding to diverse classes of pathogens (e.g. viral+bacterial+fungal sequences, etc). Further, multiple sequences can be designed to include two or more dsRNA sequences of the same bee-pathogen.

According to yet another embodiment of the present invention, synthesis of RNA silencing agents suitable for use with the present invention can be effected according to bee pathogen target sequences known to integrate into the host genome, target sequences suspected associated with resistance to a bee pathogen infection, target sequences representing intergenic regions of the bee pathogen genome and pathogen-specific sequences shown to be critical for pathogen growth and/or replication. It will be appreciated that, in a further embodiment of the present invention, nucleic acid agents targeted to sequences having a conserved homology between different strains of the bee pathogen, or even between diverse bee pathogens, once such sequences are identified, can be effective against more than one strain of the bee pathogen, or even against different bee pathogens.

It will be appreciated that the RNA silencing agent of the present invention need not be limited to those molecules containing only RNA, but further encompasses chemically-modified nucleotides and non-nucleotides.

In some embodiments, the RNA silencing agent provided herein can be functionally associated with a cell-penetrating peptide. As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of the present invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of the present invention preferably include, but are not limited to, penetratin, transportan, pIsl, TAT(48-60), pVEC, MTS, and MAP.

Another agent capable of downregulating a bee pathogen polypeptide is a DNAzyme molecule capable of specifically cleaving an mRNA transcript or DNA sequence of the bee pathogen polypeptide. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, LM [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 20002, Abstract 409, Ann Meeting Am Soc Gen Ther www.asgt.org). In another application, DNAzymes complementary to bcr-ab 1 oncogenes were successful in inhibiting the oncogenes expression in leukemia cells, and lessening relapse rates in autologous bone marrow transplant in cases of CML and ALL.

Downregulation of bee pathogen polypeptides or cleavage of bee pathogen RNA can also be effected by using an antisense polynucleotide capable of specifically hybridizing with an mRNA transcript encoding the bee pathogen polypeptide or a bee pathogen RNA target sequence.

Design of antisense molecules which can be used to efficiently downregulate a bee pathogen polypeptide must be effected while considering two aspects important to the antisense approach. The first aspect is delivery of the oligonucleotide into the cytoplasm of the appropriate cells, while the second aspect is design of an oligonucleotide which specifically binds the designated mRNA or RNA target sequence within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

For example, a suitable antisense oligonucleotide targeted against the IAPV mRNA would be of the sequences as set forth in SEQ ID NOs: 51 and 52 (IAPV polyproteins).

Several clinical trials have demonstrated safety, feasibility and activity of antisense oligonucleotides. For example, antisense oligonucleotides suitable for the treatment of cancer have been successfully used [Holmund et al., Curr Opin Mol Ther 1:372-85 (1999)], while treatment of hematological malignancies via antisense oligonucleotides targeting c-myb gene, p53 and Bcl-2 had entered clinical trials and had been shown to be tolerated by patients [Gerwitz Curr Opin Mol Ther 1:297-306 (1999)]. Antisense oligonucleotides targeted to nervous system proteins have been used effectively in honeybees (Fiala et al, J. Neuroscience 1999; 19:10125-34).

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Another agent capable of downregulating a bee pathogen polypeptide is a ribozyme molecule capable of specifically cleaving an mRNA transcript encoding a bee pathogen polypeptide. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA, including viral RNA, has rendered them valuable tools in both basic research and therapeutic applications. In the area of therapeutics, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

An additional method of regulating the expression of a bee pathogen polypeptide gene in cells is via triplex forming oligonucleotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

| | | | | |
|---|---|---|---|---|
| oligo | 3'--A | G | G | T |
| duplex | 5'--A | G | C | T |
| duplex | 3'--T | C | G | A |

However, it has been shown that the A-AT and G-GC triplets have the greatest triple helical stability (Reither and Jeltsch, BMC Biochem, 2002, Sep. 12, Epub). The same authors have demonstrated that TFOs designed according to the A-AT and G-GC rule do not form non-specific triplexes, indicating that the triplex formation is indeed sequence specific.

Thus for any given sequence in the bee pathogen polypeptide regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

The RNA, dsRNA, siRNA, or miRNA of the present invention may be produced chemically or enzymatically through manual or automated reactions or in vivo in an organism other than the plant for which pest control is intended. RNA may also be produced by partial or total organic synthesis. Any modified ribonucleotide can be introduced by in vitro enzymatic or organic synthesis. The RNA may be synthesized by a cellular RNA polymerase or a bacteriophage RNA polymerase (e.g., T3, T7, SP6). If synthesized chemically or by in vitro enzymatic synthesis, the RNA may be purified prior to feeding or formulated in an acceptable carrier and provided as a liquid, solid or semi-solid to the bees. For example, RNA can be purified from a mixture by extraction with a solvent or resin, precipitation, electrophoresis, chromatography, or a combination thereof. Alternatively, the RNA may be used with no, or a minimum of, purification to avoid losses due to sample processing. The RNA may be dried for storage or dissolved in an aqueous solution. The solution may contain buffers or salts to promote annealing, and/or stabilization of the duplex strands.

For transcription from a transgene in vivo or from an expression cassette, a regulatory region (e.g., promoter, enhancer, silencer, leader, intron and polyadenylation) may be used to modulate the transcription of the RNA strand (or strands). Therefore, in one embodiment, there is provided a nucleic acid construct comprising the nucleic acid agent. The nucleic acid construct can have polynucleotide sequences constructed to facilitate transcription of the RNA molecules of the present invention are operably linked to one or more promoter sequences functional in a host cell. The polynucleotide sequences may be placed under the control of an endogenous promoter normally present in the host genome. The polynucleotide sequences of the present invention, under the control of an operably linked promoter sequence, may further be flanked by additional sequences that advantageously affect its transcription and/or the stability of a resulting transcript. Such sequences are generally located upstream of the promoter and/or downstream of the 3' end of the expression construct. The term "operably linked", as used in reference to a regulatory sequence and a structural nucleotide sequence, means that the regulatory sequence causes regulated expression of the linked structural nucleotide sequence. "Regulatory sequences" or "control elements" refer to nucleotide sequences located upstream, within, or downstream of a structural nucleotide sequence, and which influence the timing and level or amount of transcription, RNA processing or stability, or translation of the associated structural nucleotide sequence. Regulatory sequences may include promoters, translation leader sequences, introns, enhancers, stem-loop structures, repressor binding sequences, termination sequences, pausing sequences, polyadenylation recognition sequences, and the like.

The nucleic acid agent can be delivered to the bees in a great variety of ways. As detailed herein, bee feeding is common practice amongst bee-keepers, for providing both nutritional and other, for example, supplemental needs. Bees typically feed on honey and pollen, but have been known to ingest non-natural feeds as well. Bees can be fed various foodstuffs including, but not limited to Wheast (a dairy yeast grown on cottage cheese), soybean flour, yeast (e.g. brewer's yeast, torula yeast) and yeast products products-fed singly or in combination and soybean flour fed as a dry mix or moist cake inside the hive or as a dry mix in open feeders outside the hive. Also useful is sugar, or a sugar syrup. The addition of 10 to 12 percent pollen to a supplement fed to bees improves palatability. The addition of 25 to 30 percent pollen improves the quality and quantity of essential nutrients that are required by bees for vital activity.

Cane or beet sugar, isomerized corn syrup, and type-50 sugar syrup are satisfactory substitutes for honey in the natural diet of honey bees. The last two can be supplied only as a liquid to bees.

Liquid feed can be supplied to bees inside the hive by, for example, any of the following methods: friction-top pail, combs within the brood chamber, division board feeder, boardman feeder, etc. Dry sugar may be fed by placing a pound or two on the inverted inner cover. A supply of water must be available to bees at all times. In one embodiment, pan or trays in which floating supports—such as wood chips, cork, or plastic sponge—are present are envisaged. Detailed descriptions of supplemental feeds for bees can be found in, for example, USDA publication by Standifer, et al 1977, entitled "Supplemental Feeding of Honey Bee Colonies" (USDA, Agriculture Information Bulletin No. 413).

All the bees in a hive are potentially susceptible to the pathogenic diseases detailed herein. Thus, according to some embodiments, the bees can be honeybees, forager bees, hive bees and the like.

Also provided is a method for reducing the susceptibility of a bee to a disease caused by pathogens, the method effected by feeding the bee on an effective amount of a nucleic acid or nucleic acid construct comprising a nucleic acid agent downregulating expression of a polypeptide of the bee pathogen and/or causing cleavage and/or degradation of a bee pathogen RNA. Methods for reducing the susceptibility of a bee colony or bee-hive to bee pathogens by feeding oligonucleotides and/or polynucleotides are envisaged. Thus, in some embodiments, the present invention can be used to benefit any numbers of bees, from a few in the hive, to the entire bee population within a hive and its surrounding area. It will be appreciated, that in addition to feeding of oligonucleotides and/or polynucleotides for reduction of the bee pathogen infection and infestation, enforcement of proper sanitation (for example, refraining from reuse of infested hives) can augment the effectiveness of treatment and prevention of infections.

It is expected that during the life of a patent maturing from this application many relevant methods for downregulating bee pathogen proteins will be developed and the scope of the term "downregulating bee pathogen protein" or "downregulating bee pathogen polypeptide" is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example I

Effect of IAPV Virus Titer on Survival of Honeybees

In order to determine whether bees are differentially sensitive to IAPV, the effect of virus titer on bee survival was tested. Bees were introduced into plastic containers and exposed to increasing concentrations of IAPV (in feed solution). Survival of the bees in the hive was monitored over a period of 7 days.

Materials and Methods 50 bees were introduced into 0.5 liter plastic containers, or 30 bees into 0.25 liter plastic containers.

All containers were prepared in advance to accommodate air flow and enable feeding with sucrose solution and water. The bees were kept in the dark at a constant temperature of 30° C., and were fed once daily with 2 ml 50% sucrose solution and 1 ml water introduced into reservoirs in the containers.

IAPV was introduced into the sucrose solution, in increasing doses (0.0001 to 0.1 microgram/microliter) in 900 microliters sucrose solution added to the sucrose: Vertical striped bars-100 ng/µl; Cross-hatched bars-10 ng/µl; Stippled bars-1.0 ng/µl; Horizontal striped bars-0.1 ng/µl. Controls (checkered bars) were without added virus. Dead bees in the containers were counted daily, and the total number of dead bees was calculated as a percentage of the initial number of bees introduced into the container.

Results

As can be seen in FIG. 1, bee mortality during the days 1 and 2 was negligible for all viral concentrations. Significant mortality, of 35-60% (depending on viral titer) was observed from day 3, steadily increasing to 70-85% by day 6-7. It was noted that lower viral doses resulted in an initially higher mortality, which plateaued by day 6, whereas mortality among bees exposed to higher concentrations continued to increase from day 3.

Example II

Feeding Viral-Specific dsRNA Prevents Acute Disease of Honeybees Caused by IAPV

In order to determine the effectiveness of ingested IAPV dsRNA on viral infection, honeybees were provided with IAPV-specific and control dsRNA in the feed for 4 days before, and 3 days following infection with IAPV virus. Numbers of dead bees per experimental hive were counted, and sample live and dead bees were collected for molecular analysis.

Materials and Methods

Establishment of Mini-Hive Colonies:

Young, approximately 2-month-old queens, together with approximately 200 worker bees were collected from hives in a local apiary. The bees were transferred into mini-hives fitted with one mini comb that was previously built by a regular hive. All of the mini-hives were closed and placed in a temperature-controlled room (30° C.).

dsRNA Preparation:

IAPV sequences corresponding to the intergenic region (bases 6168-6594; gi|124494152; 426 b SEQ ID NO: 33) and to a viral sequence known to integrate into the bee genome (bases 8977-9410; gi|124494152; 433 b, SEQ ID NO: 34) were cloned into a plasmid between two opposing T7 promoters. Following propagation of plasmid DNA, the viral fragments, including the T7 promoters, were excised, gel-purified, and served as templates for T7-directed in-vitro transcription (MEGAscript™, Ambion, Austin Tex.). The reaction product was submitted to DNase digestion followed by phenol extraction and ethanol precipitation. The final preparation was dissolved in nuclease-free water.

dsRNA Feeding in Minihives:

5 gr. pollen supplement patties were placed on top of each comb and 10 ml of 50% sucrose solution was introduced into the hive in a sterile Petri dish nightly. The feeding was continued for 7 days and subsequently only hives in which queens had begun to lay eggs were included in the trial.

Following establishment of active hives (queens laying eggs), some of the mini-hives were supplemented with viral-specific or non-specific control (IAPVds or GFPds) dsRNA, which was added to the 10 ml 50% sugar solution given to the hives, adjusted to approximately 1 microgram dsRNA per feed per bee, assuming all bees consume approximately the same amount of sucrose solution. dsRNA feeding was continued for six days.

IAPV Infection in Minihives:

Three days after feeding in active hives, some of the colonies were fed with 0.01 microgram per microliter of IAPV in the 50% w/v sucrose solution (IAPV). Thereafter dsRNA treatments continued for a further 3 days. Samples of live and dead bees (larvae and adults) were collected daily from each mini-hive post introduction of IAPV for 7 consecutive days. Every bee collected was frozen in liquid nitrogen and preserved at −70° C. pending molecular analysis. Vitality of the colonies was monitored by opening the hives (without smoke), withdrawing the mini-comb and photographing the mini-comb from both sides. The hive-combs were photographed daily, and the number of remaining live bees was monitored. The photographs were downloaded onto a computer and the total number of bees was counted for every mini-hive.

To test dsRNA toxicity, another group of hives was provided with IAPV-specific dsRNA, but was not IAPV inoculated. Two sets of hives served as additional controls: hives that were not treated with dsRNA and were not inoculated with IAPV, and hives that were not treated with dsRNA, but were inoculated with IAPV.

RT-PCR Analysis:

Extraction of Nucleic Acids:

Total RNA was extracted from the preserved bees using the TRIREAGENT method (Sigma, St. Louis Mo., USA). Briefly, RNA was extracted by precipitation and separation by centrifugation, then resuspended in RNAsecure solution.

Real-Time RT-PCR:

Measured amounts of RNA (100 ng for viral expression analyses and 100 pg for 18S rRNA internal controls) were subjected to one-step RT-PCR using the SYBR Green PCR master mix with Taqman reverse transcriptase (Applied Biosystems, Foster City, Calif.). Real-time RT-PCR was conducted in GeneAmp PCR System 5700 (Applied Biosystems). Reactions performed without reverse transcriptase or without template did not result in any product. PCR cycles were as follows: 1 cycle of 30 min at 48° C. and 10 min at 95° C., followed by 40 cycles each of 15 s at 95° C., 30 s at 60° C., and 45 s at 72° C.

Table III shows the primers for all IAPV-related RT-PCR assays, including real-time RT-PCR:

TABLE III

Primers used for PCR

| Primers & Purpose (5'-3') | SEQ ID | Amplified sequence (GenBank #) | Product size (bp) |
|---|---|---|---|
| IAPV: RT-PCR detection<br>F: AGACACCAATCACGGACCTCAC<br>R: GAGATTGTTTGAGAGGGGTGG | 35<br>36 | 8860-8997<br>(NC_009025) | 137 |
| Honeybee β-Actin: RT-PCR detection<br>F: ATGAAGATCCTTACAGAAAG<br>R: TCTTGTTTAGAGATCCACAT | 37<br>38 | 686-1200<br>(XM_393368) | 514 |
| IAPV: dsRNA synthesis<br>F: TAATACGACTCACTATAGGGCGACCA CCCCTCTCAAACAATCTCAAACA<br>R: TAATACGACTCACTATAGGGCGATA TATCCAGTTCAAGTGTCGGTTTTC | 39<br>40 | 8977-9385<br>(NC_009025) | 408 (excluding the T7 promoter (in bold)) |
| IAPV: dsRNA synthesis<br>F: TAATACGACTCACTATAGGGCGAGAC ACAATTCTTGAAATGCCAAACT<br>R: TAATACGACTCACTATAGGGCGACAT GTGTTACCATACGACTGCTGTAA | 41<br>42 | 6168-6594<br>(NC_009025) | 427 (excluding the T7 promoter (in bold)) |
| GFP: dsRNA synthesis<br>F: TAATACGACTCACTATAGGGCGAGC CAACACTTGTCACTACTTTCTCTT<br>R: TAATACGACTCACTATAGGGCGAAG GTAATGGTTGTCTGGTAAAAGGAC | 43<br>44 | 254-685<br>(U87625) | 432 (excluding the T7 promoter (in bold)) |
| Honeybee (β-Actin): Real-time PCR<br>F: TGCCAACACTGTCCTTTCTG<br>R: TTGCATTCTATCTGCGATTCC | 45<br>46 | 1000-1060<br>(XM_393368) | 61 |

Northern-Blot Analysis:

Total RNA was extracted from treated and control bees. Formaldehyde was added to the RNA to 1.8% and warmed to 65° C. The RNA, 15 μg per lane (in light of the real-time PCR results, only 1.5 μg of RNA was loaded in the case of upper leaves of inoculated plants), was electrophoresed on a 1.2% agarose gel at 70 V, 4° C. with stirring. The previously described amplified IAPV-RNA product was digoxigenin labeled and served as a probe for hybridization. Detection was performed with the DIG luminescent detection kit (Roche Diagnostics GmbH, Mannheim, Germany). RNA sizes were estimated by comparison to electrophoresed RNA Molecular Weight Markers I (Roche). Hybridization was carried out at high stringency (0.1×SSC; 65° C.).

Results

Figure 3:
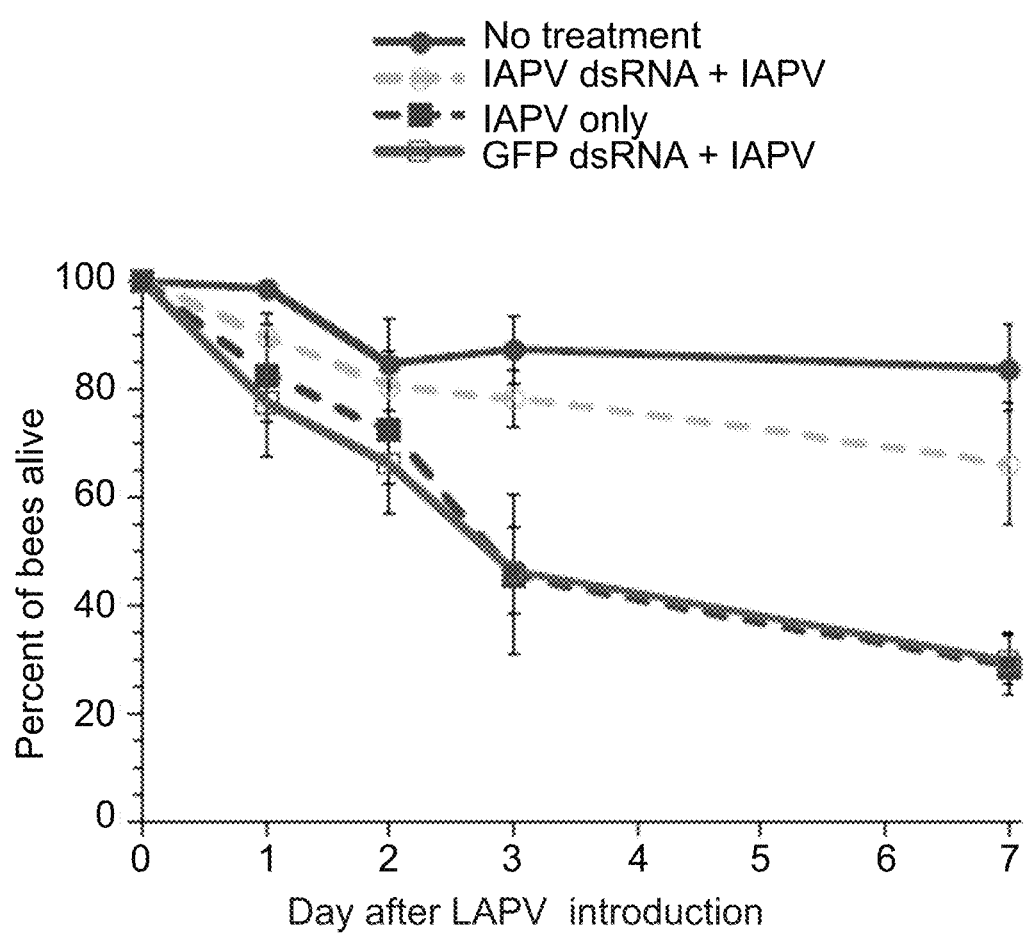
FIG. 3 is a graphic representation of bee survival following IAPV infection in the hives as treated in FIG. 2A to FIG. 2F. Filled squares (■) indicate virus exposure only (IAPV only). Empty circles (o) indicate virus exposure and IAVP-specific dsRNA feeding (IAPV dsRNA+IAPV). Empty squares (□) indicate virus exposure and non-specific dsRNA feeding (GFP dsRNA+IAPV). Filled circles (●) indicates no virus exposure and no dsRNA exposure (no treatment). Data are mean (+SE) estimated percent of bees alive. Statistical analyses were performed on arcsin square-root transformed proportions using JMP version 7.
Figure 4A:
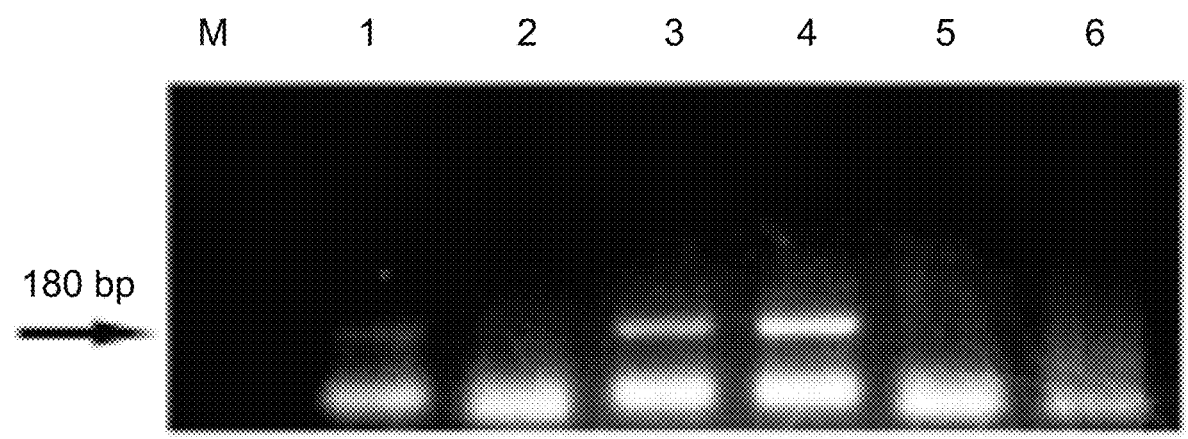
FIGS. 4A-4C are photographs of PAGE analysis of RT-PCR of bees from hives, treated as detailed in FIGS. 2A-2F and 3.
Figure 4B:
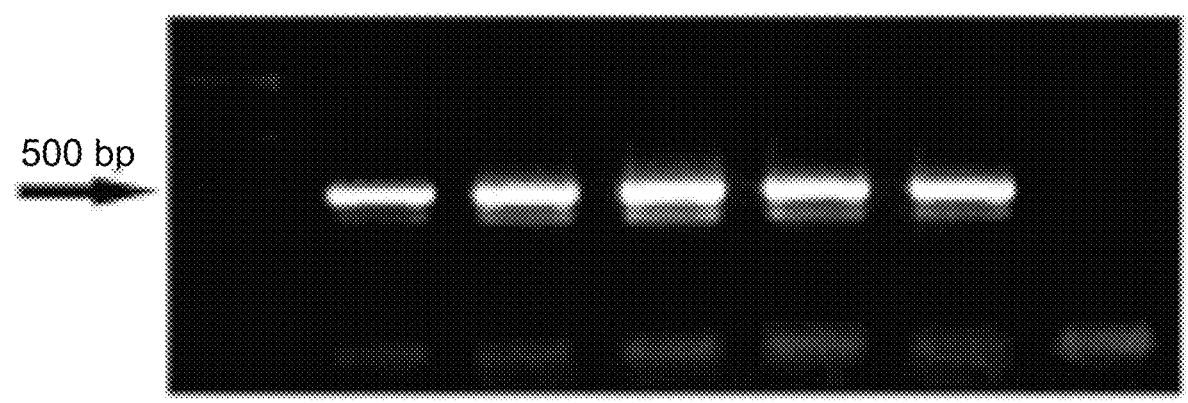
Figure 4C:
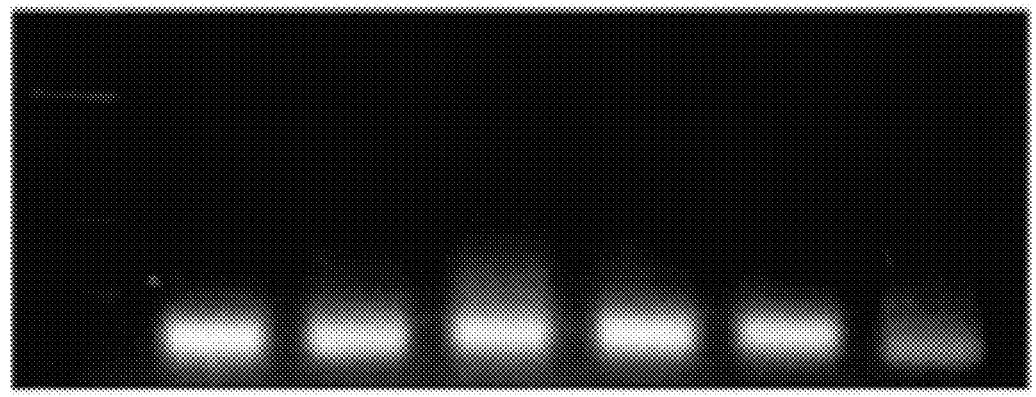
Figure 5:
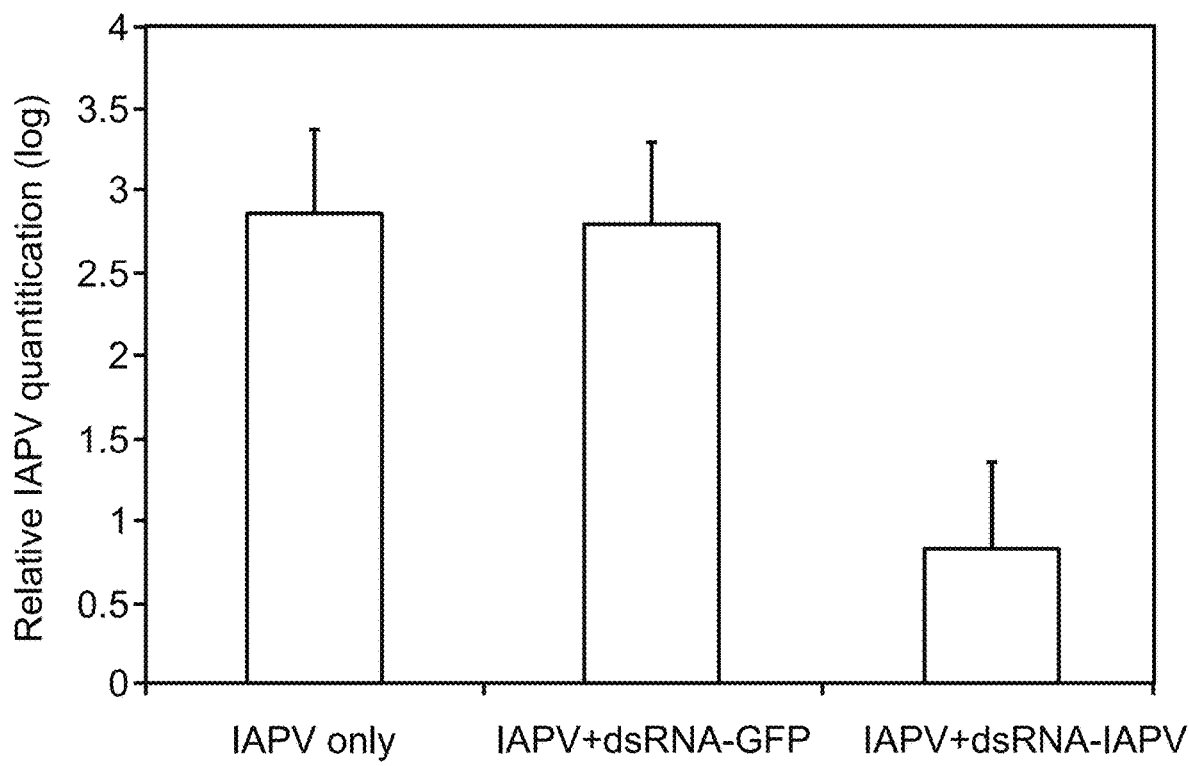
FIG. 5 is a histogram showing reduction in virus titer following IAVP-dsRNA treatment. Relative titers of virus (as determined by real-time PCT) were determined four days following IAPV inoculation in untreated bees (IAPV-only), sham (GFP) dsRNA treated bees (IAPV+dsRNA-GFP) and bees treated with IAVP-dsRNA (IAVP+dsRNA-IAVP). Relative titers were calibrated against virus titers in non-inoculated bees.
Figure 6:
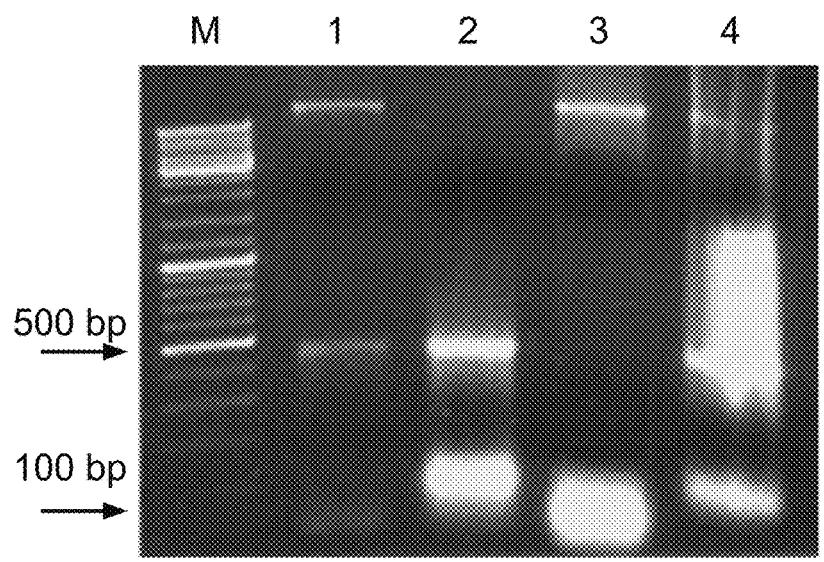
FIG. 6 is a photograph of a PAGE analysis showing the accumulation of dsRNA in bees fed with IAPV-specific dsRNA. Total bee RNA was extracted from dsRNA-fed bees as described herein, treated as indicated with RNase A, RNase III or DNA, separated on PAGE and stained for detection of prominent species. Lane 1: total RNA after digestion with RNase A. Lane 2: total RNA after digestion with DNase I. Lane 3: total RNA after digestion with RNase A+RNase III. Lane 4: untreated extract of total RNA. M is molecular weight markers. Note the presence of dsRNA (RNase A and DNase resistant, RNase III sensitive) band in lanes 1, 2, and 4.
Figure 7:
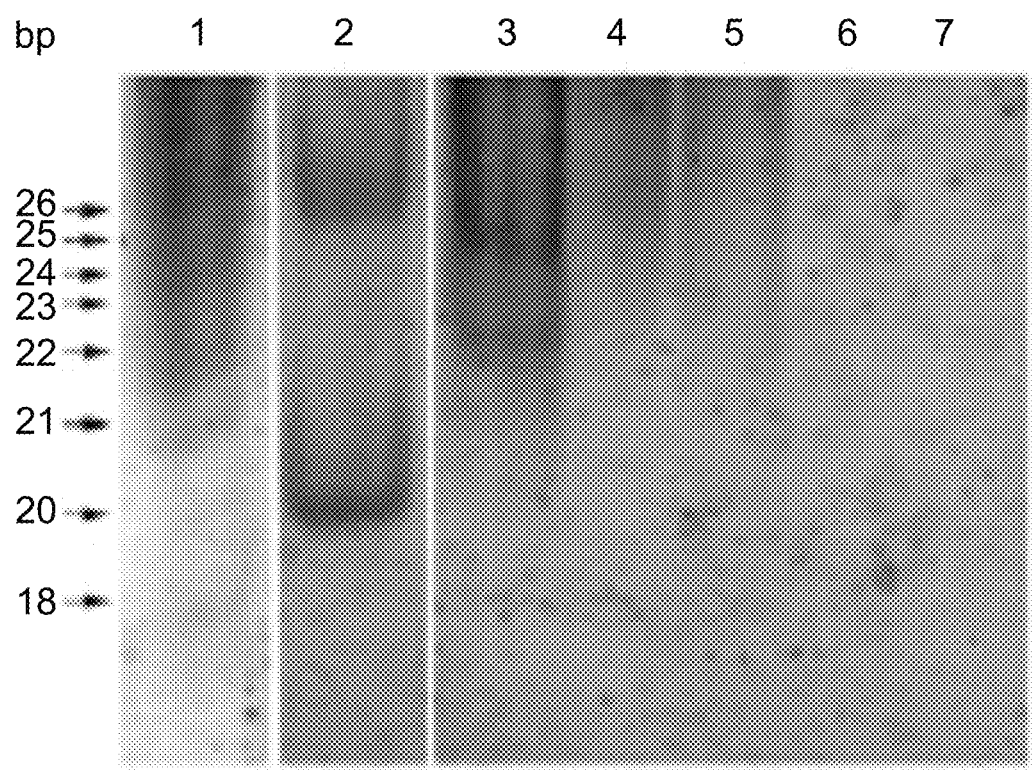
FIG. 7 is a photograph of a PAGE analysis showing the accumulation of IAPV-specific siRNA in bees fed with IAPV-specific dsRNA. Total bee RNA was extracted from dsRNA-fed bees as described herein, separated on PAGE and blotted onto a matrix for detection with a probe representing a segment of a IAPV structural protein. Lane 1: IAPV-dsRNA digested with RNaseIII, resulting in 18- to 26-bp fragments. Lane 2: synthetic primers for IAPV as size markers for 20- and 26-bp fragments. Lane 3: electrophoretic pattern of total RNA extracted from bees fed on IAPVdsRNA. Lane 4: blot of total RNA extracted from bees fed on GFP-dsRNA. Lanes 5 & 6: synthetic IAPV-dsRNA and GFP-dsRNA (respectively). The ca. 400-bp dsRNA was excluded from the siRNA gel. Lane 7: total RNA from untreated bees. Note the presence of IAPV-specific siRNA (21, 22, and 25 bp long) in bees fed on IAPV-dsRNA. Arrows indicate size in bp.

As can be seen in FIG. 3, among bees inoculated with IAPV (on day 0) mortality was significantly reduced (25% mortality) in bees treated with IAPV-dsRNA (empty circles) relative to untreated controls (filled squares) (75% mortality) and sham-treated controls (GFP-dsRNA, empty squares) (75% mortality) (LSmeans contrast, $F_{1,82}=9.74$, $P=0.002$). Mortality of bees treated with IAPV-dsRNA and inoculated with IAPV tended to increase relative to the noninfected bees (filled circles), though the difference did not reach statistical significance (LSmeans contrast, $F_{1,82}=3.25$, NS).

FIG. 3 clearly demonstrates the efficacy of feeding IAPV-dsRNA in protecting bees from subsequent IAPV infection, whereas unrelated dsRNA (sham treated controls—GFP) fails to protect bees from infection. Ingestion of sham dsRNA had no effect on the survival of the bees, relative to untreated controls. Ingestion of dsRNAs (of IAPV and GFP) without subsequent IAPV inoculation did not harm bees in any way, indicating absence of toxicity of the dsRNA.

When detecting RNA using RT-PCR, the effect of feeding dsRNA-IAVP on IAPV infection in the bees is clear. FIG. 4A shows that IAPV-dsRNA-treated bees carry only residual virus transcripts (lanes 1 and 2), whereas considerable amounts of virus transcripts are detected in the untreated (lane 4), and GFP-dsRNA-treated bees (lane 3). As indicated by the identity of the band size and intensity in lanes 1-5 (actin internal controls) of FIG. 4B, all samples contained comparable amounts of template RNA.

Using real-time PCR, FIG. 5 shows the strong decline in IAPV level detected in bee populations treated with IAPV-dsRNA. At the fourth day after inoculation of IAPV, real-time PCR detected approximately two orders of magnitude (2 log units) fewer IAPV in IAPV-dsRNA-treated bees as compared to that detected in bees that had not been treated with IAPV-dsRNA, or treated with unrelated (GFP) dsRNA (FIG. 5). With very few exceptions, the queens and a few nursing bees survived IAPV infection, a situation reminiscent of CCD-affected hives. Thus, the reduction in mortality among bees ingesting dsRNA-IAPV is clearly due to extensive reduction in the levels of viral infection and proliferation in the treated bees.

The Fate of Ingested IAPV-Specific dsRNA in Honeybees:

In order to better understand the mechanism(s) of action by which dsRNA-IAPV protects the bees against IAPV infection and its consequences, total RNA was extracted from dsRNA-IAPV treated, and non-treated control bees, submitted to digestion by a panel of nucleases, and separated on PAGE. As can be seen from FIG. 6 (see lanes 1, 2 and 3, representing digestion with RNase A, digestion with DNase I and digestion with RNase A and RNase II, respectively) the presence of a 500 base pair band representing dsRNA in the treated bees (RNase A and DNase I resistant, and RNase III sensitive) indicates actual, successful ingestion of the dsRNA-IAPV and its persistence in the bee.

When RNA extracted from dsRNA-IAPV treated, and control bees was separated, blotted and probed for IAPV-specific sequences (see FIG. 7) the presence of small IAPV-specific sequences exclusively in the RNA from dsRNA-IAPV bees (see FIG. 7, lane 3 vs FIG. 7, lanes 4-7) was detected. Thus, ingestion of dsRNA-IAPV initiates an RNAi related pathway, leading to the production of small IAPV specific peptides and the silencing of IAVP reproduction in the treated cells.

Taken together, these results show that IAPV can be silenced in bees by feeding with a segment or segments of IAPV-dsRNA and further indicate the activity of an RNAi-related pathway of silencing. The dsRNA-engendered silencing was sufficient to greatly reduce bee mortality resulting from IAPV infection.

Example III

Large-Scale Field Trials of Viral-Specific dsRNA for Prevention of IAPV-Associated Disease of Honeybees In order to determine the effectiveness of ingested IAPV dsRNA on viral infection under actual field conditions, and to assess effects on important parameters of colony health, bees in sample full size hives were provided with IAPV-specific dsRNA in the feed for 4 days before, and 3 days following infection with IAPV virus.

Materials and Methods

Insect Material:

Pools of five bees from the following treatments; Remote control, IAPV-dsRNA only, IAPV only and IAPV-specific dsRNA+IAPV at each time point day 0-(day of virus application), day 7 and end point (day 42). The test was repeated several times.

RNA Extraction:

RNA extracted using Tri-Reagent (Sigma, USA) according to protocol provided by the manufacturer. All samples treated with DNaseI and resuspended with loading buffer (90% Formamide, 0.05 Bromophenol Blue, 0.05% Xylene cyanol) prior to loading on gel.

Gel Electrophoresis and Blot:

10 ug of freshly prepared RNA was measured using the nanodrop spectrophotometer and loaded on 12% Acrylamide gel (1:19 acrylamide:Bis acrylamide ratio) in danturation environment (gel contains 7M Urea). After electrophoresis samples were transferred to positively charged nylon membrane (Roch, USA) using electroblotting method.

Hybridization and Signal Detection:

Membrane hybridized with freshly prepared DNA probe of IAPV segment, taken from a region that does not correspond to the dsRNA of the IAPV-specific dsRNA itself. This is made using DIG PCR probe preparation Kit (Roch, USA) o/n 42° C. in DIG easyhyb solution (Roch, USA) according to manufacturer protocol. The membrane was washed twice with 2×SSC/0.1% SDS than washed for stringency with 0.1×SSC/0.1% SDS in 65° C. Membranes were further washed using DIG Wash and Block Kit (Roch, USA) according to manufacturer protocol. Detection was preformed using CSPD-star substrate (Roch, USA). Positive control was 21 nt DNA primers corresponding to the hybridized sequence.

Signal was detected using membrane exposure for 2-12 hours in chemiluminator manufactured by Kodak Results Feeding IAPV-dsRNA to a Hive does not Affect Overall Health of the Colony:

Basic parameters of bee colony health (numbers of capped brood, numbers of bees in the hive, returning foragers and honey production) were assessed in hives fed IAPV-dsRNA and control hives, in the absence of infection with IAPV. Table IV presents the results of this comparison.

TABLE IV

Comparison between IAPV-dsRNA-treated and control hives

| | Mean (average) parameters in field trials | | | |
|---|---|---|---|---|
| | Capped brood overall ($cm^2$) | Estimated bees in the hive overall | Returning foragers overall | Honey production (kg) |
| Control | 2934 | 5834 | 28.9 | 3.8 |
| IAPV-specific dsRNA (w/o virus) | 3391 | 6781 | 29.5 | 3.5 |
| T-test | p > 0.19 | p > 0.12 | p > 0.68 | p > 0.84 |
| Conclusion | N.S. | N.S. | N.S. | N.S. |

Table IV clearly shows no significant differences between the treated and control hives in any of the measured parameters, indicating that feeding IAPV-dsRNA is benign to the bees and the colony as a whole, in the absence of IAPV infection.

Figure 11A:
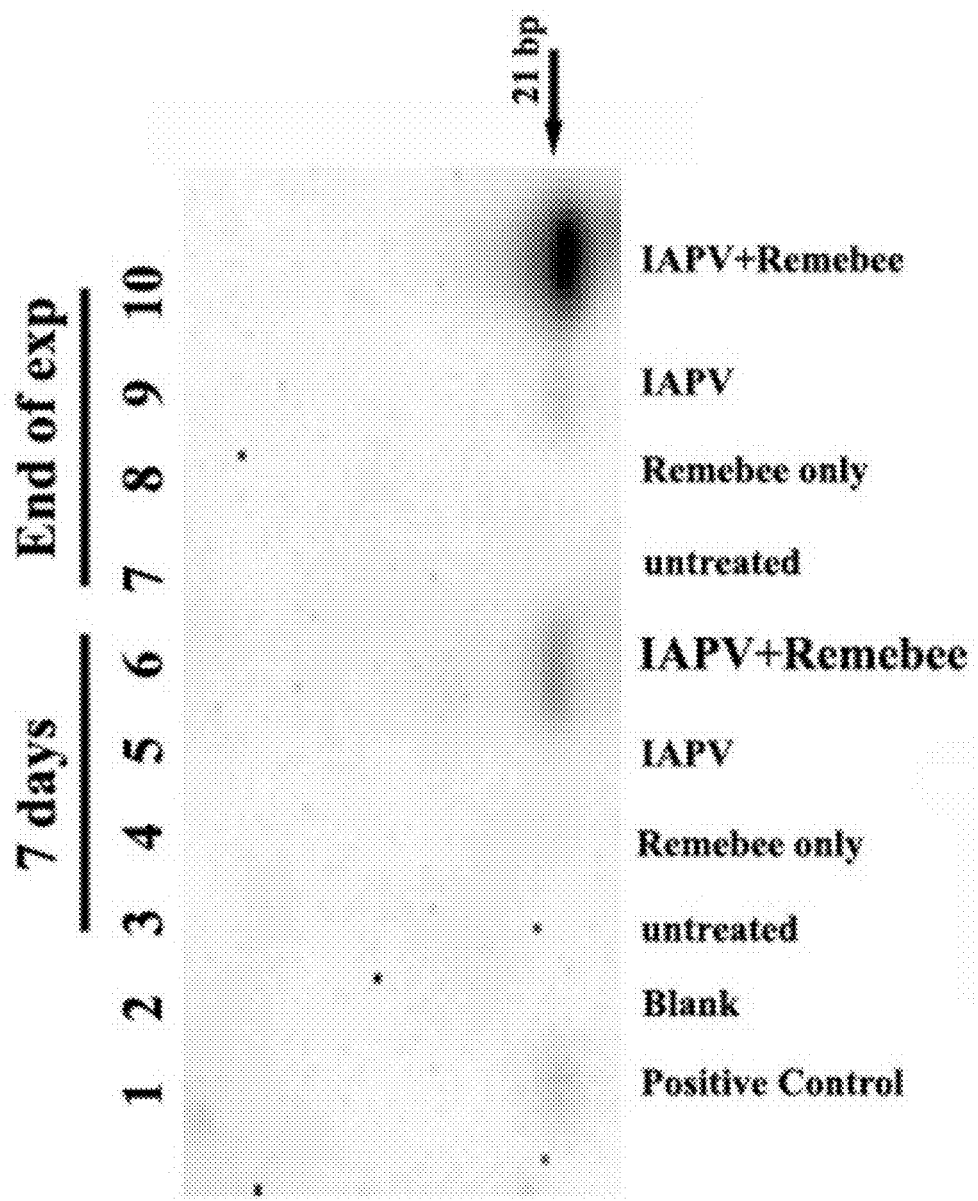
FIGS. 11A-11B are photographs of a PAGE analysis and Southern blot showing the accumulation of IAPV-specific siRNA in bees fed with IAPV-specific dsRNA in a large scale field trial.
Figure 11B:
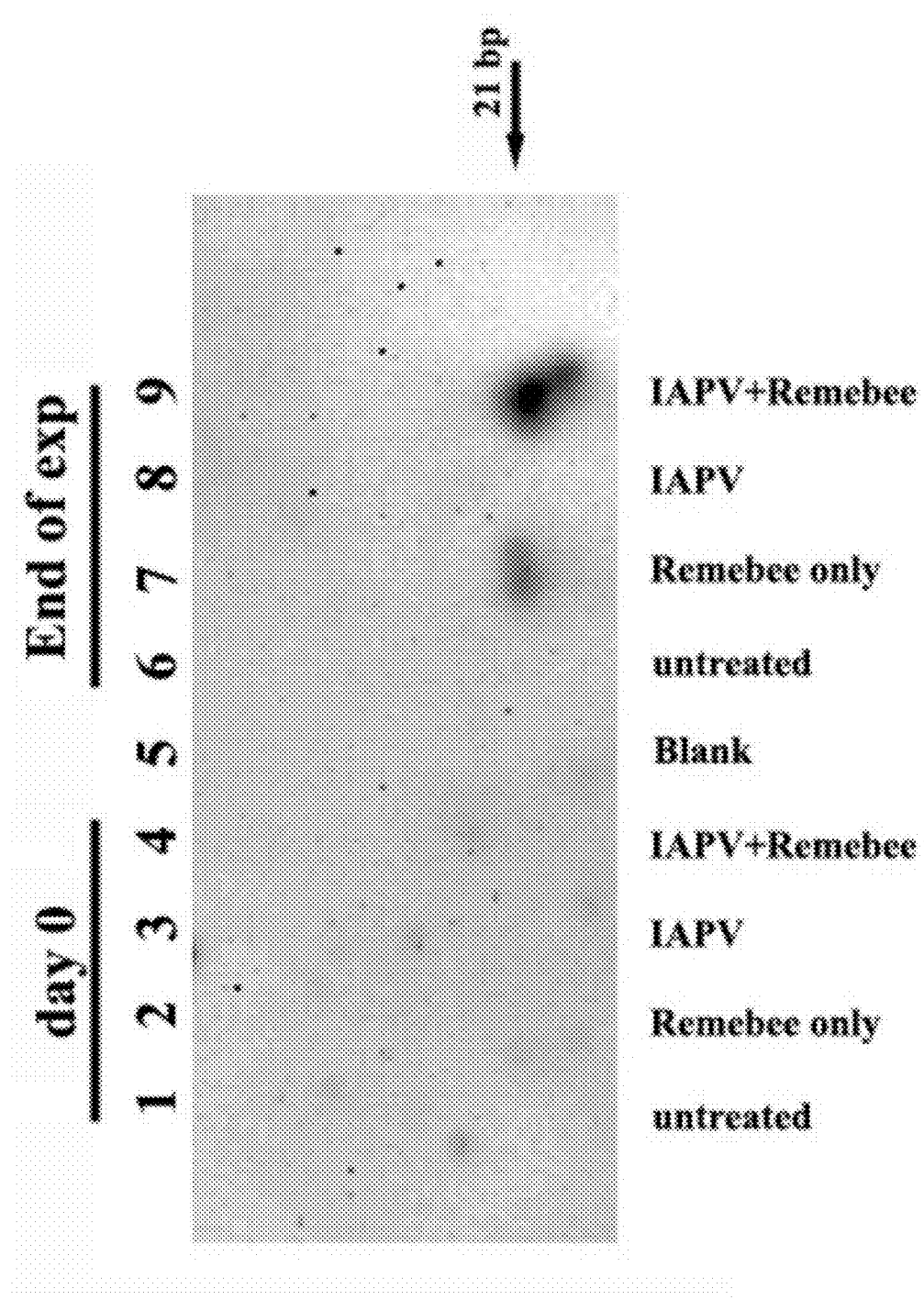

Detection of IAPV-Specific siRNAs in Treated Honeybees Under Field Conditions:

FIGS. 11A and 11B show siRNAs specific to IAPV sequence detected by gel electrophoresis and hybridization of honeybee RNA to a IAPV-specific probe. At day 0 no IAPV-specific siRNAs were detected in treated or untreated bees (FIG. 11B). By day 7, IAPV-specific siRNAs were detected exclusively in bees fed IAPV-specific dsRNA and infected with IAPV (FIG. 11A, lane 6). At the end if the experiment, day 42, IAPV-specific siRNA was detected weakly in one sample of RNA from IAPV-infected bees (FIG. 11A, lane 9) and also weakly detected in one sample from bees fed IAPV-specific dsRNA but not infected with IAPV (FIG. 11B, lane 7). In contrast both samples from bees fed IAPV-specific dsRNA and exposed to IAPV (FIG. 11A, lane 10 and FIG. 11B, lane 9) showed a strong signal at 21 bp, indicating greatly increased amounts of IAPV-specific siRNAs. Untreated (remote) control bees (FIG. 11A, lanes 1 and 7, FIG. 11B, lanes 1 and 6) showed no signal throughout the experimental period, indicating an absence of IAPV-specific sequences.

These results indicate that IAPV-specific siRNA is present in bees fed IAPV-specific dsRNA and exposed to IAPV infection only. While not wishing to be limited to a single hypothesis, it is postulated that where IAPV infection is severe, the initial IAPV-specific dsRNA silencing signal is amplified (IAPV-specific dsRNA plus IAPV infection, FIG. 11A lane 10 and FIG. 11B lane 9), the strong presence of siRNAs probably restricts the severity of the disease in the bees leading to a longer life-span.

IAPV-dsRNA Prevents Symptoms of IAPV in IAPV Infected Colonies

After establishing that IAPV-specific dsRNA alone did not make any difference relative to the untreated control, colonies receiving virus only and IAPV-specific dsRNA+ virus were compared to test the efficacy of the treatment in directly preventing the IAPV symptoms.

Figure 8:
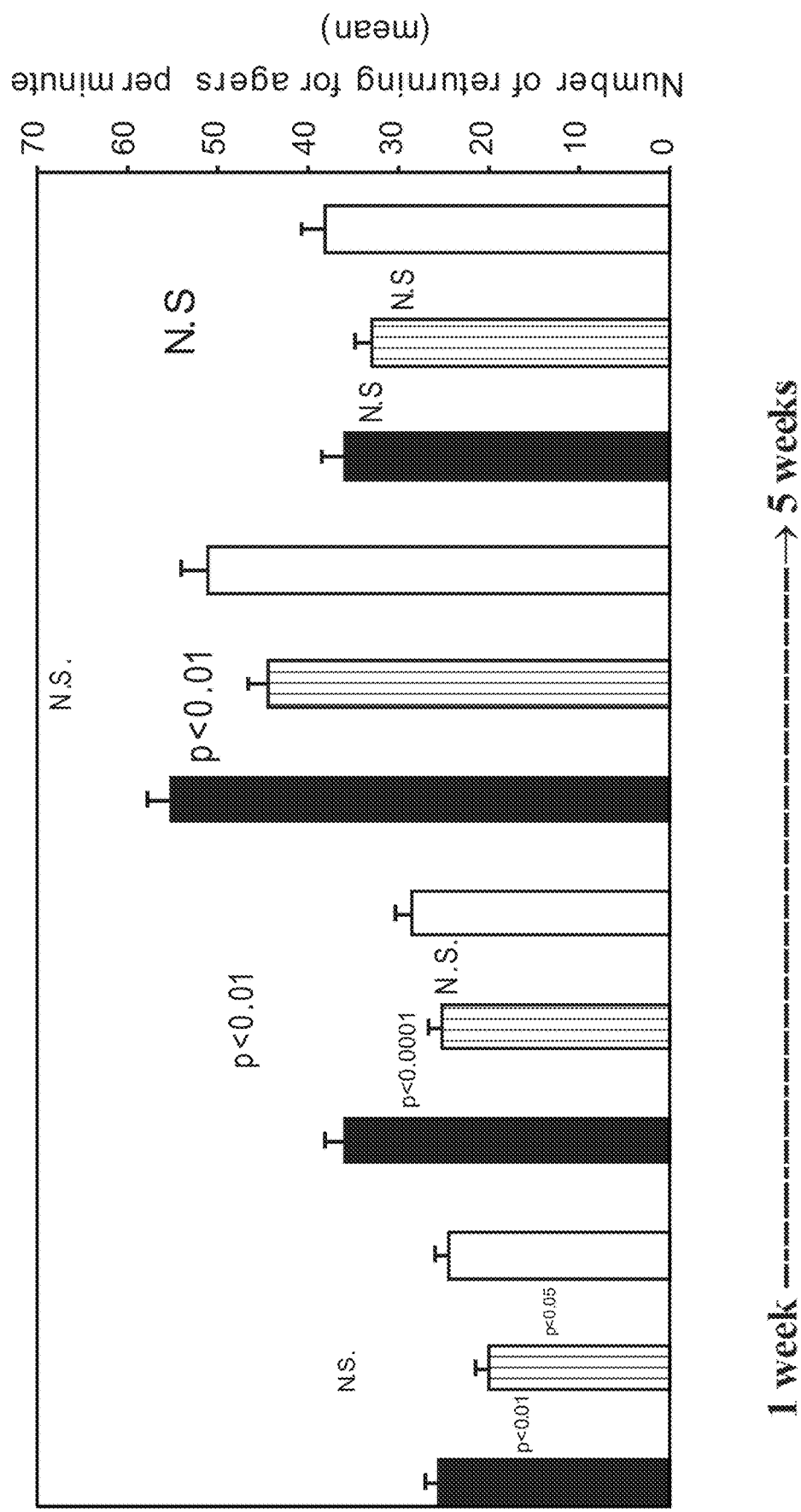
FIG. 8 is a histogram showing increased numbers of returning foragers in IAPV-dsRNA treated hives in large scale field trials. Separate hives received either IAPV alone (white bars), IAPV dsRNA+IAPV (lined bars) or no treatment (controls, black bars). Returning foragers were monitored on several occasions at several times of the day over a period of six weeks. Data is presented from one week following exposure to virus to 5 weeks after exposure. Note the progressively significant increase in numbers of returning foragers among the IAPV dsRNA-treated hives as compared with the IAPV-only hives.

Colony Collapse Disorder (CCD) is characterized by thinning of the affected colony due to reduced numbers of returning foragers, with dead bees typically found outside the hive. FIG. 8 shows the effect of feeding IAPV-dsRNA on the numbers of returning foragers in virus-infected colonies. At the beginning of the experiment, a small (insignificant) difference in the numbers of returning foragers can be discerned between the treatments. However, with greater time following IAPV infection the IAPV-specific dsRNA+ IAPV treated colonies showed progressively greater numbers of returning foragers, as compared to the other colonies. Without wishing to be limited to a single hypothesis, the initial differences in the numbers of returning foragers observed in the first week can be attributed to the death of foragers in the weeks following infection with IAPV.

Figure 9:
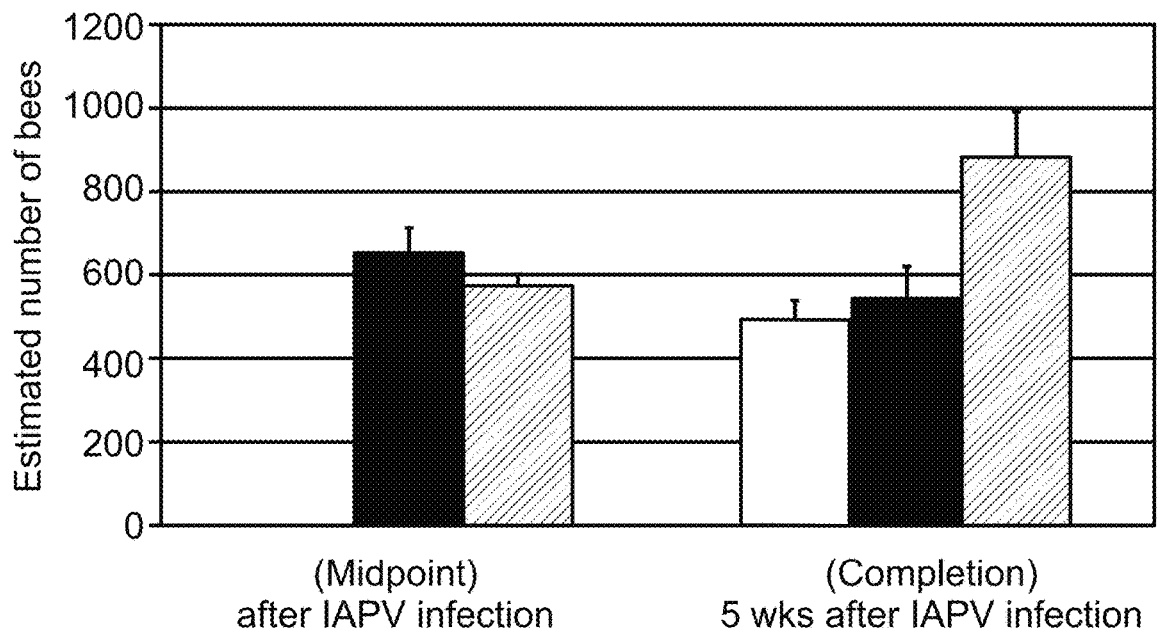
FIG. 9 is a histogram showing the effect of IAPV dsRNA on numbers of bees in the hive following IAPV infection in large scale field trails. Separate hives received either IAPV alone (white bars), IAPV dsRNA+IAPV (diagonal shaded bars) or no treatment (controls, black bars). Numbers of bees per hive was estimated at the mid-point (May 13) and at the end of the experiment (June 10). Note the significantly greater numbers of bees in the IAPV dsRNA-treated hives at the conclusion of the trial.

Another important parameter characteristic of CCD is a reduction in the total number of bees in the hive. FIG. 9 shows that although mid-point analysis of the field trial hives shows no difference in the estimated number of bees in the hives between treated and non-treated colonies, the advantages of IAPV specific-dsRNA were clearly evident by the end point of the trial. FIG. 9 shows that, at 5 weeks following IAPV infection, the estimated number of bees in the uninfected control and IAPV remained insignificantly different, whereas colonies receiving IAPV-specific dsRNA were significantly more populated ($p<0.01$).

Honey production of a hive reflects not only by the numbers of bees in the colony, but their overall health and robustness. Flight activity data was correlated with honey production in the treated and control colonies.

Figure 10:
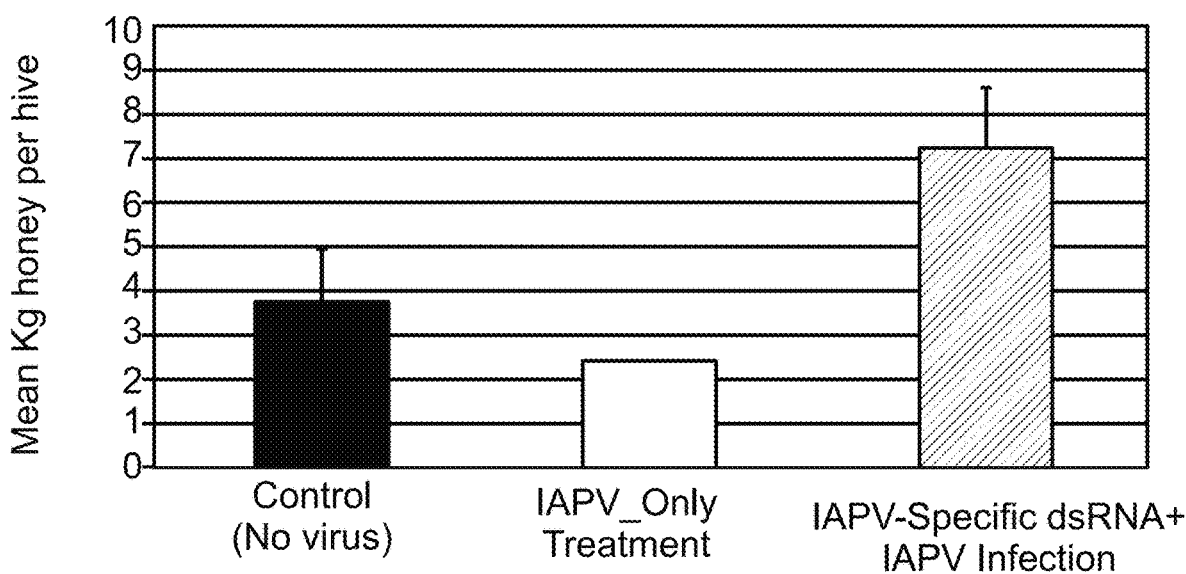
FIG. 10 is a histogram showing the effect of IAPV dsRNA on honey production in hives following IAPV infection in large scale field trails. Separate hives received either IAPV alone (white bar), IAPV dsRNA+IAPV (diagonal shaded bars) or no treatment (controls, black bar). Amount of honey (in Kg) per hive was weighed with a portable scale at the end of the experiment 6 weeks following IAPV infection. Note the significantly greater honey production in hives treated with IAPV-dsRNA+IAPV, as compared to untreated IAPV-infected and uninfected control hives.

When compared between IAPV-specific dsRNA and control colonies, flight activity data correlated strongly with honey production. FIG. 10 shows that IAPV-specific dsRNA+IAPV treated hives produced approximately three times more honey than IAPV-infected only hives and nearly twice the amount of honey of the uninfected control hives. Further, the number of hives producing significant honey was much greater in the IAPV-specific dsRNA than those in the untreated virus-infected colonies. Moreover, none (0%) of the IAPV-specific dsRNA treated colonies died during the experiment, compared to four dead out of 20 (20%) of the untreated, virus infected colonies and one dead out of 20 (5%) control colonies.

Taken together, these results show that silencing of IAPV in bees by feeding with a segment or segments of IAPV-dsRNA is effective in preventing symptoms of IAVP in infected colonies, resulting in greater viability of the bee colonies and surprisingly improved honey yields.

Example IV

Multiple Bee-Virus Resistance Sequence

In order to enhance the efficacy of the use of a nucleic acid agent in reducing susceptibility of the bees and bee colonies to viral pathogens, bee-viral sequences were compared for sequence homology, and a composite nucleic acid agent, comprising multiple bee-virus sequences was designed.

Figure 12:
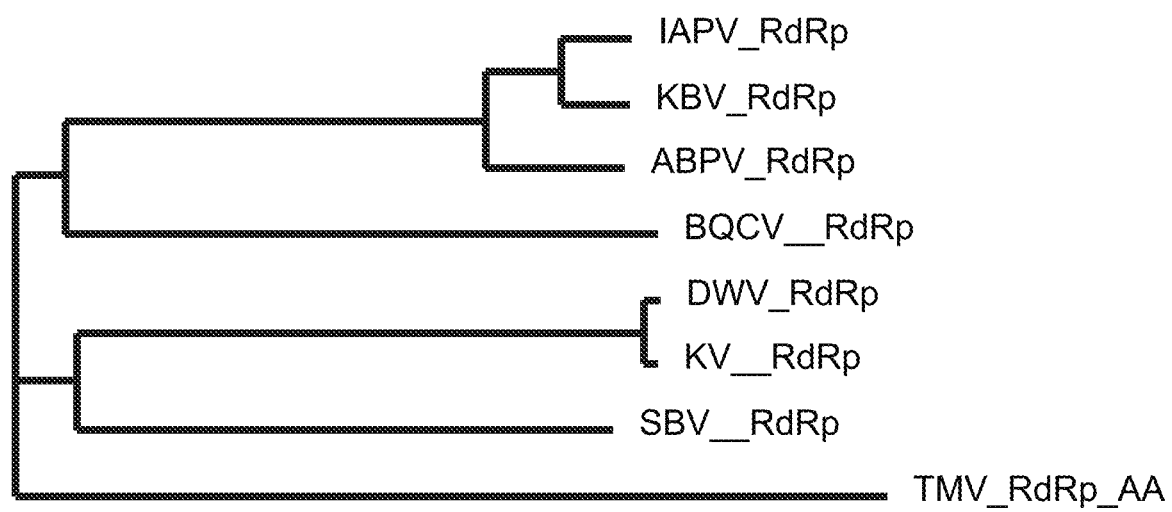
FIG. 12 is a schematic diagram showing the phylogenetic relationship between bee-viruses of the Picornavirus Superfamily.
Figure 13:
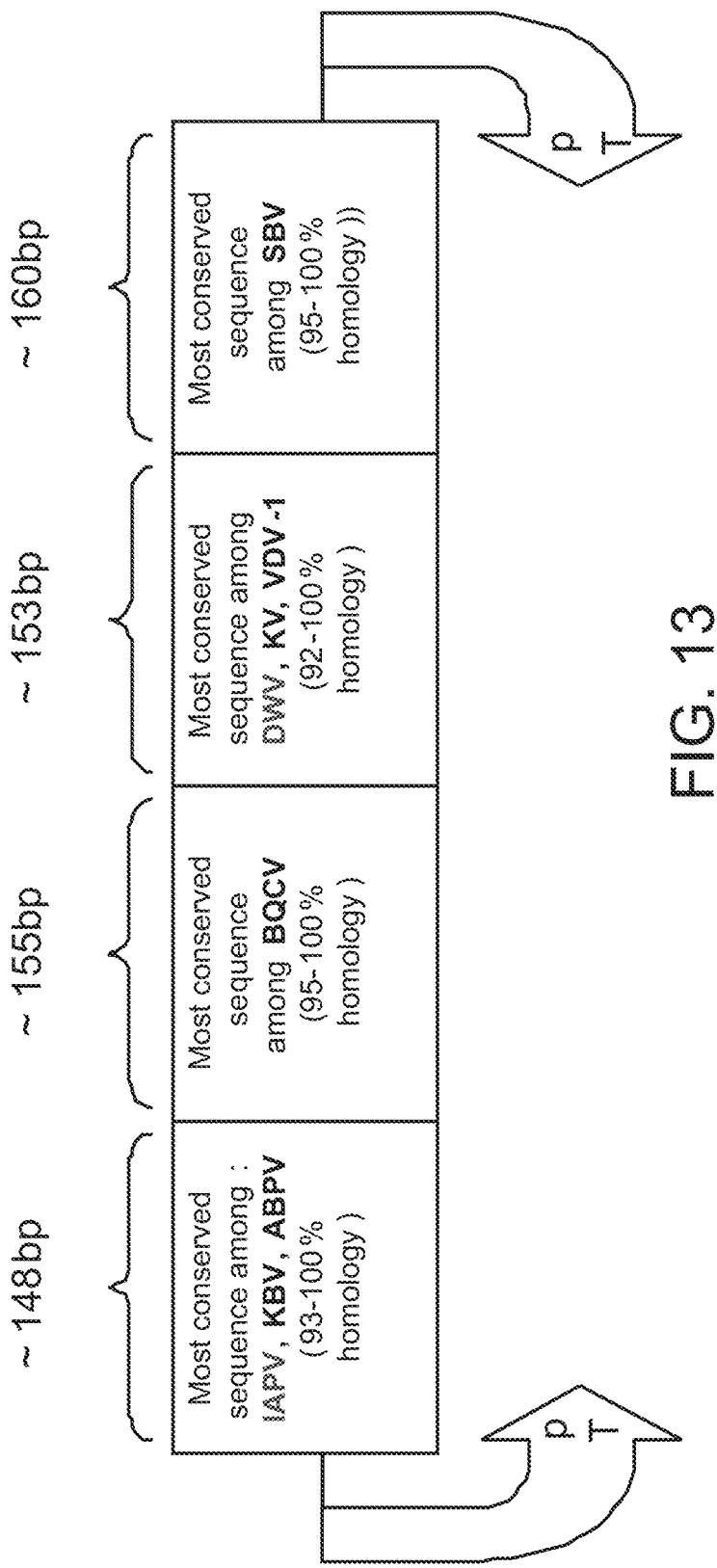
FIG. 13 is a diagrammatic illustration of the sequences comprising the multiple bee-virus resistance nucleic acid construct SEQ ID NO: 24.

FIG. 12 shows the phylogenetic relationship between several bee viruses whose genomes have been fully sequenced: Acute bee paralysis virus (ABPV)—GenBank AF150629 (SEQ ID NO: 3), Kashmir bee virus (KBV)—GenBank AY275710 (SEQ ID NO: 9), Sacbrood virus (SBV)—GenBank NC_002066 (SEQ ID NO: 2), Black queen cell virus (BQCV)—GenBank AF183905 (SEQ ID NO: 1), Kakugo virus (KV)—GenBank AB070959 (SEQ ID NO: 4), Deformed wing virus (DWV)—GenBank AJ489744 (SEQ ID NO: 53) and Israel acute paralysis virus (IAPV)—GenBank EF219380 (SEQ ID NO: 6). Sequences from IAPV having high homology to ABPV GenBank AF150629 (SEQ ID NO: 3) and KBV AY275710 (SEQ ID NO: 9) were identified by alignment of the viral genomes. Sequences from DWV having high homology to KV GenBank AB070959 (SEQ ID NO: 4) and VDV-1 GenBank AY251269 (SEQ ID NO: 5) were also identified by alignment of the viral genomes. To these, sequences from the BQCV genome (SEQ ID NO: 1) and SBV genome (SEQ ID NO: 2) were added, and a composite nucleic acid construct having high sequence homology to all of the abovementioned bee viruses (with added pT7 viral sequences) was produced (SEQ ID NO: 24, FIG. 13).

Table V shows the primers useful for creating multiple bee-virus resistance dsRNA:

TABLE V

Primers used for multiple bee-virus resistance dsRNA

| Primers & Purpose (5'-3') | SEQ ID | Amplified sequence | Product size(bp) |
|---|---|---|---|
| IAPV/ABPV/KBV homology<br>F: AAGAAATCAACCTTTCATGATG (59° C.)<br>R: ATCTCAATGTTGTCAATGAGA (59° C.) | <br>25<br>26 | SEQ ID NO: 47 | 148 |
| BQCV<br>F: CAATACCTATAAAGGGAGTCGCA (60.7° C.)<br>R: TAATAGCGATTGACGGTGGG (60.8° C.) | <br>27<br>28 | SEQ ID NO: 48 | 155 |
| DWV/KV/VDV-1 homology<br>F: ACGTTAATGCGACGATATCAAT (58° C.)<br>R: ATTAAAGATTTCATGTGGAGAGC (57° C.) | <br>29<br>30 | SEQ ID NO: 49 | 153 |
| SBV<br>F: GTTGGAGGCGCGTAATTGC (63.9° C.)<br>R: CATCACTGGACATTTCGTGTAGT (62.9 C.) | <br>31<br>32 | SEQ ID NO: 50 | 160 |

It will be appreciated that feeding bees with a dsRNA comprising this multiple bee-viral homologous sequence will be effective in treating and preventing infection and symptoms of a broad variety of bee-viral infections in affected colonies. Yet further, without being limited to a single hypotheses, it is suggested that the numerous consensus sequences reflecting the high cross-species homology of the multiple bee-virus construct (SEQ ID NO: 24) can be processed (in the cell, by dsRNA processing enzymes) to RNAi effective against many bee viruses, including bee-viruses not yet identified and/or sequenced.

It will be appreciated that multiple bee-pathogen sequences for dsRNA effective in protecting against more than one species or variant can be determined in a similar manner for non-viral bee pathogens, for example, using the sequences of the pathogenic organisms detailed in Table II above. Multiple bee-pathogen sequences can include sequences within a certain class of pathogens (e.g. viruses, bacteria), or even include sequences effective for different and diverse classes of pathogens (e.g, viruses+bacteria+fungi, etc).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10888579B2). An electronic copy of the "Sequence Listing" will also be available from the USPTO upon request and payment of the fee set forth in 37 CFR 1.19(b)(3).

What is claimed is:

1. A method for increasing the tolerance of an adult bee to a disease caused by at least one bee pathogen, comprising feeding the adult bee an effective amount of a bee-ingestible composition comprising bee feed and a double stranded ribonucleic acid (dsRNA) comprising an RNA sequence capable of hybridizing to an mRNA transcript encoding a polypeptide or an RNA target sequence of the at least one bee pathogen, thereby increasing the tolerance of the adult bee to the disease, wherein the dsRNA is a naked dsRNA and the bee-ingestible composition does not comprise a transfection promoting agent.

2. The method of claim 1, wherein the at least one bee pathogen is selected from the group consisting of Acute Bee Paralysis Virus (ABPV), Kashmir Bee Virus (KBV), Sacbrood virus (SBV), Black queen cell virus (BQCV), Kakugo virus (KV), Deformed wing virus (DWV), and Israel acute paralysis virus (IAPV).

3. The method of claim 1, wherein the dsRNA comprises an RNA sequence that is complementary to at least 21 nucleotides of a nucleotide sequence set forth in SEQ ID NO: 47.

4. The method of claim 1, wherein the dsRNA comprises an RNA sequence that is complementary to at least 21 nucleotides of a nucleotide sequence set forth in SEQ ID NO: 50.

5. The method of claim 1, wherein the dsRNA comprises an RNA sequence that is complementary to at least 21 nucleotides of a nucleotide sequence set forth in SEQ ID NO: 24.

6. The method of claim 1, wherein the dsRNA is selected from the group consisting of siRNA, shRNA, and miRNA.

7. The method of claim 1, wherein the bee-ingestible composition is in solid form.

8. The method of claim 1, wherein the bee-ingestible composition is in liquid form.

9. The method of claim 1, wherein the bee-ingestible composition comprises a protein.

10. A bee-ingestible composition comprising bee feed and a double stranded ribonucleic acid (dsRNA) comprising an RNA sequence capable of hybridizing to an mRNA transcript encoding a polypeptide or an RNA target sequence of at least one bee pathogen,
    wherein the dsRNA comprises an RNA sequence that is complementary to at least 21 nucleotides of a nucleotide sequence set forth in SEQ ID NO:24, SEQ ID NO:47, or SEQ ID NO:50, and
    wherein the dsRNA is a naked dsRNA and the bee-ingestible composition does not comprise a transfection promoting agent, and whereby an adult bee fed with the bee-ingestible composition increases its tolerance to a disease caused by the at least one bee pathogen.

11. The bee-ingestible composition of claim 10, wherein the at least one bee pathogen is selected from the group consisting of Acute Bee Paralysis Virus (ABPV), Kashmir Bee Virus (KBV), Sacbrood virus (SBV), Black queen cell virus (BQCV), Kakugo virus (KV), Deformed wing virus (DWV), and Israel acute paralysis virus (IAPV).

12. The bee-ingestible composition of claim 10, wherein the dsRNA comprises an RNA sequence that is complementary to at least 21 nucleotides of a nucleotide sequence set forth in SEQ ID NO: 47.

13. The bee-ingestible composition of claim 10, wherein the dsRNA comprises an RNA sequence that is complementary to at least 21 nucleotides of a nucleotide sequence set forth in SEQ ID NO: 50.

14. The bee-ingestible composition of claim 10, wherein the dsRNA comprises an RNA sequence that is complementary to at least 21 nucleotides of a nucleotide sequence set forth in SEQ ID NO: 24.

15. The bee-ingestible composition of claim 10, wherein the bee-ingestible composition is in solid form.

16. The bee-ingestible composition of claim 10, wherein the bee-ingestible composition is in liquid form.

17. The bee-ingestible composition of claim 10, wherein the bee-ingestible composition comprises a protein.

18. The bee-ingestible composition of claim 10, wherein the bee-ingestible composition comprises a carbohydrate or sugar supplement.

19. The bee-ingestible composition of claim 10, wherein the dsRNA is selected from the group consisting of siRNA, shRNA, and miRNA.

\* \* \* \* \*